(12) United States Patent
Burger et al.

(10) Patent No.: US 8,168,794 B2
(45) Date of Patent: May 1, 2012

(54) PIM KINASE INHIBITORS AND METHODS OF THEIR USE

(75) Inventors: Matthew Burger, Albany, CA (US); Jiong Lan, Moraga, CA (US); Mika Lindvall, Oakland, CA (US); Gisele Nishiguchi, Albany, CA (US); Michelle Tetalman, Oakland, CA (US)

(73) Assignee: Novartis AG, Basel (CH)

( * ) Notice: Subject to any disclaimer, the term of this patent is extended or adjusted under 35 U.S.C. 154(b) by 396 days.

(21) Appl. No.: 12/380,458

(22) Filed: Feb. 26, 2009

(65) Prior Publication Data
US 2010/0216839 A1 Aug. 26, 2010

Related U.S. Application Data

(60) Provisional application No. 61/033,359, filed on Mar. 3, 2008.

(51) Int. Cl.
*A61K 31/4545* (2006.01)
*C07D 213/75* (2006.01)
*C07D 417/12* (2006.01)
*C07D 413/14* (2006.01)
(52) U.S. Cl. ............... 546/270.7; 546/193; 514/318; 514/342
(58) Field of Classification Search ............ 546/193, 546/270.7; 514/318, 342
See application file for complete search history.

(56) References Cited

U.S. PATENT DOCUMENTS

2009/0286766 A1* 11/2009 Sugasawa et al. ....... 514/210.18

FOREIGN PATENT DOCUMENTS

| CA | 2649043 | 11/2007 |
|---|---|---|
| WO | WO 2007/058942 | 5/2007 |
| WO | WO 2007123269 A1 * | 11/2007 |
| WO | WO 2008/054701 | 5/2008 |
| WO | WO 2008/054702 | 5/2008 |
| WO | WO 2008/054749 | 5/2008 |

* cited by examiner

*Primary Examiner* — David K O Dell
(74) *Attorney, Agent, or Firm* — Michael G. Smith

(57) ABSTRACT

The present invention relates to new compounds of Formulas I and II, their tautomers, stereoisomers and polymorphs, and pharmaceutically acceptable salts, esters, metabolites or prodrugs thereof, compositions of the new compounds together with pharmaceutically acceptable carriers, and uses of the new compounds, either alone or in combination with at least one additional therapeutic agent, in the inhibition of Pim kinase activity and/or the prophylaxis or treatment of cancer.

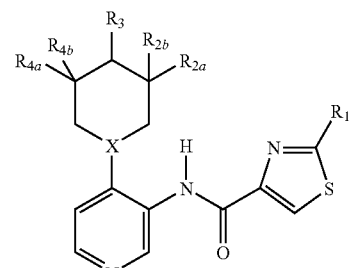

(I)

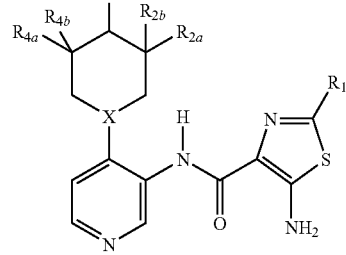

(II)

14 Claims, No Drawings

PIM KINASE INHIBITORS AND METHODS OF THEIR USE

This application claims benefit of priority under 35 U.S.C. 119(e) to U.S. Provisional Application Ser. No. 61/033,359, filed Mar. 3, 2008.

FIELD OF THE INVENTION

The present invention relates to new compounds, their tautomers, stereoisomers and polymorphs, and pharmaceutically acceptable salts, esters, metabolites or prodrugs thereof, compositions of the new compounds together with pharmaceutically acceptable carriers, and uses of the new compounds, either alone or in combination with at least one additional therapeutic agent, in the prophylaxis or treatment of cancer.

BACKGROUND

Infection with the Maloney retrovirus and genome integration in the host cell genome results in development of lymphomas in mice. Provirus Integration of Maloney Kinase (PIM-Kinase) was identified as one of the frequent proto-oncogenes capable of being transcriptionally activated by this retrovirus integration event (Cuypers H T et al., "Murine leukemia virus-induced T-cell lymphomagenesis: integration of proviruses in a distinct chromosomal region," *Cell* 37(1): 141-50 (1984); Selten G, et al., "Proviral activation of the putative oncogene Pim-1 in MuLV induced T-cell lymphomas" *EMBO J* 4(7): 1793-8 (1985)), thus establishing a correlation between over-expression of this kinase and its oncogenic potential. Sequence homology analysis demonstrated that there are 3 highly homologous Pim-Kinases (Pim1, 2 & 3), Pim1 being the proto-oncogene originally identified by retrovirus integration. Furthermore, transgenic mice over-expressing Pim1 or Pim2 show increased incidence of T-cell lymphomas (Breuer M et al., "Very high frequency of lymphoma induction by a chemical carcinogen in pim-1 transgenic mice" *Nature* 340(6228):61-3 (1989)), while over-expression in conjunction with c-myc is associated with incidence of B-cell lymphomas (Verbeek S et al., "Mice bearing the E mu-myc and E mu-pim-1 transgenes develop pre-B-cell leukemia prenatally" *Mol Cell Biol* 11(2):1176-9 (1991)). Thus, these animal models establish a strong correlation between Pim over-expression and oncogenesis in hematopoietic malignancies. In addition to these animal models, Pim over-expression has been reported in many other human malignancies. Pim1, 2 & 3 over-expression is frequently observed in many hematopoietic malignancies (Amson R et al., "The human protooncogene product p33pim is expressed during fetal hematopoiesis and in diverse leukemias," *PNAS USA* 86(22):8857-61 (1989); Cohen A M et al., "Increased expression of the hPim-2 gene in human chronic lymphocytic leukemia and non-Hodgkin lymphoma," *Leuk Lymph* 45(5):951-5 (2004), Huttmann A et al., "Gene expression signatures separate B-cell chronic lymphocytic leukaemia prognostic subgroups defined by ZAP-70 and CD38 expression status," *Leukemia* 20:1774-1782 (2006)) and in prostate cancer (Dhanasekaran S M, et al., "Delineation of prognostic biomarkers in prostate cancer," *Nature* 412(6849): 822-6 (2001); Cibull T L, et al., "Overexpression of Pim-1 during progression of prostatic adenocarcinoma," *J Clin Pathol* 59(3):285-8 (2006)), while over-expression of Pim3 is frequently observed in hepatocellular carcinoma (Fujii C, et al., "Aberrant expression of serine/threonine kinase Pim-3 in hepatocellular carcinoma development and its role in the proliferation of human hepatoma cell lines," *Int J Cancer* 114:209-218 (2005)) and pancreatic cancer (Li Y Y et al., "Pim-3, a proto-oncogene with serine/threonine kinase activity, is aberrantly expressed in human pancreatic cancer and phosphorylates bad to block bad-mediated apoptosis in human pancreatic cancer cell lines," *Cancer Res* 66(13):6741-7 (2006)).

Pim1, 2 & 3 are Serine/Threonine kinases normally function in survival and proliferation of hematopoietic cells in response to growth factors and cytokines. Cytokines signaling through the Jak/Stat pathway leads to activation of transcription of the Pim genes and synthesis of the proteins. No further post-translational modifications are required for the Kinase Pim activity. Thus, signaling down stream is primarily controlled at the transcriptional/translational and protein turnover level. Substrates for Pim kinases include regulators of apoptosis such as the Bcl-2 family member BAD (Aho T et al., "Pim-1 kinase promotes inactivation of the pro-apoptotic Bad protein by phosphorylating it on the Ser112 gatekeeper site,: *FEBS Letters* 571: 43-49 (2004)), cell cycle regulators such as $p21^{WFA1/CIP1}$ (Wang Z, et al., "Phosphorylation of the cell cycle inhibitor p21Cip1/WAF1 by Pim-1 kinase," *Biochim Biophys Acta* 1593:45-55 (2002)), CDC25A (1999), C-TAK (Bachmann M et al., "The Oncogenic Serine/Threonine Kinase Pim-1 Phosphorylates and Inhibits the Activity of Cdc25C-associated Kinase 1 (C-TAK1). A novel role for Pim-1 at the G2/M cell cycle checkpoint," *J Biol Chem* 179: 48319-48328 (2004)) and NuMA (Bhattacharya N, et al., "Pim-1 associates with protein complexes necessary for mitosis," *Chromosoma* 111(2):80-95 (2002)) and the protein synthesis regulator 4EBP1 (Hammerman P S et al, "Pim and Akt oncogenes are independent regulators of hematopoietic cell growth and survival," *Blood* 105(11):4477-83 (2005)). The effects of Pim(s) in these regulators are consistent with a role in protection from apoptosis and promotion of cell proliferation and growth. Thus, over-expression of Pim(s) in cancer is thought to play a role in promoting survival and proliferation of cancer cells and, therefore, their inhibitions should be an effective way of treating cancers on which they are over-expressed. In fact several reports indicate that knocking down expression of Pim(s) with siRNA results in inhibition of proliferation and cell death (Dai J M, et al., "Antisense oligodeoxynucleotides targeting the serine/threonine kinase Pim-2 inhibited proliferation of DU-145 cells," *Acta Pharmacol Sin* 26(3):364-8 (2005); Fujii et al 2005; Li et al 2006). Furthermore, mutational activation of several well know oncogenes in hematopoietic malignancies are thought exert its effects at least in part through Pim(s). For example, targeted down regulation of pim expression impairs survival of hematopoietic cells transformed by Flt3 and BCR/ABL (Adam et al 2006). Thus, inhibitors to Pim1, 2 & 3 would be useful in the treatment of these malignancies. In addition to a potential role in cancer treatment and myeloproliferative diseases, such inhibitor could be useful to control expansion of immune cells in other pathologic condition such as autoimmune diseases, allergic reactions and in organ transplantation rejection syndromes. This notion is supported by the findings that differentiation of Th1 Helper T-cells by IL-12 and IFN-α results in induction of expression of both Pim1&2 (Aho T et al, "Expression of human Pim family genes is selectively up-regulated by cytokines promoting T helper type 1, but not T helper type 2, cell differentiation," *Immunology* 116: 82-88 (2005)). Moreover, Pim(s) expression is inhibited in both cell types by the immunosuppressive TGF-β (Aho et al 2005). These results suggest that Pim kinases are involved in the early differentiation process of Helper T-cells, which coordinate the immunological responses in autoimmune diseases, allergic reaction and tissue transplant rejection.

A continuing need exists for compounds that inhibit the proliferation of capillaries, inhibit the growth of tumors, treat cancer, modulate cell cycle arrest, and/or inhibit molecules such as Pim1, Pim2, and Pim3 and pharmaceutical formulations and medicaments that contain such compounds. A need also exists for methods of administering such compounds, pharmaceutical formulations, and medicaments to patients or subjects in need thereof.

SUMMARY OF THE INVENTION

The present invention provides a compound of Formula I, or a stereoisomer, tautomer, or pharmaceutically acceptable salt thereof,

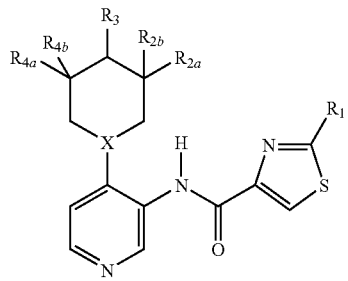

(I)

wherein,
$R_1$ is selected from

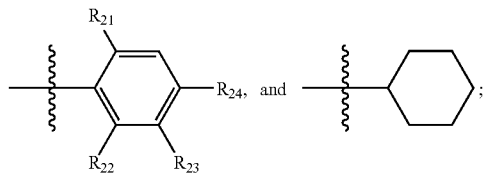

X represents CH, or N;
$R_{2a}$ is selected from amino, methyl, $CH_2F$, $CF_3$, $C_2H_5$, and H;
$R_{2b}$ is selected from H, and methyl;
$R_3$ is selected from H, OH, $OCH_3$, $CH_3$, F, and Cl;
$R_{4a}$ is selected from amino, methyl, OH, $OCH_3$, $OC_2H_5$, F, $CF_3$, H, and ethyl;
$R_{4b}$ is selected from methyl, H, and F;
$R_{21}$ represents H or F;
$R_{22}$ represents H, Cl, or F;
$R_{23}$ represents F, $OC_2H_5$, $OCH_3$, Cl, H, methyl, OH, or $OCH(CH_3)_2$; and
$R_{24}$ represents H or OH.

In another aspect, the present invention provides a compound of Formula II, or a stereoisomer, tautomer, or pharmaceutically acceptable salt thereof,

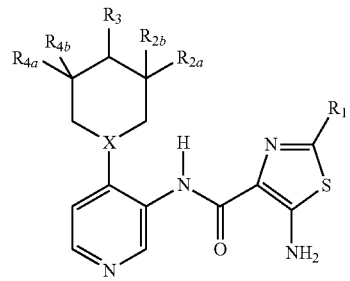

(II)

wherein:
$R_1$ is selected from —NH—CO-alkyl, substituted or unsubstituted cycloalkyl, substituted or unsubstituted heterocycloalkyl, substituted or unsubstituted aryl, and substituted or unsubstituted heteroaryl;
X represents CH or N;
$R_{2a}$ is selected from —H, —OH, alkyl, alkoxy, haloalkyl, aminoalkyl, hydroxyalkyl, halo, amino and bezoate;
$R_{2b}$ is selected from —H and alkyl;
$R_3$ is selected from H, OH, alkyl, alkoxy and halo;
$R_{4a}$ is selected from —OH, alkyl, alkoxy, haloalkyl, aminoalkyl, hydroxyalkyl, halo and amino; and
$R_{4b}$ is selected from H, alkyl and halo.

Another aspect of the present invention provides a composition comprising a therapeutically effective amount of compound of Formula I or Formula II, or a stereoisomer, tautomer, or pharmaceutically acceptable salt thereof, together with a pharmaceutically acceptable carrier.

Provided in another aspect of the present invention is a method for inhibiting PIM kinase activity in a cell, comprising contacting the cell with an effective amount of a compound of Formula I or Formula II. Yet another aspect of the present invention provides a method for treating a condition by modulation of Provirus Integration of Maloney Kinase (PIM kinase) activity comprising administering to a patient in need of such treatment an effective amount of a compound of Formula I or Formula II.

DETAILED DESCRIPTION OF THE INVENTION

In one aspect, the present invention provides compounds of Formula I, or a stereoisomer, tautomer, or pharmaceutically acceptable salt thereof,

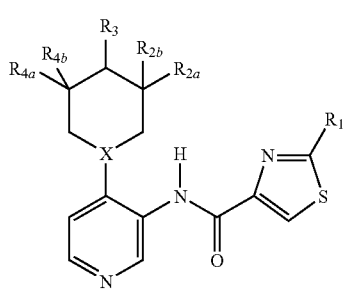

(I)

wherein, $R_1$ is selected from

[structures: substituted phenyl with $R_{21}, R_{22}, R_{23}, R_{24}$, and cyclohexyl]

X represents CH, or N;

$R_{2a}$ is selected from amino, methyl, $CH_2F$, $CF_3$, $C_2H_5$, and H;

$R_{2b}$ is selected from H, and methyl;

$R_3$ is selected from H, OH, $OCH_3$, $CH_3$, F, and Cl;

$R_{4a}$ is selected from amino, methyl, OH, $OCH_3$, $OC_2H_5$, F, $CF_3$, H, and ethyl;

$R_{4b}$ is selected from methyl, H, and F;

$R_{21}$ represents H or F;

$R_{22}$ represents H, Cl, or F;

$R_{23}$ represents F, $OC_2H_5$, $OCH_3$, Cl, H, methyl, OH, or $OCH(CH_3)_2$; and $R_{24}$ represents H or OH.

In another aspect, the present invention provides a compound of Formula II, or a stereoisomer, tautomer, or pharmaceutically acceptable salt thereof,

[Formula II structure]

wherein:

$R_1$ is selected from —NH—CO-alkyl, substituted or unsubstituted cycloalkyl, substituted or unsubstituted heterocycloalkyl, substituted or unsubstituted aryl, and substituted or unsubstituted heteroaryl;

X represents CH or N;

$R_{2a}$ is selected from —H, —OH, alkyl, alkoxy, haloalkyl, aminoalkyl, hydroxyalkyl, halo, amino and bezoate;

$R_{2b}$ is selected from —H and alkyl;

$R_3$ is selected from H, OH, alkyl, alkoxy and halo;

$R_{4a}$ is selected from —OH, alkyl, alkoxy, haloalkyl, aminoalkyl, hydroxyalkyl, halo and amino; and $R_{4b}$ is selected from H, alkyl and halo.

In some aspects, the invention provides compounds of Formula II wherein $R_1$ is selected from substituted or unsubstituted phenyl, substituted or unsubstituted cyclohexyl, and substituted or unsubstituted piperidinyl. In other aspects, the invention provides compounds of Formula II wherein $R_1$ is selected from

[structures: substituted phenyl with $R_{21}, R_{22}, R_{23}, R_{24}$, and cyclohexyl]

wherein:

$R_{21}$ is H or halo;

$R_{22}$ is H or halo;

$R_{23}$ is selected from H, halo, alkyl and alkoxy; and $R_{24}$ is H or OH.

In some embodiments of the invention, $R_{21}$ and $R_{22}$ are independently selected from H or F. In other embodiments, $R_{23}$ is selected from H, Cl, F, —$OC_2H_5$, —$OCH_3$, and —$OCH(CH_3)_2$.

In other embodiments, the invention provides compounds of formula II wherein $R_2$ is selected from H, methyl, ethyl, methoxy, ethoxy, fluoromethyl, trifluoromethyl, aminomethyl and hydroxymethyl.

Yet other embodiments provide compounds of formula II wherein $R_3$ is selected from H, —OH, methyl, methoxy, F and Cl.

In some embodiments, the invention provides compounds of formula II wherein $R_{4a}$ is selected from —OH, methyl, ethyl, trifluoromethyl, methoxy, ethoxy, amino, F and Cl. Other embodiments provide compounds of formula II wherein $R_{4b}$ is selected from methyl and F.

In some presently preferred embodiments, the invention provides a compound of Formula I or Formula II selected from the group consisting of (S)-5-amino-N-(4-(3-aminopiperidin-1-yl)pyridin-3-yl)-2-(2,6-difluorophenyl)thiazole-4-carboxamide, N-(4-((3S,5R)-3-amino-5-methylpiperidin-1-yl)pyridin-3-yl)-2-(2,6-difluorophenyl)thiazole-4-carboxamide, N-(4-((3R,4R,5S)-3-amino-4-hydroxy-5-methyl-piperidin-1-yl)pyridin-3-yl)-2-(2,6-difluorophenyl)thiazole-4-carboxamide, 5-amino-N-(4-((1R,3S)-3-aminocyclohexyl)pyridin-3-yl)-2-(2,6-difluorophenyl)thiazole-4-carboxamide, N-(4-((3S,5R)-3-amino-5-(trifluoromethyl)piperidin-1-yl)pyridin-3-yl)-2-(2,6-difluorophenyl)thiazole-4-carboxamide, N-(4-((3S,5R)-3-amino-5-ethylpiperidin-1-yl)pyridin-3-yl)-2-(2,6-difluorophenyl)thiazole-4-carboxamide, N-(4-((1R,3S,5S)-3-amino-5-methylcyclohexyl)pyridin-3-yl)-2-(2,6-difluoro-4-hydroxyphenyl)thiazole-4-carboxamide, 5-amino-N-(4-(3-amino-4-hydroxycyclohexyl)pyridin-3-yl)-2-(2,6-difluorophenyl)thiazole-4-carboxamide, N-(4-(3-amino-5-(fluoromethyl)piperidin-1-yl)-pyridin-3-yl)-2-(2,6-difluorophenyl)thiazole-4-carboxamide, N-(4-((1R,3S,5S)-3-amino-5-methylcyclohexyl)pyridin-3-yl)-2-(2,6-difluoro-3-methoxyphenyl)thiazole-4-carboxamide, 5-amino-2-(2,6-difluorophenyl)-N-(4-((1R,3S,5S)-3-hydroxy-5-methylcyclohexyl)pyridin-3-yl)thiazole-4-carboxamide, N-(4-((1R,3S,5S)-3-amino-5-methylcyclohexyl)pyridin-3-yl)-2-(2,6-difluorophenyl)thiazole-4-carboxamide, N-(4-(3-amino-4-methylpiperidin-1-yl)pyridin-3-yl)-2-(2,6-difluorophenyl)thiazole-4-carboxamide, N-(4-((1R,3S,5S)-3-amino-5-methylcyclohexyl)pyridin-3-yl)-2-(3-ethoxy-2,6-difluorophenyl)-thiazole-4-carboxamide, or a stereoisomer, tautomer, or pharmaceutically acceptable salt thereof.

In other presently preferred embodiments, the invention provides a compound of Formula I or Formula II selected from the group consisting of (S)-5-amino-N-(4-(3-aminopiperidin-1-yl)pyridin-3-yl)-2-(2,6-difluorophenyl)thiazole-4-carboxamide, N-(4-((3S,5R)-3-amino-5-methylpiperidin-1- yl)pyridin-3-yl)-2-(2,6-difluorophenyl)thiazole-4-carboxamide, N-(4-((3R,4R,5S)-3-amino-4-hydroxy-5-methyl-piperidin-1-yl)pyridin-3-yl)-2-(2,6-difluorophenyl)thiazole-4-carboxamide, 5-amino-N-(4-((1R,3S)-3-aminocyclohexyl)pyridin-3-yl)-2-(2,6-difluorophenyl)thiazole-4-carboxamide, N-(4-((3S,5R)-3-amino-5-(trifluoromethyl)piperidin-1-yl)pyridin-3-yl)-2-(2,6-difluorophenyl)thiazole-4-carboxamide, N-(4-((3S,5R)-3-amino-5-ethylpiperidin-1-yl)pyridin-3-yl)-2-(2,6-difluorophenyl)thiazole-4-carboxamide, N-(4-((1R,3S,5S)-3-amino-5-methylcyclohexyl)pyridin-3-yl)-2-(2,6-difluoro-4-hydroxyphenyl)thiazole-4-carboxamide, 5-amino-N-(4-(3-amino-4-hydroxycyclohexyl)pyridin-3-yl)-2-(2,6-difluorophenyl)thiazole-4-carboxamide, N-(4-(3-amino-5-(fluoromethyl)piperidin-1-yl)-pyridin-3-yl)-2-(2,6-difluorophenyl)thiazole-4-carboxamide, N-(4-((1R,3S,5S)-3-amino-5-methylcyclohexyl)pyridin-3-yl)-2-(2,6-difluoro-3-methoxyphenyl)thiazole-4-carboxamide, 5-amino-2-(2,6-difluorophenyl)-N-(4-((1R,3S,5S)-3-hydroxy-5-methylcyclohexyl)pyridin-3-yl)thiazole-4-carboxamide, N-(4-((1R,3S,5S)-3-amino-5-methylcyclohexyl)pyridin-3-yl)-2-(2,6-difluorophenyl)thiazole-4-carboxamide, or a stereoisomer, tautomer, or pharmaceutically acceptable salt thereof.

Another aspect of the present invention provides a composition comprising a therapeutically effective amount of compound of Formula I or Formula II, or a stereoisomer, tautomer, or pharmaceutically acceptable salt thereof, together with a pharmaceutically acceptable carrier.

Provided in another aspect of the present invention is a method for inhibiting PIM kinase activity in a cell, comprising contacting the cell with an effective amount of a compound of Formula I or Formula II. Yet another aspect of the present invention provides a method for treating a condition by modulation of Provirus Integration of Maloney Kinase (PIM kinase) activity comprising administering to a patient in need of such treatment an effective amount of a compound of Formula I or Formula II.

A preferred embodiment of this aspect of the present invention provides a method for treating a cancer disorder in a patient, comprising administering to the patient a composition comprising an amount of a compound of claim 1 or claim 10 effective to inhibit PIM kinase activity in the patient Other aspect of the present invention provides a compound of any Formula I or Formula II for use as a therapeutic agent. Yet another aspect of the present invention provides the use of any one of the compounds of Formula I or Formula II in the manufacture of a medicament for the treatment of cancer.

DEFINITIONS

"PIM inhibitor" is used herein to refer to a compound that exhibits an $IC_{50}$ with respect to PIM Kinase activity of no more than about 100 μM and more typically not more than about 50 μM, as measured in the PIM depletion assays described herein below.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like.

As used herein, the term "halogen" or "halo" refers to chloro, bromo, fluoro and iodo groups. "Haloalkyl" refers to an alkyl radical substituted with one or more halogen atoms. The term "haloloweralkyl" refers to a lower alkyl radical substituted with one or more halogen atoms. The term "haloalkoxy" refers to an alkoxy radical substituted with one or more halogen atoms. The term "haloloweralkoxy" refers to a loweralkoxy radical substituted with one or more halogen atoms.

"Amino" refers herein to the group —$NH_2$, which may be substituted to form —NRR'. The term "alkylamino" refers herein to the group —NRR' where R and R' are each independently selected from hydrogen or a lower alkyl. The term "arylamino" refers herein to the group —NRR' where R is aryl and R' is hydrogen, a lower alkyl, or an aryl. The term "aralkylamino" refers herein to the group —NRR' where R is a lower aralkyl and R' is hydrogen, a loweralkyl, an aryl, or a loweraralkyl.

The term "alkoxy" refers to RO— wherein R is substituted or unsubstituted alkyl. Representative examples of loweralkoxy groups include methoxy, ethoxy, t-butoxy, trifluoromethoxy and the like.

"Cycloalkyl" refers to a mono- or polycyclic, heterocyclic or carbocyclic alkyl substituent. Typical cycloalkyl substituents have from 3 to 8 backbone (i.e., ring) atoms in which each backbone atom is either carbon or a heteroatom. The term "heterocycloalkyl" or "heterocyclyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperidinyl and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Aryl" refers to optionally substituted monocyclic and polycyclic aromatic groups having from 3 to 14 backbone carbon or hetero atoms, and includes both carbocyclic aryl groups and heterocyclic aryl groups. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms. When used in connection with aryl substituents, the term "polycyclic aryl" refers herein to fused and non-fused cyclic structures in which at least one cyclic structure is aromatic, such as, for example, benzodioxozolo (which has a heterocyclic structure fused to a phenyl group, i.e.,

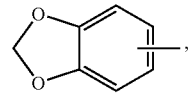

naphthyl, and the like. Exemplary aryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Optionally substituted" or "substituted" refers to the replacement of one or more hydrogen atoms with a monovalent or divalent radical. Suitable substitution groups include, for example, hydroxy, nitro, amino, imino, cyano, halo, thio, sulfonyl, thioamido, amidino, imidino, oxo, oxamidino, methoxamidino, imidino, guanidino, sulfonamido, carboxyl, formyl, loweralkyl, haloloweralkyl, loweralkylamino, haloloweralkylamino, loweralkoxy, haloloweralkoxy, loweralkoxyalkyl, alkylcarbonyl, aminocarbonyl, arylcarbonyl, aralkylcarbonyl, heteroarylcarbonyl, heteroaralkylcarbonyl, alkylthio, aminoalkyl, cyanoalkyl, aryl and the like.

The substitution group can itself be substituted. The group substituted onto the substitution group can be carboxyl, halo; nitro, amino, cyano, hydroxy, loweralkyl, loweralkoxy, aminocarbonyl, —SR, thioamido, —SO$_3$H, —SO$_2$R or cycloalkyl, where R is typically hydrogen, hydroxyl or loweralkyl.

It is understood that the above definitions are not intended to include impermissible substitution patterns (e.g., methyl substituted with five fluoro groups or a halogen atom substituted with another halogen atom). Such impermissible substitution patterns are well known to the skilled artisan.

It will also be apparent to those skilled in the art that the compounds of the invention, including the compounds of compounds of formulas (I) or (II) or their stereoisomers, as well as the pharmaceutically acceptable salts, esters, metabolites and prodrugs of any of them, may be subject to tautomerization and may therefore exist in various tautomeric forms wherein a proton of one atom of a molecule shifts to another atom and the chemical bonds between the atoms of the molecules are consequently rearranged. See, e.g., March, *Advanced Organic Chemistry: Reactions, Mechanisms and Structures*, Fourth Edition, John Wiley & Sons, pages 69-74 (1992). As used herein, the term "tautomer" refers to the compounds produced by the proton shift, and it should be understood that the all tautomeric forms, insofar as they may exist, are included within the invention.

The compounds of the invention, including the compounds of formulas (I) or (II) or their tautomers, as well as the pharmaceutically acceptable salts, esters, metabolites and prodrugs of any of them, may comprise asymmetrically substituted carbon atoms. Such asymmetrically substituted carbon atoms can result in the compounds of the invention existing in enantiomers, diastereomers, and other stereoisomeric forms that may be defined, in terms of absolute stereochemistry, such as in (R)— or (S)— forms. As a result, all such possible isomers, individual stereoisomers in their optically pure forms, mixtures thereof, racemic mixtures (or "racemates"), mixtures of diastereomers, as well as single diastereomers of the compounds of the invention are included in the present invention. The terms "S" and "R" configuration, as used herein, are as defined by the IUPAC 1974 RECOMMENDATIONS FOR SECTION E, FUNDAMENTAL STEREOCHEMISTRY, *Pure Appl. Chem.* 45:13-30 (1976). The terms α and β are employed for ring positions of cyclic compounds. The α-side of the reference plane is that side on which the preferred substituent lies at the lower numbered position. Those substituents lying on the opposite side of the reference plane are assigned β descriptor. It should be noted that this usage differs from that for cyclic stereoparents, in which "α" means "below the plane" and denotes absolute configuration. The terms α and β configuration, as used herein, are as defined by the CHEMICAL ABSTRACTS INDEX GUIDE-APPENDIX IV (1987) paragraph 203.

As used herein, the term "pharmaceutically acceptable salts" refers to the nontoxic acid or alkaline earth metal salts of the compounds of Formulas (I) or (II). These salts can be prepared in situ during the final isolation and purification of the compounds of Formulas (I) or (II), or by separately reacting the base or acid functions with a suitable organic or inorganic acid or base, respectively. Representative salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, pamoate, pectinate, persulfate, 3-phenylproionate, picrate, pivalate, propionate, succinate, sulfate, tartrate, thiocyanate, p-toluenesulfonate and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids which may be employed to form pharmaceutically acceptable acid addition salts include such inorganic acids as hydrochloric acid, sulfuric acid and phosphoric acid and such organic acids as oxalic acid, maleic acid, methanesulfonic acid, succinic acid and citric acid. Basic addition salts can be prepared in situ during the final isolation and purification of the compounds of formula (I), or separately by reacting carboxylic acid moieties with a suitable base such as the hydroxide, carbonate or bicarbonate of a pharmaceutically acceptable metal cation or with ammonia, or an organic primary, secondary or tertiary amine. Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like.

As used herein, the term "pharmaceutically acceptable ester" refers to esters, which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

It will be apparent to those skilled in the art that the compounds of the invention, including the compounds of formulas (I) or (II) or their tautomers, prodrugs and stereoisomers, as well as the pharmaceutically acceptable salts, esters and prodrugs of any of them, may be processed in vivo through metabolism in a human or animal body or cell to produce metabolites. The term "metabolite" as used herein refers to the formula of any derivative produced in a subject after administration of a parent compound. The derivatives may be produced from the parent compound by various biochemical transformations in the subject such as, for example, oxidation, reduction, hydrolysis, or conjugation and include, for example, oxides and demethylated derivatives. The metabolites of a compound of the invention may be identified using routine techniques known in the art. See, e.g., Bertolini, G. et al., *J. Med. Chem.* 40:2011-2016 (1997); Shan, D. et al., *J. Pharm. Sci.* 86(7):765-767; Bagshawe K., *Drug Dev. Res.* 34:220-230 (1995); Bodor, N., *Advances in Drug Res.* 13:224-331 (1984); Bundgaard, H., *Design of Prodrugs* (Elsevier Press 1985); and Larsen, I. K., *Design and Application of Prodrugs, Drug Design and Development* (Krogsgaard-Larsen et al., eds., Harwood Academic Publishers, 1991). It should be understood that individual chemical compounds that are metabolites of the compounds of formulas (I) or (II) or their tautomers, prodrugs and stereoisomers, as well as the pharmaceutically acceptable salts, esters and prodrugs of any of them, are included within the invention.

The term "cancer" refers to cancer diseases that can be beneficially treated by the inhibition of Pim kinase, including, for example, solid cancers, such as carcinomas (e.g., of the lungs, pancreas, thyroid, ovarian, bladder, breast, prostate, or colon), melanomas, myeloid disorders (e.g., myeloid leukemia, multiple myeloma and erythroleukemia), adenomas (e.g., villous colon adenoma) and sarcomas (e.g., osteosarcoma).

Synthetic Methods

The compounds of the invention can be obtained through procedures known to the skilled in the art. For example, as shown in Scheme 1, 4-chloro, 3-nitro pyridine can be reacted with a nucleophile yielding after nitro reduction a 4-substituted 3-amino pyridine I. The substituted amino pyridines I can be acylated with thiazolecarboxylic acids with the aid of coupling agents, or with acid halides or acid anhydrides yielding 3, 4 disubstituted pyridines II. If the 2 position R group of the thiazole is bromo, triflate or iodo, further modification to incorporate a variety of substituents at this position can be realized by metal mediated carbon-carbon bond forming reactions.

Scheme 1.

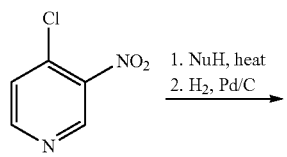

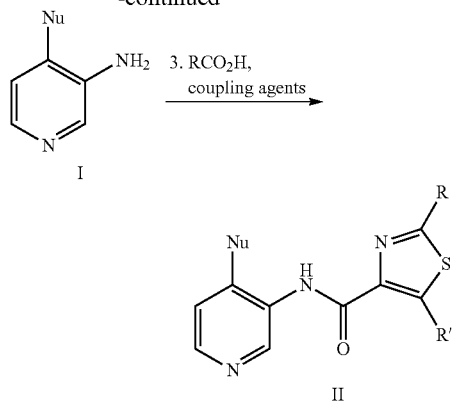

R' = H or NH2

The reaction of 4-chloro-3-nitropyridine with nucleophiles as depicted in Scheme 1 is not limited to nitrogen based nucleophiles; carbon-carbon bonds can be formed as well with the net addition of carbon nucleophiles. As shown in Scheme 2, cyclohexanediones can be converted via monotriflates to the corresponding cyclohexenoneboronate esters which can undergo palladium mediated carbon-carbon bond formation with 4-chloro, 3-nitro pyridine to yield nitropyridine substituted cyclohexenones III. Reduction of the enone functionality can yield a cyclohexenol IV which upon alcohol protection, nitro and alkene reduction, amide coupling and deprotection can yield cyclohexanol amides V. Cyclohexenol IV can also undergo Mitsunobo reaction with phthalimide to yield a protected aminocyclohexene V. Following nitro and alkene reduction, phthalimide protected aminocyclohexyl pyridyl aniline VIIa can undergo amide coupling and deprotection, to yield aminocyclohexane amides VIII. The corresponding Boc protected aminocyclohexane pyridyl aniline VIIb can also be prepared from cyclohexenol IV in the following manner: alcohol protection, alkene and nitro reduction, pyridyl amine Cbz protection, silyl ether deprotection, dess-martin oxidation to the cyclohexanone, reductive amination with benzylamine, Cbz and benzyl deprotection and primary aliphatic amine Boc protection. In the amide products V and VIII, if R2 is halo or triflate, the amides IV and VIII can be further modified by standard modifications to introduce substituted aryls, alkyls and heteroaryls at R2. For example, if R2 is Br, by reaction with boronic acids or organometallic reagents, or conversion to the corresponding boronate ester and reaction with aryl/heteroaryl halides or triflates, a variety of R2 modifications are possible.

Scheme 2.

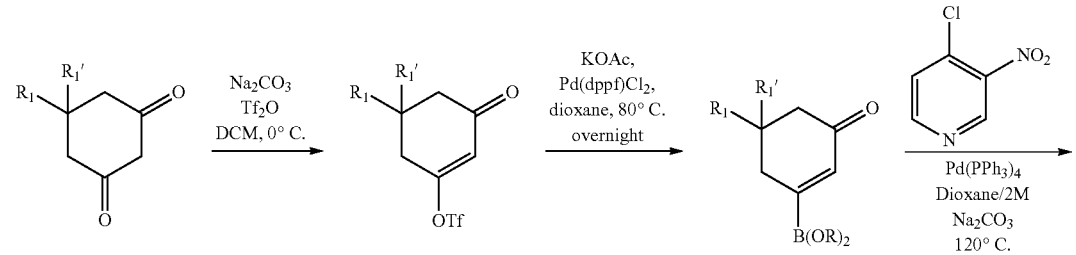

-continued

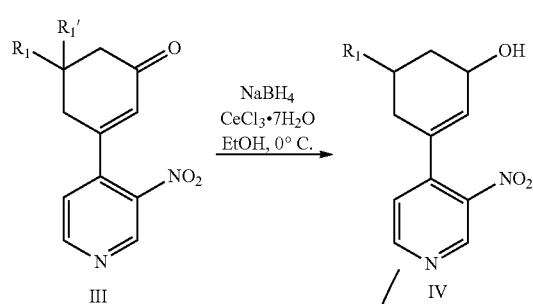
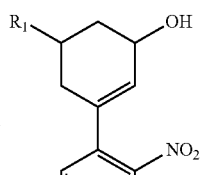
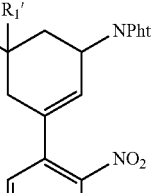
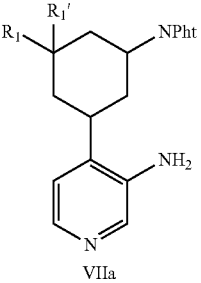

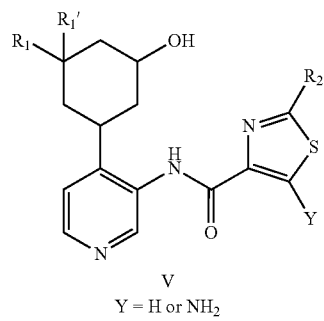
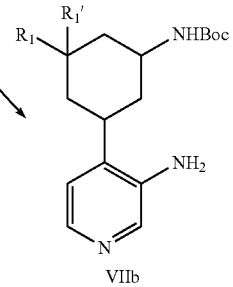
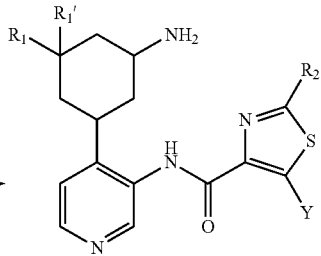

Thiazole amides with substituted cyclohexyl groups can be obtained by modification of nitropyridyl cyclohexenol IV. As shown in Scheme 3, cyclohexenol IV can be dehydrated yielding a cyclohexadiene which upon epoxidation (via bromohydrin formation and HBr elimination or from mCPBA directly) and azide epoxide opening yields cyclohexenyl azido alcohol IX. Cyclohexenyl azido alcohol IX can be converted to the trans protected amino hydroxy aniline Xa by azide reduction, alcohol protection and alkene and nitro reduction. Alternatively, the cyclohexenyl azido alcohol IX can be converted to the protected cis amino hydroxy aniline Xb by azide reduction and Boc protection, alcohol mesylation and intramolecular cyclization to the cis cyclic carbamate, followed by Boc protection and alkene and nitro reduction. The resulting cyclohexylpyridyl anilines Xa and Xb can be converted to the corresponding thiazole amides XIa and XIb by amide coupling, acetate or cyclic carbamate cleavage and Boc deprotection. If $R_2$ is halo or triflate, the amides XIa and XIb and XII can be further modified by standard modifications to introduce substituted aryls, alkyls and heteroaryls at $R_2$ after amide bond formation and prior to full deprotection. For example, if $R_2$ is Br, by reaction with boronic acids or organometallic reagents, or conversion to the corresponding boronate ester and reaction with aryl/heteroaryl halides or triflates, a variety of $R_2$ modifications are possible.

Scheme 3.

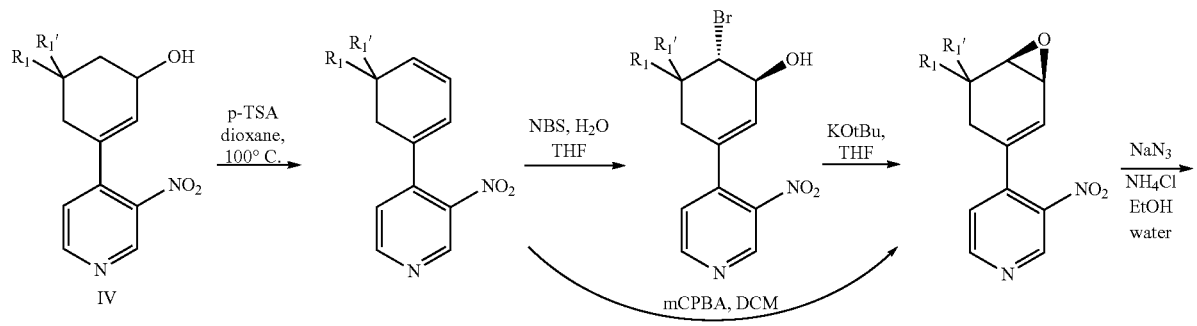

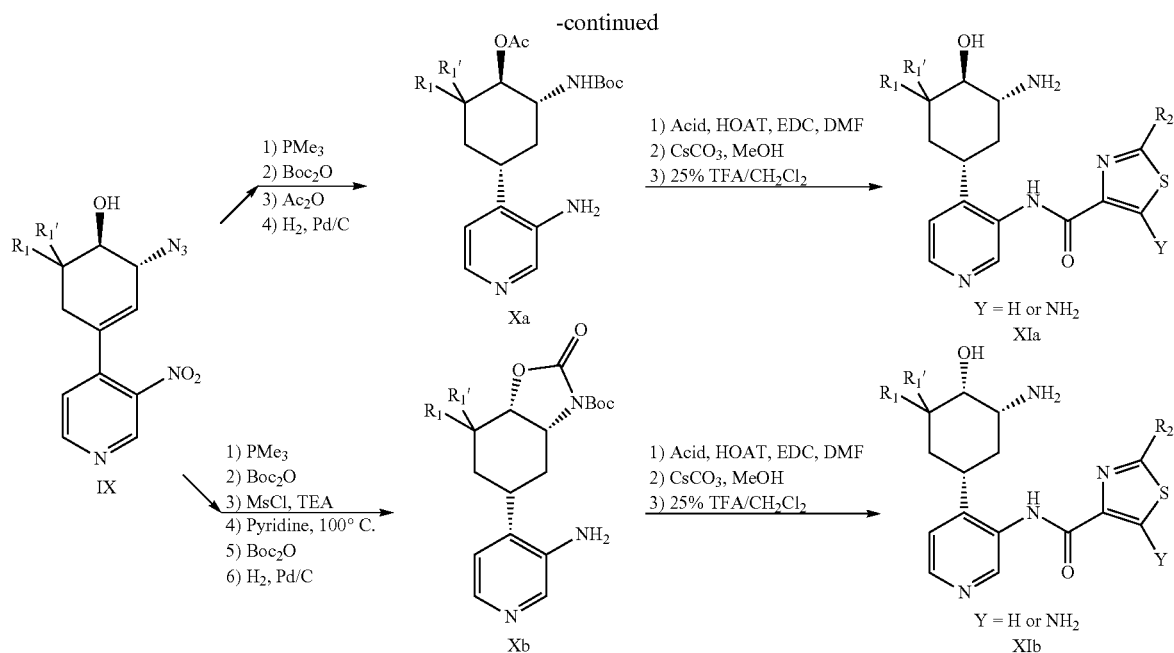

Substituted 3-aminopiperidines can be prepared and modified to yield substituted 3-aminopiperidinyl thiazole amides XII as depicted in Scheme 4. Reaction of crotyl boronate esters with SerOBn aldehyde followed by cyclic carbamate formation, alkene oxidative cleavage and reduction yields hydroxyl compound XIII. Benzyl deprotection followed by bistosylation and reaction with p-methoxybenzylamine, and amine deprotection yields piperidine XIV. By use of chiral boronate esters, and different L and D serine derived aldehydes, all possible diastereomers of the resulting trisubstituted 5-alkyl, 4-hydroxy, 3-aminopiperidine can be obtained. Reaction of substituted piperidine XIV with 4-chloro-3-nitropyridine, followed by carbamate protection, nitro reduction, amide coupling, cyclic carbamate opening and deprotection yields trisubstituted 5-methyl, 4-hydroxy, 3-aminopiperidinyl thiazole amides XII. If $R_2$ is halo or triflate, the amide XII can be further modified by standard modifications to introduce substituted aryls, alkyls and heteroaryls at $R_2$ after amide bond formation and prior to full deprotection. For example, if $R_2$ is Br, by reaction with boronic acids or organometallic reagents, or conversion to the corresponding boronate ester and reaction with aryl/heteroaryl halides or triflates, a variety of R2 modifications are possible.

Scheme 4.

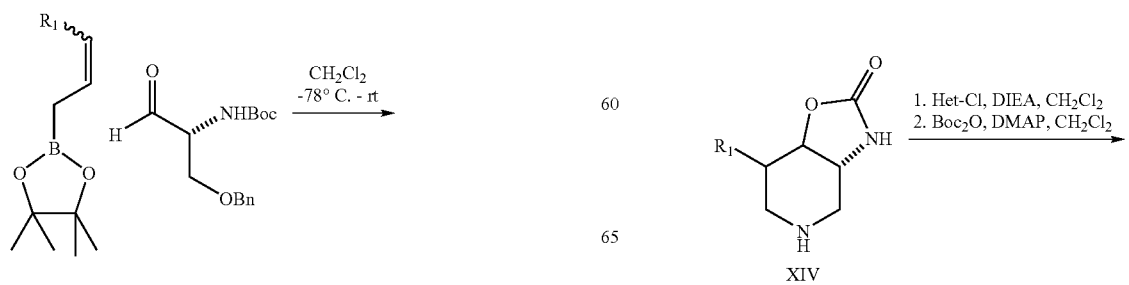

-continued

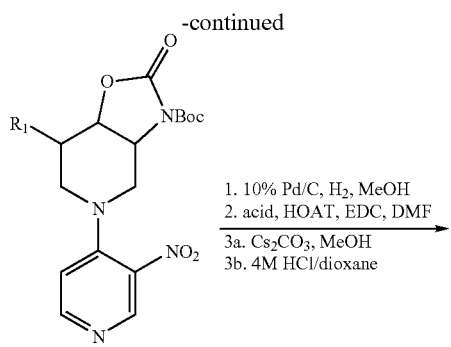

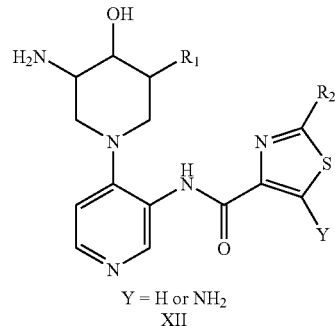

Y = H or NH$_2$
XII

The compounds of the invention are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey (1991), incorporated herein by reference.

Effective amounts of the compounds of the invention generally include any amount sufficient to detectably inhibit Pim activity by any of the assays described herein, by other Pim kinase activity assays known to those having ordinary skill in the art or by detecting an inhibition or alleviation of symptoms of cancer.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

For purposes of the present invention, a therapeutically effective dose will generally be a total daily dose administered to a host in single or divided doses may be in amounts, for example, of from 0.001 to 1000 mg/kg body weight daily and more preferred from 1.0 to 30 mg/kg body weight daily. Dosage unit compositions may contain such amounts of submultiples thereof to make up the daily dose.

The compounds of the present invention may be administered orally, parenterally, sublingually, by aerosolization or inhalation spray, rectally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols, which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art. See, for example, Prescott, Ed., *Methods in Cell Biology*, Volume XIV, Academic Press, New York, N.W., p. 33 et seq. (1976).

While the compounds of the invention can be administered as the sole active pharmaceutical agent, they can also be used in combination with one or more other agents used in the treatment of cancer. The compounds of the present invention are also useful in combination with known therapeutic agents and anti-cancer agents, and combinations of the presently disclosed compounds with other anti-cancer or chemotherapeutic agents are within the scope of the invention. Examples of such agents can be found in *Cancer Principles and Practice of Oncology*, V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Such anti-cancer agents include, but are not limited to, the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, inhibitors of cell proliferation and survival signaling, apoptosis inducing agents and agents that interfere with cell cycle checkpoints. The compounds of the invention are also useful when co-administered with radiation therapy.

Therefore, in one embodiment of the invention, the compounds of the invention are also used in combination with known anticancer agents including, for example, estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors.

In certain presently preferred embodiments of the invention, representative agents useful in combination with the compounds of the invention for the treatment of cancer include, for example, irinotecan, topotecan, gemcitabine, 5-fluorouracil, leucovorin carboplatin, cisplatin, taxanes, tezacitabine, cyclophosphamide, vinca alkaloids, imatinib (Gleevec), anthracyclines, rituximab, trastuzumab, as well as other cancer chemotherapeutic agents.

The above compounds to be employed in combination with the compounds of the invention will be used in therapeutic amounts as indicated in the *Physicians' Desk Reference* (PDR) 47th Edition (1993), which is incorporated herein by reference, or such therapeutically useful amounts as would be known to one of ordinary skill in the art.

The compounds of the invention and the other anticancer agents can be administered at the recommended maximum clinical dosage or at lower doses. Dosage levels of the active compounds in the compositions of the invention may be varied so as to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions, which are given at the same time or different times, or the therapeutic agents, can be given as a single composition.

The present invention will be understood more readily by reference to the following examples, which are provided by way of illustration and are not intended to be limiting of the present invention.

Representative side chains for use in the compounds of the following examples may generally be prepared in accordance with the following procedures:

EXAMPLES

Referring to the examples that follow, compounds of the preferred embodiments were synthesized using the methods described herein, or other methods, which are known in the art.

The compounds and/or intermediates were characterized by high performance liquid chromatography (HPLC) using a Waters Millenium chromatography system with a 2695 Separation Module (Milford, Mass.). The analytical columns were reversed phase Phenomenex Luna C18-5μ, 4.6×50 mm, from Alltech (Deerfield, Ill.). A gradient elution was used (flow 2.5 mL/min), typically starting with 5% acetonitrile/95% water and progressing to 100% acetonitrile over a period of 10 minutes. All solvents contained 0.1% trifluoroacetic acid (TFA). Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well-known iodine vapor and other various staining techniques.

Mass spectrometric analysis was performed on one of three LCMS instruments: a Waters System (Alliance HT HPLC and a Micromass ZQ mass spectrometer; Column: Eclipse XDB-C18, 2.1×50 mm; gradient: 5-95% (or 35-95%, or 65-95% or 95-95%) acetonitrile in water with 0.05% TFA over a 4 min period; flow rate 0.8 mL/min; molecular weight range 200-1500; cone Voltage 20 V; column temperature 40° C.), another Waters System (ACQUITY UPLC system and a ZQ 2000 system; Column: ACQUITY UPLC HSS-C18, 1.8 um, 2.1×50 mm; gradient: 5-95% (or 35-95%, or 65-95% or 95-95%) acetonitrile in water with 0.05% TFA over a 1.3 min period; flow rate 1.2 mL/min; molecular weight range 150-850; cone Voltage 20 V; column temperature 50° C.) or a Hewlett Packard System (Series 1100 HPLC; Column: Eclipse XDB-C18, 2.1×50 mm; gradient: 5-95% acetonitrile in water with 0.05% TFA over a 4 min period; flow rate 0.8 mL/min; molecular weight range 150-850; cone Voltage 50 V; column temperature 30° C.). All masses were reported as those of the protonated parent ions.

GCMS analysis was performed on a Hewlett Packard instrument (HP6890 Series gas chromatograph with a Mass Selective Detector 5973; injector volume: 1 μL; initial column temperature: 50° C.; final column temperature: 250° C.; ramp time: 20 minutes; gas flow rate: 1 mL/min; column: 5% phenyl methyl siloxane, Model No. HP 190915-443, dimensions: 30.0 m×25 m×0.25 m).

Nuclear magnetic resonance (NMR) analysis can be performed with a Varian 300 or 400 MHz NMR (Palo Alto, Calif.). The spectral reference can either be TMS or the known chemical shift of the solvent.

The purity of some of the compounds is assessed by elemental analysis (Desert Analytics, Tucson, Ariz.).

Melting points are determined on a Laboratory Devices Mel-Temp apparatus (Holliston, Mass.).

Preparative separations are carried out using a Flash 40 chromatography system and KP-Sil, 60A (Biotage, Charlottesville, Va.), or by flash column chromatography using silica gel (230-400 mesh) packing material, or by HPLC using a Waters 2767 Sample Manager, C-18 reversed phase column, 30×50 mm, flow 75 mL/min. Typical solvents employed for the Flash 40 Biotage system and flash column chromatography are dichloromethane, methanol, ethyl acetate, hexane, acetone, aqueous ammonia (or ammonium hydroxide), and triethyl amine. Typical solvents employed for the reverse phase HPLC are varying concentrations of acetonitrile and water with 0.1% trifluoroacetic acid.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

The examples below as well as throughout the application, the following abbreviations have the following meanings. If not defined, the terms have their generally accepted meanings.

ABBREVIATIONS

| | |
|---|---|
| Boc₂O | di-tert-butyl dicarbonate |
| DAST | (Diethylamino)sulfurtrifluoride |
| DCM | Dichloromethane |
| DIEA | diisopropylethylamine |
| DtBAD | Di-tert-butyl azodicarboxylate |
| DMA | dimethylacetamide |
| DMAP | 4-dimethylaminopyridine |
| DME | 1,2-dimethoxyethane |
| DMF | N,N-dimethylformamide |
| DPPF | 1,1'-bis(diphenylphosphino)ferrocene |
| EDC | 1-(3-dimethylaminopropyl)-3-ethylcarbodiimide hydrochloride |
| EtOAc | ethyl acetate |
| EtOH | Ethanol |
| HOAT | Hydroxyazabenzotriazole |
| MeCN | acetonitrile |
| MeOH | methanol |
| Na₂CO₃ | sodium carbonate |
| NaHCO₃ | sodium bicarbonate |
| NBS | N-bromosuccinimide |
| NMP | N-methyl-2-pyrrolidone |
| Pd₂(dba)₃ | Tris(dibenzylideneacetone)dipalladium(0) |
| Pd(PPh₃)₄ | Tetrakis(triphenylphospine)palladium(0) |
| Pd(dppf)Cl₂-DCM | Dichloro-(1,2-bis(diphenylphosphino)ethan)-Palladium(II)-dichloromothethane adduct |
| RT or rt | room temperature |
| TDMSCl | Tert-butyldimethylsilylchloride |
| TEA | triethylamine |
| THF | tetrahydrofuran |
| Tf2O | Triflic anhydride |

METHOD 1

Synthesis of 3-nitro-4-(piperidin-1-yl)pyridine

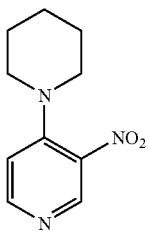

A solution of 4-chloro-3-nitropyridine (1.0 equiv.) and piperidine (2.0 equiv.) in ethanol, at a concentration of 0.5 M, was stirred at rt for 48 hours at which time the ethanol was removed in vacuo. The residue was partitioned between EtOAc (300 mL) and Na₂CO₃ (sat.) (75 mL), was washed further with H₂O (50 mL), NaCl$_{(sat.)}$ (50 mL), was dried over MgSO₄, was filtered and the volatiles were removed in vacuo yielding 3-nitro-4-(piperidin-1-yl)pyridine (95%). LCMS (m/z): 207.7 (MH⁺); LC R$_t$=1.60 min. ¹H NMR (CDCl₃): δ 8.80 (s, 1H), 8.31 (d, J=5.7, 1H), 6.84 (d, J=6.3, 1H), 3.18-3.21 (m, 4H), 1.64-1.78 (m, 6H).

Synthesis of (S)-tert-butyl 1-(3-nitropyridin-4-yl) piperidin-3-ylcarbamate

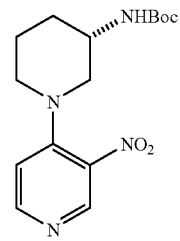

Method 1 was followed using 1 eq each of 4-chloro-3-nitropyridine, (S)-3-N-Boc-amino piperidine and diisopropylethylamine yielding (S)-tert-butyl 1-(3-nitropyridin-4-yl) piperidin-3-ylcarbamate, (99%). LCMS (m/z): 323.1 (MH⁺); LC R$_t$=2.13 min.

Synthesis of trans(+/−)-Benzyl 3-(tert-butoxycarbonylamino)-4-hydroxypiperidine-1-carboxylate

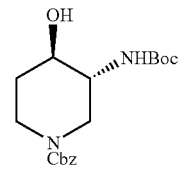

Synthesis of trans(+/−)-Benzyl 4-(tert-butoxycarbonylamino)-3-hydroxypiperidine-1-carboxylate

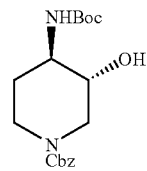

A solution of (+/−)benzyl 7-oxa-3-azabicyclo[4.1.0]heptane-3-carboxylate (1.0 equiv.) in saturated ammonium hydroxide aqueous solution and ethanol (1:1, 0.05 M solution) in a sealed steel bomb was heated to 70° C. for 5 h. After all volatile materials were removed by N₂ gas stream, ethyl acetate and water were added for work-up. The crude regioisomeric mixture, benzyl 3-amino-4-hydroxypiperidine-1-carboxylate and benzyl 4-amino-3-hydroxypiperidine-1-carboxylate was reacted with Boc₂O (1.0 equiv.) and triethylamine (1.0 equiv.) in dichloromethane (0.1 M solution). After stirred for 2 h at room temperature, the reaction mixture was extracted with dichloromethane. The polar (+/−)-benzyl 3-(tert-butoxycarbonylamino)-4-hydroxypiperidine-1-carboxylate and nonpolar (+/−)-benzyl 4-(tert-butoxycarbonylamino)-3-hydroxypiperidine-1-carboxylate were obtained by flash column chromatography (20% to 40% EtOAc in hexanes, 28%, 51% each). LCMS (m/z): 351.1 (MH$^+$), R$_t$=0.81 min, LCMS (m/z): 351.1 (MH$^+$), R$_t$=0.83 min. The enantiomerically pure (3S,4S)-benzyl 3-(tert-butoxycarbonylamino)-4-hydroxypiperidine-1-carboxylate and (3R,4R)-benzyl 3-(tert-butoxycarbonylamino)-4-hydroxypiperidine-1-carboxylate were resolved by chiral HPLC (For analysis R$_t$=6.8 min and 9.1 min respectively; n-heptane:ethanol=70:30 (v:v), Chiralpak AD-H prep 250× 4.6 mm at 1 mL/min. For preparative separation, n-heptane: ethanol=80:20 (v:v), Chiralpak AS 50×500 mm. at 90 mL/min).

METHOD 2

Synthesis of 4-(piperidin-1-yl)pyridin-3-amine

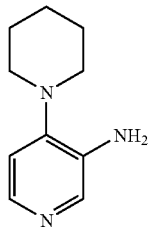

To a solution of 3-nitro-4-(piperidin-1-yl)pyridine (1.0 equiv.) in ethanol, at a concentration of 0.1 M, was added 10% palladium on carbon (0.1 eq.). The resultant heterogeneous solution was put under an atmosphere of hydrogen and was stirred for 15 hours. At this time the mixture was filtered through a pad of celite eluting with methanol. The volatiles were removed in vacuo yielding 4-(piperidin-1-yl)pyridin-3-amine (93%) as an oil. LCMS (m/z): 178.0 (MH$^+$); LC R$_t$=1.68 min. $^1$H NMR (CDCl$_3$): δ 8.01 (s, 1H), 7.96 (d, J=5.4, 1H), 6.78 (d, J=5.1, 1H), 3.64-3.74 (m, 2H), 2.86-2.94 (m, 4H), 1.66-1.78 (m, 4H), 1.58-1.64 (m, 2H).

Synthesis of (S)-tert-butyl 1-(3-aminopyridin-4-yl)piperidin-3-ylcarbamate

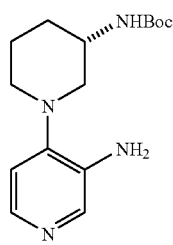

Following Method 2, (S)-tert-butyl 1-(3-nitropyridin-4-yl)piperidin-3-ylcarbamate was reduced yielding (S)-tert-butyl 1-(3-aminopyridin-4-yl)piperidin-3-ylcarbamate, (78%). LCMS (m/z): 293.1 (MH$^+$); LC R$_t$=2.08 min.

Synthesis of (3R,4R)-benzyl 3-(tert-butoxycarbonylamino)-4-(tert-butyldimethylsilyloxy)piperidine-1-carboxylate

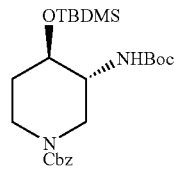

To a solution of (3R,4R)-benzyl 3-(tert-butoxycarbonylamino)-4-hydroxypiperidine-1-carboxylate (1.0 equiv.) in dichloromethane (0.1 M solution) was added imidazole (1.1 equiv.), DMAP (0.1 equiv.), and TBDMSCl (1.1 equiv.) sequentially. The reaction mixture was stirred at room temperature for 20 h. After worked up with dichloromethane, the crude material was purified by silica column chromatography (10% to 20% EtOAc in hexanes) yielding (3R,4R)-benzyl 3-(tert-butoxycarbonylamino)-4-(tert-butyldimethylsilyloxy)piperidine-1-carboxylate (76%). LCMS (m/z): 365.2 [(M-Boc)H$^+$]; LC R$_t$=6.05 min.

Synthesis of (3S,4S)-benzyl 3-(tert-butoxycarbonylamino)-4-(tert-butyldimethylsilyloxy)piperidine-1-carboxylate

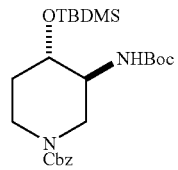

To a solution of (3S,SR)-benzyl 3-(tert-butoxycarbonylamino)-4-hydroxypiperidine-1-carboxylate (1.0 equiv.) in dichloromethane (0.1 M solution) was added imidazole (1.1 equiv.), DMAP (0.1 equiv.), and TBDMSCl (1.1 equiv.) sequentially The reaction mixture was stirred at room temperature for 20 h. After worked up with dichloromethane, the crude material was purified by silica column chromatography (10% to 20% EtOAc in hexanes) yielding (3S,4S)-benzyl 3-(tert-butoxycarbonylamino)-4-(tert-butyldimethylsilyloxy)piperidine-1-carboxylate. LCMS (m/z): 365.2 [(M-Boc)H$^+$]; LC R$_t$=6.05 min.

Synthesis of (3R,4R)-Benzyl 3-(tert-butoxycarbonylamino)-4-fluoropiperidine-1-carboxylate and (3S,4S)-Benzyl 3-(tert-butoxycarbonylamino)-4-fluoropiperidine-1-carboxylate

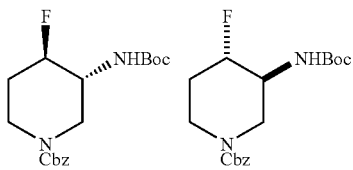

To a solution of (+/−)-benzyl 3-(tert-butoxycarbonylamino)-4-hydroxypiperidine-1-carboxylate (1.0 equiv.) in dichloromethane (0.3 M solution) was added DAST at −78° C. The reaction mixture was slowly warmed up to room temperature for 15 h. After quenched with saturated sodium bicarbonate aqueous solution, ethyl acetate and water were added for work-up. The (+/−)-benzyl 3-(tert-butoxycarbonylamino)-4-fluoropiperidine-1-carboxylate was obtained by silica column chromatography (30% EtOAc in hexanes, 40%). LCMS (m/z): 253.1[(M-Boc)H$^+$]; LC R$_t$=4.08 min. The enantiomerically pure (3R,4R)-benzyl 3-(tert-butoxycarbonylamino)-4-fluoropiperidine-1-carboxy late and (3S, 4S)-benzyl 3-(tert-butoxycarbonylamino)-4-fluoropiperidine-1-carboxylate were resolved by chiral HPLC (for analysis: R$_t$=9.4 min and 12.6 min respectively; n-heptane:isopropanol=90:10 (v:v), Chiralpak AS 250×4.6 mm at 1 mL/min. For preparative separation, n-heptane:isopropanol=90:10 (v:v), Chiralpak AS 50×500 mm. at 90 mL/min).

Synthesis of tert-butyl(3R,4R)-4-fluoropiperidin-3-ylcarbamate

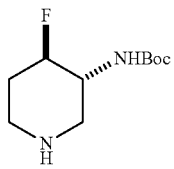

Method 2 was followed using (3R,4R)-benzyl 3-(tert-butoxycarbonylamino)-4-fluoropiperidine-1-carboxylate (1.0 equiv.) yielding crude tert-butyl (3R,4R)-4-fluoropiperidin-3-ylcarbamate, (93%). LCMS (m/z): 219.2 (MH$^+$), LC R$_t$=0.45 min.

Synthesis of tert-butyl(3S,4S)-4-fluoropiperidin-3-ylcarbamate

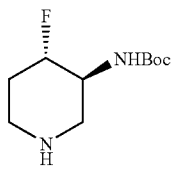

Method 2 was followed using (3S,4S)-benzyl 3-(tert-butoxycarbonylamino)-4-fluoropiperidine-1-carboxylate (1.0 equiv.) yielding crude (+/−)-tert-butyl 4-fluoropiperidin-3-ylcarbamate, (93%). LCMS (m/z): 219.2 (MH$^+$), LC R$_t$=0.45 min.

Synthesis of tert-butyl(3R,4R)-4-(tert-butyldimethylsilyloxy)piperidin-3-ylcarbamate

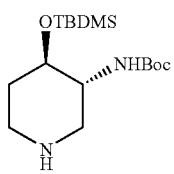

Method 2 was followed using (3R,4R)-benzyl 3-(tert-butoxycarbonylamino)-4-(tert-butyldimethylsilyloxy)piperidine-1-carboxylate (1.0 equiv.) yielding crude tert-butyl(3R,4R)-4-(tert-butyldimethylsilyloxy)piperidin-3-ylcarbamate, (>99%). LCMS (m/z): 331.3 (MH$^+$).

Synthesis of tert-butyl(3R,4R)-4-(tert-butyldimethylsilyloxy)piperidin-3-ylcarbamate

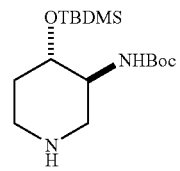

Method 2 was followed using (3S,4S)-benzyl 3-(tert-butoxycarbonylamino)-4-(tert-butyldimethylsilyloxy)piperidine-1-carboxylate (1.0 equiv.) yielding crude tert-butyl(3S,4S)-4-(tert-butyldimethylsilyloxy)piperidin-3-ylcarbamate, (>99%). LCMS (m/z): 331.3 (MH$^+$).

Synthesis of tert-butyl(3R,4R)-4-(tert-butyldimethylsilyloxy)-1-(3-nitropyridin-4-yl)piperidin-3-ylcarbamate

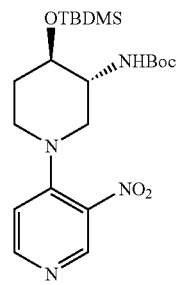

Method 1 was followed using 1 eq each of 4-chloro-3-nitropyridine, tert-butyl (3R,4R)-4-(tert-butyldimethylsilyloxy)piperidin-3-ylcarbamate and triethylamine in DMF yielding tert-butyl(3R,4R)-4-(tert-butyldimethylsilyloxy)-1-(3-nitropyridin-4-yl)piperidin-3-ylcarbamate, (98%). LCMS (m/z): 453.3 (MH$^+$); LC R$_t$=4.01 min.

Synthesis of tert-butyl(3S,4S)-4-(tert-butyldimethylsilyloxy)-1-(3-nitropyridin-4-yl)piperidin-3-ylcarbamate

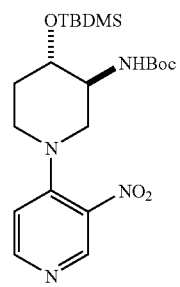

Method 1 was followed using 1 eq each of 4-chloro-3-nitropyridine, tert-butyl (3S,4S)-4-(tert-butyldimethylsilyloxy)piperidin-3-ylcarbamate and triethylamine in DMF yielding tert-butyl(3S,4S)-4-(tert-butyldimethylsilyloxy)-1-(3-nitropyridin-4-yl)piperidin-3-ylcarbamate, (98%). LCMS (m/z): 453.3 (MH$^+$); LC R$_t$=4.01 min.

Synthesis of tert-butyl(3R,4R)-4-fluoro-1-(3-nitropyridin-4-yl)piperidin-3-ylcarbamate

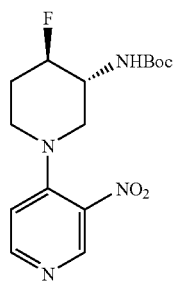

Method 1 of Example 1 was followed using 1 eq each of 4-chloro-3-nitropyridine, tert-butyl(3R,4R)-4-fluoropiperidin-3-ylcarbamate and triethylamine in ethanol yielding tert-butyl(3R,4R)-4-fluoro-1-(3-nitropyridin-4-yl)piperidin-3-ylcarbamate, (91%). LCMS (m/z): 341.0 (MH$^+$); LC R$_t$=2.37 min.

Synthesis of tert-butyl(3S,4S)-4-fluoro-1-(3-nitropyridin-4-yl)piperidin-3-ylcarbamate

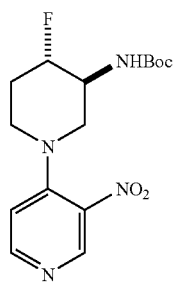

Method 1 of Example 1 was followed using 1 eq each of 4-chloro-3-nitropyridine, tert-butyl(3S,4S)-4-fluoropiperidin-3-ylcarbamate and triethylamine in ethanol yielding tert-butyl(3S,4S)-4-fluoro-1-(3-nitropyridin-4-yl)piperidin-3-ylcarbamate, (91%). LCMS (m/z): 341.0 (MH$^+$); LC R$_t$=2.37 min.

Synthesis of tert-butyl(3R,4R)-1-(3-aminopyridin-4-yl)-4-(tert-butyldimethylsilyloxy)piperidin-3-ylcarbamate

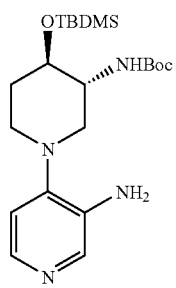

Following method 2, tert-butyl(3R,4R)-4-(tert-butyldimethylsilyloxy)-1-(3-nitropyridin-4-yl)piperidin-3-ylcarbamate in ethanol and ethyl acetate (1:1, 0.1 M solution) was reduced yielding tert-butyl(3R,4R)-1-(3-aminopyridin-4-yl)-4-(tert-butyldimethylsilyloxy)piperidin-3-ylcarbamate, (>99%). LCMS (m/z): 423.2 (MH$^+$); LC R$_t$=3.78 min.

Synthesis of tert-butyl(3S,4S)-1-(3-aminopyridin-4-yl)-4-(tert-butyldimethylsilyloxy)piperidin-3-ylcarbamate

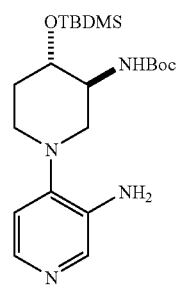

Following method 2, tert-butyl(3R,4R)-4-(tert-butyldimethylsilyloxy)-1-(3-nitropyridin-4-yl)piperidin-3-ylcarbamate in ethanol and ethyl acetate (1:1, 0.1 M solution) was reduced yielding tert-butyl(3R,4R)-1-(3-aminopyridin-4-yl)-4-(tert-butyldimethylsilyloxy)piperidin-3-ylcarbamate, (>99%). LCMS (m/z): 423.2 (MH$^+$); LC R$_t$=3.78 min.

Synthesis of tert-butyl(3R,4R)-1-(3-aminopyridin-4-yl)-4-fluoropiperidin-3-ylcarbamate

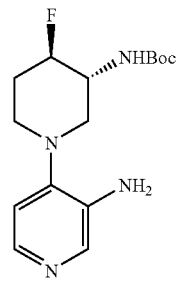

Following method 2, tert-butyl(3R,4R)-4-fluoro-1-(3-nitropyridin-4-yl)piperidin-3-ylcarbamate in ethanol and ethyl acetate (1:1, 0.1 M solution) was reduced yielding tert-butyl(3R,4R)-1-(3-aminopyridin-4-yl)-4-fluoropiperidin-3-ylcarbamate, (>99%). LCMS (m/z): 311.2 (MH$^+$); LC R$_t$=2.14 min.

Synthesis of tert-butyl(3S,4S)-1-(3-aminopyridin-4-yl)-4-fluoropiperidin-3-ylcarbamate

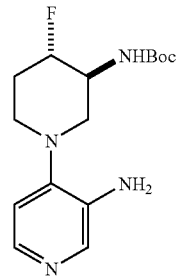

Following method 2, tert-butyl(3S,4S)-4-fluoro-1-(3-nitropyridin-4-yl)piperidin-3-ylcarbamate in ethanol and ethyl acetate (1:1, 0.1 M solution) was reduced yielding tert-butyl (3R,4R)-1-(3-aminopyridin-4-yl)-4-fluoropiperidin-3-ylcarbamate, (>99%). LCMS (m/z): 311.2 (MH$^+$); LC R$_f$=2.14 min.

Synthesis of tert-butyl(3S,5R)-5-(tert-butyldimethylsilyloxy)piperidin-3-ylcarbamate

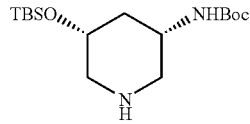

tert-Butyl(3S,5R)-5-(tert-butyldimethylsilyloxy)piperidin-3-ylcarbamate was prepared according to the patent procedure as described by Y, Zhou; WO2005028467.

Synthesis of tert-butyl(3S,5R)-5-(tert-butyldimethylsilyloxy)-1-(3-nitropyridin-4-yl)piperidin-3-ylcarbamate

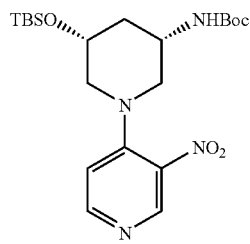

Method 1 was followed was followed using tert-Butyl(3S,5R)-5-(tert-butyldimethylsilyloxy)piperidin-3-ylcarbamate, yielding tert-butyl(3S,5R)-5-(tert-butyldimethylsilyloxy)-1-(3-nitropyridin-4-yl)piperidin-3-ylcarbamate. LC/MS (m/z): 453.2 (MH$^+$).

Synthesis of tert-butyl(3S,5R)-1-(3-aminopyridin-4-yl)-5-(tert-butyldimethylsilyloxy)piperidin-3-ylcarbamate

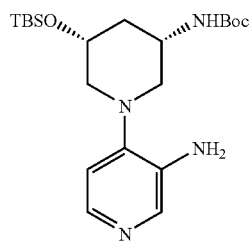

Method 2 was followed using tert-butyl(3S,5R)-5-(tert-butyldimethylsilyloxy)-1-(3-nitropyridin-4-yl)piperidin-3-ylcarbamate, yielding tert-butyl (3S,5R)-1-(3-aminopyridin-4-yl)-5-(tert-butyldimethylsilyloxy)piperidin-3-ylcarbamate. LC/MS (m/z): 423.2 (MH$^+$).

Synthesis of trans(+/−)-benzyl 3-(bis(tert-butoxycarbonyl)amino)-4-hydroxypiperidine-1-carboxylate

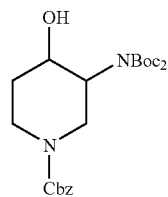

To a solution of trans(+/−)-benzyl 3-(tert-butoxycarbonylamino)-4-hydroxypiperidine-1-carboxylate (1.0 equiv.) in DCM and CH$_3$CN (1:1, 0.14 M) was added BOC$_2$O (1.0 equiv.), triethylamine (1.5 equiv.), and DMAP (catalytic amount). The reaction was stirred at room temperature for 15 h, upon which time the solution was concentrated and purified via silica gel column chromatography eluting with EtOAc and hexanes (1:6) to give the desired product as a white foam. LCMS (m/z): 451.1 (MH$^+$).

Synthesis of trans(+/−)-benzyl 3-(bis(tert-butoxycarbonyl)amino)-4-methoxypiperidine-1-carboxylate

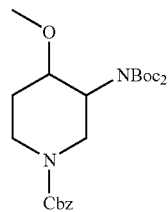

To a solution of NaH (1.3 equiv.) in THF (0.1M) was added benzyl 3-(bis(tert-butoxycarbonyl)amino)-4-hydroxypiperidine-1-carboxylate (1.0 equiv.) and the reaction was heated to 50° C. for 10 min. Upon cooling to room temperature, MeI (1.5 equiv.) was added and the solution was allowed to stir for 16 h. The reaction was quenched with water, then extracted with EtOAc, the organic was dried with brine and Na$_2$SO$_4$, and concentrated. The crude material was purified via silica gel column chromatography eluting with EtOAc and hexanes (1:3) to give a clear oil in 71% yield. LCMS (m/z): 365.0 (MH$^+$).

Synthesis of trans(+/−)-3-(bis(tert-butoxycarbonyl)amino)-4-methoxypiperidine

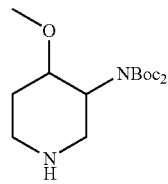

Method 2 was followed using trans(+/−)-benzyl 3-(bis(tert-butoxycarbonyl)amino)-4-methoxypiperidine-1-carboxylate (1.0 equiv.) yielding crude trans(+/−)-3-(bis(tert-butoxycarbonyl)amino)-4-methoxypiperidine that was used for the next step without further purification. LCMS (m/z): 331.2 (MH$^+$)

Synthesis of trans(+/−)-N,N-di-BOC-4-methoxy-1-(3-nitropyridin-4-yl)piperidin-3-amine

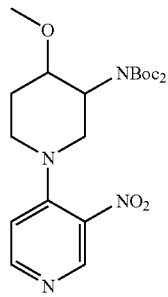

Method 1 was followed using trans(+/−)-3-(bis(tert-butoxycarbonyl)amino)-4-methoxypiperidine (1.0 equiv.), 4-chloro-3-nitropyridine (1.2 equiv.), and DIEA (4.0 equiv.) to give trans(+/−)-N,N-di-BOC-4-methoxy-1-(3-nitropyridin-4-yl)-piperidin-3-amine after column chromatography (EtOAc and hexanes, 50%) in 59% yield for two steps. LCMS (m/z): 453.2 (MH$^+$), LC R$_t$=3.24 min.

Synthesis of trans(+/−)-N,N-di-BOC-4-methoxy-1-(3-aminopyridin-4-yl)piperidin-3-amine

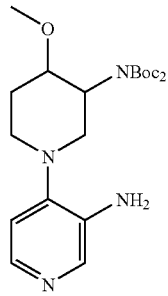

Method 2 was followed using trans(+/−)-N,N-di-BOC-4-methoxy-1-(3-nitropyridin-4-yl)-piperidin-3-amine to give trans(+/−)-N,N-di-BOC-4-methoxy-1-(3-aminopyridin-4-yl)piperidin-3-amine in >95% yield as a clear oil. LCMS (m/z): 423.0 (MH$^+$), LC R$_t$=3.10 min.

Synthesis of (3R,5R)-5-(tert-butyldimethylsilyloxy)piperidin-3-ol

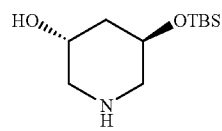

(3R,5R)-5-(tert-butyldimethylsilyloxy)piperidin-3-ol was prepared according to the patent procedure as described by Zhou, Y. WO2005028467.

Synthesis of (3R,5R)-benzyl 3-(tert-butyldimethylsilyloxy)-5-hydroxypiperidine-1-carboxylate

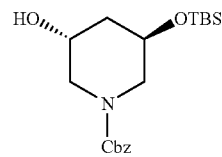

To a solution of (3R,5R)-5-(tert-butyldimethylsilyloxy)piperidin-3-ol (1 eq) in 20 mL of 1,4-dioxane and 8 mL of water was added benzyl chloroformate (1.5 eq). The mixture was stirred at room temperature for 4 hours. The crude mixture was diluted with 100 mL of EtOAc, washed with brine, then dried over anhydrous MgSO$_4$, filtered, and concentrated in vacuo. The crude residue was purified by flash chromatography (EtOAc:hexanes=1:3) to yield (3R,5R)-benzyl 3-(tert-butyldimethylsilyloxy)-5-hydroxypiperidine-1-carboxylate (74%). LC/MS (m/z): 366.2 (MH$^+$).

Synthesis of (3S,5R)-benzyl 3-(benzoyloxy)-5-(tert-butyl-dimethylsilyloxy)piperidine-1-carboxylate

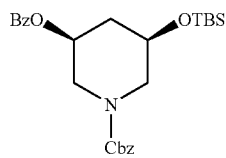

To a stirring 0° C. solution of triphenylphosphine (1.2 equiv) in 23 mL of THF was added di-tert-butyl azodicarboxylate (1.2 equiv). The mixture was stirred at 0° C. for 10 minutes. Then a solution of (3R,5R)-benzyl 3-(tert-butyldimethylsilyloxy)-5-hydroxypiperidien-1-carboxylate (1.0 equiv) in 11 mL of THF was added and stirred for 20 minutes at 0° C. Benzoic acid (1.2 equiv) was then added and the reaction mixture was allowed to slowly warm to rt. After 16 hours the reaction mixture was concentrated in vacuo then diluted with EtOAc and washed with water then brine. The organic layer was dried with Na$_2$SO$_4$, filtered, and concentrated in vacuo. The crude residue was purified by flash chromatography (EtOAc:hexanes=1:8) to yield (3S,5R)-benzyl 3-(benzoyloxy)-5-(tert-butyl-dimethylsilyloxy)piperidine-1-carboxylate (77%). LC/MS (m/z): 470.2 (MH$^+$), HPLC R$_t$=6.05 min.

Synthesis of (3S,5R)-benzyl 3-(benzoyloxy)-5-hydroxypiperidine-1-carboxylate

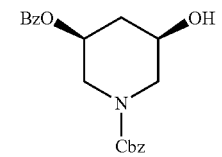

To a solution of (3S,5R)-benzyl 3-(benzoyloxy)-5-(tert-butyl-dimethylsilyloxy)-piperidine-1-carboxylate (1 eq) in 30 mL of methanol was added 3.8M HCl in isopropanol (4 eq). The reaction mixture was allowed to stand at room temperature for 3 hours at which point it was concentrated under reduced pressure. The resulting residue was diluted with 120 mL of EtOAc, washed with sat. aq. sodium bicarbonate, brine, then dried over anhydrous MgSO$_4$, filtered, and concentrated in vacuo. The crude residue was purified by flash chromatography (EtOAc:hexanes=1:1) to yield (3S,5R)-benzyl 3-(benzoyloxy)-5-hydroxypiperidine-1-carboxylate (95%). LC/MS (m/z): 355.9 (MH$^+$). HPLC: R$_t$: 3.62 min.

Synthesis of (3S,5S)-benzyl 3-azido-5-(benzoyloxy)piperidine-1-carboxylate

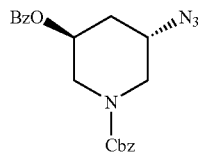

To a solution of (3S,5R)-benzyl 3-(benzoyloxy)-5-hydroxypiperidine-1-carboxylate (1 eq) in 20 mL of dichloromethane was added triethyl amine (3 eq) and methanesulfonyl chloride (1.5 eq) at 0° C. The reaction mixture was allowed to stir at room temperature for 2 hours. The crude mixture was diluted with 120 mL of EtOAc, washed with sat. aq. sodium bicarbonate, brine, then dried over anhydrous MgSO$_4$, filtered, and concentrated in vacuo. The crude residue was dissolved in 25 mL of NMP. Sodium azide (2.2 eq) was added and the resulting suspension was stirred at 80° C. overnight. The reaction mixture was diluted with 200 mL of EtOAc and 100 mL of hexanes, washed with water, brine, then dried over anhydrous MgSO$_4$, filtered, and concentrated in vacuo. The crude residue was purified by flash chromatography (EtOAc:hexanes=1:2) to yield (3S,5S)-benzyl 3-azido-5-(benzoyloxy)piperidine-1-carboxylate (88%). LC/MS (m/z): 381.0 (MH$^+$). HPLC: R$_t$: 4.41 min.

Synthesis of (3S,5S)-benzyl 3-(benzoyloxy)-5-(tert-butoxycarbonylamino)-piperidine-1-carboxylate

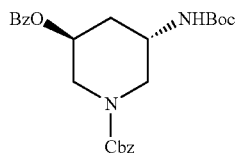

To a solution of (3S,5S)-benzyl 3-azido-5-(benzoyloxy)piperidine-1-carboxylate (1 eq) in a mixture of 14 mL of pyridine and 2 mL of ammonium hydroxide was added 1M trimethylphosphine (3 eq) at room temperature. The reaction mixture was stirred at room temperature for 3 hours at which point the solvents were removed under reduced pressure to give a yellow oil. The oil was again dissolved in 100 mL of ethanol and concentrated to remove ammonium hydroxide completely. The residue was dissolved in 24 ml of 1,4-dioxane and 24 mL of sat. aq. NaHCO$_3$ was added. Di-tert-butyl dicarbonate (4 eq) in 12 mL of THF was added dropwise at 0° C. The mixture was allowed to stir at room temperature for 2 hours. The crude mixture was diluted with 200 mL of EtOAc, washed with brine, then dried over anhydrous MgSO$_4$; filtered, and concentrated in vacuo. The crude residue was purified by flash chromatography (EtOAc:hexanes=1:2) to yield (3S,5S)-benzyl 3-(benzoyloxy)-5-(tert-butoxycarbonylamino)-piperidine-1-carboxylate (92%). LC/MS (m/z): 455.1 (MH$^+$). HPLC: R$_t$: 4.38 min.

Synthesis of (3S,5S)-5-(tert-butoxycarbonylamino)-1-(3-nitropyridin-4-yl)-piperidin-3-yl benzoate

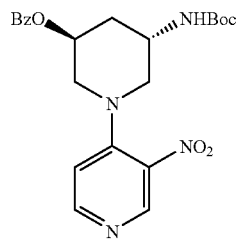

To a solution of (3S,5S)-benzyl 3-(benzoyloxy)-5-(tert-butoxycarbonylamino)-piperidine-1-carboxylate (1 eq) in 15 methanol and 15 mL of EtOAc was added 10% Pd/C (0.1 eq). The resulting suspension was stirred at H$_2$ atmosphere for 4 hours. The crude solids were filtered through a pad of Celite on a paper lined Buchner funnel, washed with MeOH, then concentrated in vacuo. The residue was dissolved in 20 mL of isopropanol and DIPEA (1.8 eq) and 4-chloro-3-nitropyridine (1.2 eq) were added. The reaction mixture was stirred at 75° C. for 2 hours, at which point the reaction mixture was allowed to cool to room temperature and concentrated under reduced pressure. The residue was diluted with 150 mL of EtOAc, washed with brine, then dried over anhydrous MgSO$_4$, filtered, and concentrated in vacuo. The crude residue was purified by flash chromatography (EtOAc:hexanes=1:1) to yield (3S,5S)-5-(tert-butoxycarbonylamino)-1-(3-nitropyridin-4-yl)-piperidin-3-yl benzoate (90%). LC/MS (m/z): 443.2 (MH$^+$). HPLC: R$_t$: 2.89 min.

Synthesis of (3S,5S)-1-(3-aminopyridin-4-yl)-5-(tert-butoxycarbonylamino)piperidin-3-yl benzoate

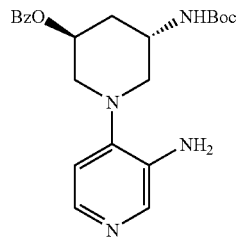

Following Method 2, (3S,5S)-5-(tert-butoxycarbonylamino)-1-(3-nitropyridin-4-yl)-piperidin-3-yl benzoate was reduced to yield (3S,5S)-1-(3-aminopyridin-4-yl)-5-(tert-butoxycarbonylamino)piperidin-3-yl benzoate. LC/MS (m/z): 413.1 (MH⁺). HPLC: R$_t$: 2.75 min.

Synthesis of (3S,5R)-benzyl 3-(tert-butoxycarbonylamino)-5-(tert-butyldimethylsilyloxy)piperidine-1-carboxylate

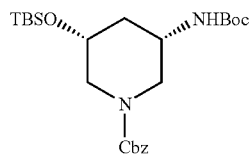

Followed method to synthesis of (3S,5S)-benzyl 3-(benzoyloxy)-5-(tert-butoxycarbonylamino)-piperidine-1-carboxylate starting from (3R,5R)-benzyl 3-(tert-butyldimethylsilyloxy)-5-hydroxypiperidine-1-carboxylate. LC/MS (m/z): 365.2 (MH⁺-Boc), Rt: 1.37.

Synthesis of (3S,5R)-benzyl 3-(tert-butoxycarbonylamino)-5-hydroxypiperidine-1-carboxylate

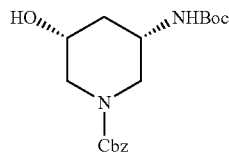

To a solution of (3S,5R)-benzyl 3-(tert-butoxycarbonylamino)-5-(tert-butyldimethylsilyloxy)piperidine-1-carboxylate (1 eq) in 30 mL of THF was added 5.2 mL of TBAF (1.2 eq). The reaction mixture was stirred at room temperature for 2 hours. The mixture was diluted with ethyl acetate, washed with brine, then dried over anhydrous MgSO₄, filtered, and concentrated in vacuo. The crude residue was purified by flash chromatography (5% methanol in EtOAc:hexanes=1:1) to yield (3S,5R)-benzyl 3-(tert-butoxycarbonylamino)-5-hydroxypiperidine-1-carboxylate (100%). LC/MS (m/z): 251.2 (MH⁺), Rt: 0.89. HPLC: Rt: 3.26 min.

Synthesis of (3S 5S)-benzyl 3-(tert-butoxycarbonylamino)-5-fluoropiperidine-1-carboxylate

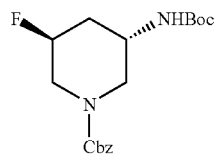

To a solution of the (3S,5R)-benzyl 3-(tert-butoxycarbonylamino)-5-hydroxypiperidine-1-carboxylate (1 eq) in 5 mL of dichloromethane was added DAST (1.35 eq). The reaction mixture was stirred at room temperature for 2 hours. The mixture was diluted with 120 mL of ethyl acetate, washed with brine, then dried over anhydrous MgSO₄, filtered, and concentrated in vacuo. The crude residue was purified by flash chromatography (EtOAc:hexanes=1:3) to yield tert-butyl(3S,5S)-1-(3-aminopyridin-4-yl)-5-fluoropiperidin-3-ylcarbamate (30%). LC/MS (m/z): 253.1 (MH⁺-100), R$_t$=0.96 min. HPLC: R$_t$: 3.79 min.

Synthesis of tert-butyl(3S,5S)-5-fluoro-1-(3-nitropyridin-4-yl)piperidin-3-ylcarbamate

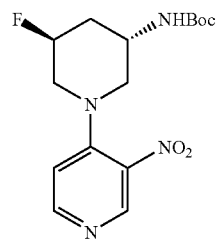

To a solution of (3S,5S)-benzyl 3-(tert-butoxycarbonylamino)-5-fluoropiperidine-1-carboxylate (1 eq) in 5 methanol and 5 mL of EtOAc was added 10% Pd/C (0.1 eq). The resulting suspension was stirred at H₂ atmosphere for 4 hours. The crude solids were filtered through a pad of Celite on a paper lined Buchner funnel, washed with MeOH, then concentrated in vacuo. The residue was dissolved in 5 mL of isopropanol and DIPEA (1.8 eq) and 4-chloro-3-nitropyridine (1.5 eq) were added. The reaction mixture was stirred at 65° C. for 3 hours, at which point the reaction mixture was allowed to cool to room temperature and concentrated under reduced pressure. The residue was diluted with 120 mL of EtOAc, washed with brine, then dried over anhydrous MgSO₄, filtered, and concentrated in vacuo. The crude residue was purified by flash chromatography (EtOAc:hexanes=1:1) to give tert-butyl(3S,5S)-5-fluoro-1-(3-nitropyridin-4-yl)piperidin-3-ylcarbamate (78%). LC/MS (m/z): 341.1 (MH⁺), R$_t$=0.57 min. HPLC: R$_t$: 2.01 min.

Synthesis of tert-butyl(3S,5S)-1-(3-aminopyridin-4-yl)-5-fluoropiperidin-3-ylcarbamate

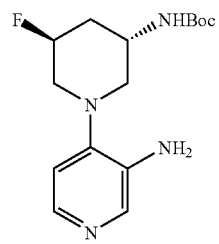

Following Method 2, tert-butyl(3S,5S)-5-fluoro-1-(3-nitropyridin-4-yl)piperidin-3-ylcarbamate was reduced to yield tert-butyl(3S,5S)-1-(3-aminopyridin-4-yl)-5-fluoropiperidin-3-ylcarbamate. LC/MS (m/z): 311.1 (MH⁺), R$_t$=0.54 min. HPLC: R$_t$: 1.76 min.

Synthesis of (S)-benzyl 3-(tert-butoxycarbonylamino)-5-oxopiperidine-1-carboxylate

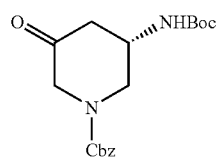

To a solution of (3S,5R)-benzyl 3-(tert-butoxycarbonylamino)-5-hydroxypiperidine-1-carboxylate (1 eq) in 10 mL dichloromethane was added Dess-Martin periodinane (1.2 eq) at room temperature. The reaction mixture was stirred at that temperature overnight. The mixture was diluted with ethyl acetate, washed with brine, then dried over anhydrous MgSO₄, filtered, and concentrated in vacuo. The crude residue was purified by flash chromatography (EtOAc:hexanes=1:2) to yield (S)-benzyl 3-(tert-butoxycarbonylamino)-5-oxopiperidine-1-carboxylate (81%). LC/MS (m/z): 249.1 (MH⁺-100), $R_t$: 0.83 min. HPLC: $R_t$: 3.26 min.

Synthesis of 5-(tert-butoxycarbonylamino)-3,3-difluoropiperidine-1-carboxylate

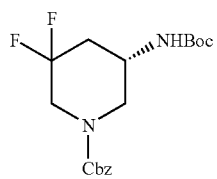

To a solution of the (S)-benzyl 3-(tert-butoxycarbonylamino)-5-oxopiperidine-1-carboxylate (1 eq) in 25 mL of dichloromethane was added DAST (20 eq). The reaction mixture was stirred at room temperature 3 hours. The reaction was quenched by aq. sodium bicarbonate. The resulting mixture was extracted with ethyl acetate. The organic layer was separated and washed with brine, then dried over anhydrous MgSO₄, filtered, and concentrated in vacuo. The crude residue was purified by flash chromatography (EtOAc:hexanes=1:2) to yield 5-(tert-butoxycarbonylamino)-3,3-difluoropiperidine-1-carboxylate (52%). LC/MS (m/z): 271.1 (-Boc), $R_t$: 0.99 min.

Synthesis of (S)-tert-butyl 5,5-difluoro-1-(3-nitropyridin-4-yl)piperidin-3-ylcarbamate

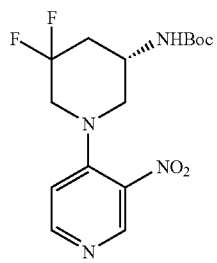

To a solution of 5-(tert-butoxycarbonylamino)-3,3-difluoropiperidine-1-carboxylate (1 eq) in 5 mL of methanol and 5 mL of EtOAc was added 10% Pd/C (0.1 eq). The resulting suspension was stirred at H2 atmosphere overnight. The crude solids were filtered through a pad of Celite on a paper lined Buchner funnel, washed with MeOH, then concentrated in vacuo. The residue was dissolved in 5 mL of isopropanol and DIPEA (2.0 eq) and 4-chloro-3-nitropyridine (1.5 eq) were added. The reaction mixture was stirred at 70° C. for 3 hours, at which point the reaction mixture was allowed to cool to room temperature and concentrated under reduced pressure. The residue was diluted with 120 mL of EtOAc, washed with brine, then dried over anhydrous MgSO₄, filtered, and concentrated in vacuo. The crude residue was purified by flash chromatography (5% methanol in EtOAc:hexanes=1:1) to yield (S)-tert-butyl 5,5-difluoro-1-(3-nitropyridin-4-yl)piperidin-3-ylcarbamate (19%). LC/MS (m/z): 359.0 (MH⁺), $R_t$: 0.65 min.

Synthesis of (S)-tert-butyl 1-(3-aminopyridin-4-yl)-5,5-difluoropiperidin-3-ylcarbamate

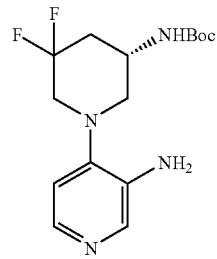

Following Method 2, (S)-tert-butyl 5,5-difluoro-1-(3-nitropyridin-4-yl)piperidin-3-ylcarbamate was reduced to yield (S)-tert-butyl 1-(3-aminopyridin-4-yl)-5,5-difluoropiperidin-3-ylcarbamate. LC/MS (m/z): 329.0 (MH⁺), $R_t$: 0.62 min.

Synthesis of (S)-benzyl 3-(tert-butoxycarbonylamino)-5-ethylidenepiperidine-1-carboxylate

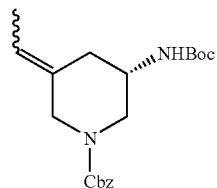

To a suspension of ethyltriphenylphosphonium bromide (11 eq) in 14 mL of THF was added potassium tert-butoxide (10 eq) at room temperature. The reaction mixture was stirred at that temperature for 20 minutes. Then the reaction was cooled to 0° C., and (S)-benzyl 3-(tert-butoxycarbonylamino)-5-oxopiperidine-1-carboxylate (1 eq) in 7 mL of THF was added to the reaction mixture. The reaction was allowed to warm up to room temperature. After being stirred for 40 minutes, the reaction mixture was poured into aq. sodium bicarbonate and extracted with ethyl acetate. The organic layer was separated and washed with brine, then dried over anhydrous MgSO₄, filtered, and concentrated in vacuo. The crude residue was purified by flash chromatography (EtOAc:hexanes=2:1) to yield (S)-benzyl 3-(tert-butoxycarbonylamino)-5-ethylidenepiperidine-1-carboxylate. LC/MS (m/z): 261.2 (MH⁺-100), $R_t$: 1.12 min. HPLC: $R_t$: 4.31 min.

Synthesis of tert-butyl(3S,5R)-5-ethyl-1-(3-nitropyridin-4-yl)piperidin-3-ylcarbamate

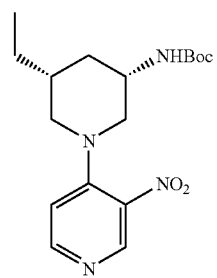

To a solution of (S)-benzyl 3-(tert-butoxycarbonylamino)-5-ethylidenepiperidine-1-carboxylate (1 eq) in 5.5 mL of ethanol and 5.5 mL of EtOAc was added 10% Pd/C (0.1 eq). The resulting suspension was stirred at H₂ atmosphere for 45 minutes. The crude solids were filtered through a pad of Celite on a paper lined Buchner funnel, washed with MeOH, then concentrated in vacuo. The residue was dissolved in 1.4 mL of isopropanol and DIPEA (2.5 eq) and 4-chloro-3-nitropyridine (1.5 eq) were added. The reaction mixture was stirred at 80° C. overnight, at which point the reaction mixture was allowed to cool to room temperature and concentrated under reduced pressure. The residue was diluted with 120 mL of EtOAc, washed with brine, then dried over anhydrous MgSO₄, filtered, and concentrated in vacuo. The crude residue was purified by flash chromatography (EtOAc:hexanes=1:1) to yield tert-butyl(3S,5R)-5-ethyl-1-(3-nitropyridin-4-yl)piperidin-3-ylcarbamate (91%). LC/MS (m/z): 351.2 (MH⁺), $R_t$: 0.75 min.

Synthesis of tert-butyl(3S,5R)-1-(3-aminopyridin-4-yl)-5-ethylpiperidin-3-ylcarbamate

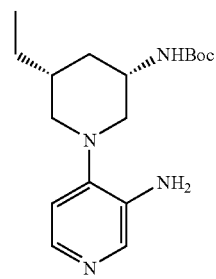

Following Method 2, tert-butyl(3S,5R)-5-ethyl-1-(3-nitropyridin-4-yl)piperidin-3-ylcarbamate was reduced to yield tert-butyl(3S,5R)-1-(3-aminopyridin-4-yl)-5-ethylpiperidin-3-ylcarbamate. LC/MS (m/z): 321.2 (MH⁺), $R_t$: 0.73 min. HPLC: $R_t$: 2.65 min.

Synthesis of (3R,5R)-benzyl 3-(tert-butyldimethylsilyloxy)-5-methoxypiperidine-1-carboxylate

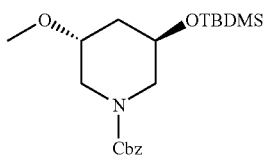

To a solution of (3R,5R)-benzyl 3-(tert-butyldimethylsilyloxy)-5-hydroxypiperidine-1-carboxylate (1 eq) in 30 mL of THF was added sodium hydride (1.5 eq) and followed by methyl iodide (5 eq) at 0° C. The reaction mixture was allowed to stir at room temperature for 3 hours. The crude mixture was diluted with 120 mL of EtOAc, washed with brine, then dried over anhydrous MgSO₄, filtered, and concentrated in vacuo. The crude residue was purified by flash chromatography (EtOAc:hexanes=1:5) to yield (3R,5R)-benzyl 3-(tert-butyldimethylsilyloxy)-5-methoxypiperidine-1-carboxylate (93%). LC/MS (m/z): 380.2 (MH⁺).

Synthesis of (3R,5R)-benzyl 3-hydroxy-5-methoxypiperidine-1-carboxylate

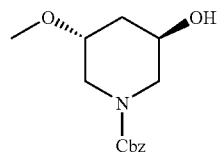

To a solution of (3R,5R)-benzyl 3-(tert-butyldimethylsilyloxy)-5-methoxypiperidine-1-carboxylate (1 eq) in 30 mL of methanol was added 3.8M HCl in isopropanol (4 eq). The reaction mixture was allowed to stand at room temperature for 3 hours at which point it was concentrated under reduced pressure. The resulting residue was diluted with 100 mL of EtOAc, washed with sat. aq. sodium bicarbonate, brine, then dried over anhydrous MgSO₄, filtered, and concentrated in vacuo. The crude residue was purified by flash chromatography (EtOAc:hexanes=2:1) to yield (3R,5R)-benzyl 3-hydroxy-5-methoxypiperidine-1-carboxylate (92%). LC/MS (m/z): 266.2 (MH⁺).

Synthesis of (3S,5R)-benzyl 3-azido-5-methoxypiperidine-1-carboxylate

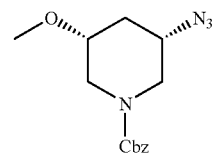

To a solution of (3R,5R)-benzyl 3-hydroxy-5-methoxypiperidine-1-carboxylate (1 eq) in 40 mL of dichloromethane was added triethyl amine (3 eq) and methanesulfonyl chloride (1.5 eq) at 0° C. The reaction mixture was allowed to stir at room temperature for 2 hours. The crude mixture was diluted with 150 mL of EtOAc, washed with sat. aq. sodium bicarbonate, brine, then dried over anhydrous MgSO₄, filtered, and concentrated in vacuo. The crude residue was purified by flash chromatography (EtOAc:hexanes=1:1) to give the intermediate, which was dissolved in 15 mL of DMF. Sodium azide (3.3 eq) was added and the resulting suspension was stirred at 80° C. overnight. The reaction mixture was diluted with 150 mL of EtOAc, washed with water, brine, then dried over anhydrous MgSO₄, filtered, and concentrated in vacuo. The crude residue was purified by flash chromatography (EtOAc:hexanes=1:2) to yield (3S,5R)-benzyl 3-azido-5-methoxypiperidine-1-carboxylate (95%). LC/MS (m/z): 263.2 (MH⁺-28).

Synthesis of (3S,5R)-benzyl 3-(tert-butoxycarbonylamino)-5-methoxypiperidine-1-carboxylate

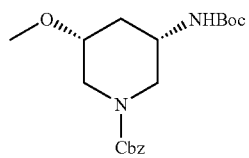

To a solution of (3S,5R)-benzyl 3-azido-5-methoxypiperidine-1-carboxylate (1 eq) in a mixture of 14 mL of pyridine and 2 mL of ammonium hydroxide was added 1M trimethylphosphine (3 eq) at room temperature. The reaction mixture was stirred at room temperature for 4 hours at which point the solvents were removed under reduced pressure to give a yellow oil. The oil was again dissolved in 100 mL of ethanol and concentrated to remove ammonium hydroxide completely. The residue was dissolved in 16 ml of 1,4-dioxane and 16 mL of sat. aq. NaHCO₃ was added. Di-tert-butyl dicarbonate (4 eq) in 8 mL of THF was added dropwise at 0° C. The mixture was allowed to stir at room temperature for 2 hours. The crude mixture was diluted with 300 mL of EtOAc, washed with brine, then dried over anhydrous MgSO₄, filtered, and concentrated in vacuo. The crude residue was purified by flash chromatography (EtOAc:hexanes=1:1) to yield (3S,5R)-benzyl 3-(tert-butoxycarbonylamino)-5-methoxypiperidine-1-carboxylate (86%). LC/MS (m/z): 365.0 (MH$^+$).

Synthesis of tert-butyl(3S,5R)-5-methoxy-1-(3-nitropyridin-4-yl)piperidin-3-ylcarbamate

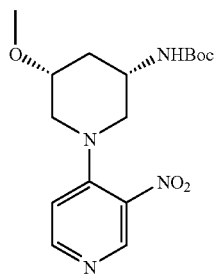

To a solution of (3S,5R)-benzyl 3-(tert-butoxycarbonylamino)-5-methoxypiperidine-1-carboxylate (1 eq) in 25 methanol was added 10% Pd/C (0.1 eq). The resulting suspension was stirred at H₂ atmosphere for 2 hours. The crude solids were filtered through a pad of Celite on a paper lined Buchner funnel, washed with MeOH, then concentrated in vacuo. The residue was dissolved in 25 mL of isopropanol and DIEA (1.8 eq) and 4-chloro-3-nitropyridine (1.2 eq) were added. The reaction mixture was stirred at 80° C. for 4 hours, at which point the reaction mixture was allowed to cool to room temperature and concentrated under reduced pressure. The residue was diluted with 150 mL of EtOAc, washed with brine, then dried over anhydrous MgSO₄, filtered, and concentrated in vacuo. The crude residue was purified by flash chromatography (5% methanol in EtOAc:hexanes=1:1) to yield (3S,5R)-5-methoxy-1-(3-nitropyridin-4-yl)piperidin-3-ylcarbamate (88%). LC/MS (m/z): 353.0 (MH$^+$). HPLC: R$_t$: 2.15 min.

Synthesis of tert-Butyl(3S,5R)-1-(3-aminopyridin-4-yl)-5-methoxypiperidin-3-ylcarbamate

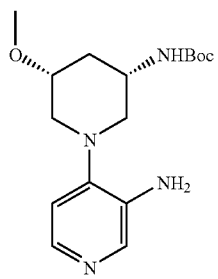

Following Method 2, tert-butyl(3S,5R)-5-methoxy-1-(3-nitropyridin-4-yl)piperidin-3-ylcarbamate was reduced yielding tert-Butyl(3S,5R)-1-(3-aminopyridin-4-yl)-5-methoxypiperidin-3-ylcarbamate. LC/MS (m/z): 323.1 (MH$^+$).

Synthesis of tert-butyl(3S,5R)-1-(3-aminopyridin-4-yl)-5-ethoxypiperidin-3-ylcarbamate

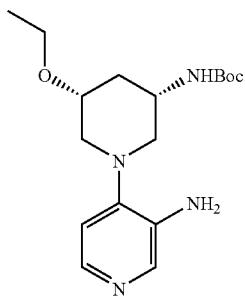

The procedure to prepare this compound is as same as the methoxy compound. LC/MS (m/z): 337.1 (MH$^+$), R$_t$: 0.63 min. HPLC: R$_t$: 2.47 min.

Synthesis of (3R,5R)-3-(tert-butyldimethylsilyloxy)-5-fluoro-1-(4-methoxybenzyl)piperidine

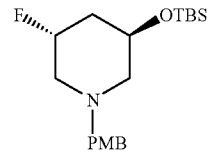

(3R,5R)-3-(tert-butyldimethylsilyloxy)-5-fluoro-1-(4-methoxybenzyl)-piperidine was prepared according to the literature procedure as described by Cossy, J. *Synlett,* 2007, 263.

Synthesis of (3R,5R)-3-(tert-butyldimethylsilyloxy)-5-fluoropiperidine

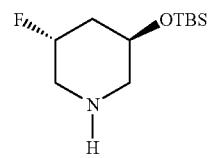

To a solution of (3R,5R)-3-(tert-butyldimethylsilyloxy)-5-fluoro-1-(4-methoxybenzyl)piperidine (1 eq) in 5 mL of methanol was added 10% Pd/C (0.2 eq). The resulting suspension was stirred at H₂ atmosphere overnight. The crude solids were filtered through a pad of Celite on a paper lined Buchner funnel, washed with MeOH, then concentrated in vacuo to yield (3R,5R)-3-(tert-butyldimethylsilyloxy)-5-fluoropiperidine, which was used to next step without further purification. LC/MS (m/z): 234.1 (MH$^+$).

Synthesis of (3R,5R)-benzyl 3-fluoro-5-hydroxypiperidine-1-carboxylate

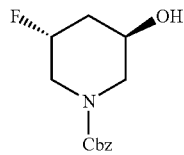

To a solution of (3R,5R)-3-(tert-butyldimethylsilyloxy)-5-fluoropiperidine (1 eq) in 30 mL of methanol was added 3.8M HCl in isopropanol (4 eq). The reaction mixture was allowed to stand at room temperature for 3 hours at which point it was concentrated under reduced pressure. The resulting residue was diluted with 120 mL of EtOAc, washed with sat. aq. sodium bicarbonate, brine, then dried over anhydrous MgSO$_4$, filtered, and concentrated in vacuo. The crude residue was purified by flash chromatography (EtOAc:hexanes=2:1) to give (3R,5R)-benzyl 3-fluoro-5-hydroxypiperidine-1-carboxylate, (94%). LC/MS (m/z): 254.2 (MH$^+$).

Synthesis of (3S,5R)-benzyl 3-azido-5-fluoropiperidine-1-carboxylate

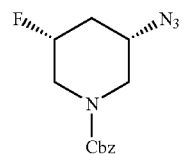

To a solution of (3R,5R)-benzyl 3-fluoro-5-hydroxypiperidine-1-carboxylate (1 eq) in 14 mL of dichloromethane was added triethyl amine (3 eq) and methanesulfonyl chloride (1.5 eq) at 0° C. The reaction mixture was allowed to stir at room temperature for 1.5 hours. The crude mixture was diluted with 120 mL of diethyl ether, washed with sat. aq. sodium bicarbonate, brine, then dried over anhydrous MgSO$_4$, filtered, and concentrated in vacuo. The crude residue was dissolved in 16 mL of NMP. Sodium azide (3.0 eq) was added and the resulting suspension was stirred at 80° C. overnight. The reaction mixture was diluted with 200 mL of EtOAc and 100 mL of hexanes, washed with water, brine, then dried over anhydrous MgSO$_4$, filtered, and concentrated in vacuo. The crude residue was purified by flash chromatography (EtOAc:hexanes=1:3) to yield (3S,5R)-benzyl 3-azido-5-fluoropiperidine-1-carboxylate (90%). LC/MS (m/z): 251.1 (MH$^+$-28).

Synthesis of (3S,5R)-benzyl 3-(tert-butoxycarbonylamino)-5-fluoropiperidine-1-carboxylate

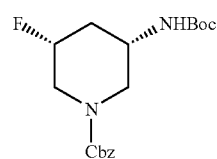

To a solution of (3S,5R)-benzyl 3-azido-5-fluoropiperidine-1-carboxylate (1 eq) in a mixture of 11 mL of pyridine and 1.5 mL of ammonium hydroxide was added 1M trimethylphosphine (3 eq) at room temperature. The reaction mixture was stirred at room temperature for 3 hours at which point the solvents were removed under reduced pressure to give a yellow oil. The oil was again dissolved in 100 mL of ethanol and concentrated to remove ammonium hydroxide completely. The residue was dissolved in 12 ml of 1,4-dioxane and 12 mL of sat. aq. NaHCO$_3$ was added. Di-tert-butyl dicarbonate (4 eq) in 6 mL of THF was added dropwise at 0° C. The mixture was allowed to stir at room temperature for 1 hour. The crude mixture was diluted with 150 mL of EtOAc, washed with brine, then dried over anhydrous MgSO$_4$, filtered, and concentrated in vacuo. The crude residue was purified by flash chromatography (EtOAc:hexanes=1:1) to yield (3S,5R)-benzyl 3-(tert-butoxycarbonylamino)-5-fluoropiperidine-1-carboxylate (95%). LC/MS (m/z): 253.1 (MH$^+$-100).

Synthesis of tert-butyl(3S,5R)-5-fluoro-1-(3-nitropyridin-4-yl)piperidin-3-ylcarbamate

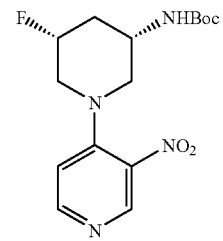

To a solution of (3S,5R)-benzyl 3-(tert-butoxycarbonylamino)-5-fluoropiperidine-1-carboxylate (1 eq) in 28 methanol was added 10% Pd/C (0.1 eq). The resulting suspension was stirred at H$_2$ atmosphere for 1 hours. The crude solids were filtered through a pad of Celite on a paper lined Buchner funnel, washed with MeOH, then concentrated in vacuo. The residue was dissolved in 33 mL of isopropanol and DIPEA (2.5 eq) and 4-chloro-3-nitropyridine (1.5 eq) were added. The reaction mixture was stirred at 80° C. for 2 hours, at which point the reaction mixture was allowed to cool to room temperature and concentrated under reduced pressure. The residue was diluted with 150 mL of EtOAc, washed with brine, then dried over anhydrous MgSO$_4$, filtered, and concentrated in vacuo. The crude residue was purified by flash chromatography (5% methanol in EtOAc:hexanes=1:1) to yield tert-butyl(3S,5R)-5-fluoro-1-(3-nitropyridin-4-yl)piperidin-3-ylcarbamate (90%). LC/MS (m/z): 341.1 (MH$^+$). HPLC: R$_t$: 2.12 min.

Synthesis of tert-Butyl(3S,5R)-1-(3-aminopyridin-4-yl)-5-fluoropiperidin-3-ylcarbamate

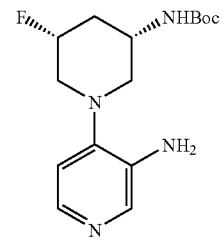

Following Method 2, tert-butyl(3S,5R)-5-fluoro-1-(3-nitropyridin-4-yl)piperidin-3-ylcarbamate was reduced yielding tert-Butyl(3S,5R)-1-(3-aminopyridin-4-yl)-5-fluoropiperidin-3-ylcarbamate. LC/MS (m/z): 311.1 (MH⁺).

Synthesis of tert-butyl 5-methylpyridin-3-ylcarbamate

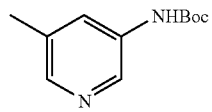

To a solution of 5-methylpyridin-3-amine (5 g, 46 mmol) in THF (80 mL) at r.t. was added 1M sodium bis(trimethylsilylamide) in THF (101 mL, 101 mmol), stirred for 15 min, followed by di-tert-butyldicarbonate (11 g, 49 mmol) in THF (20 mL). The reaction was stirred at r.t overnight and concentrated. The concentrate was treated with 0.2M HCl (60 mL) and EtOAc, and the organic layer was extracted, washed with NaHCO$_{3(sat.)}$ and brine, dried over Na$_2$SO$_4$, filtered and concentrated. The concentrate was purified using flash chromatography on silica gel (40% EtOAc:Hexane) to give a yellow solid as product tert-butyl 5-methylpyridin-3-ylcarbamate (8.5 g, 88% yield). LCMS (m/z): 209.1 (MH⁺); LC R$_t$=1.94 min. $^1$H NMR(CDCl$_3$) δ 8.20 (d, 1H), 8.12 (s, 1H), 7.86 (s, 1H), 6.53 (s, 1H), 2.33 (s, 3H), 1.53 (s, 9H).

Synthesis of cis-(+/−)-tert-butyl 5-methylpiperidin-3-ylcarbamate

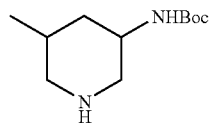

To a solution of 5-methylpyridin-3-ylcarbamate (3 g, 14 mmol) in glacial acetic Acid (50 mL) was added 5% Rhodium on active carbon (0.5 g) and Platinum(IV) oxide (0.5 g) in the hydrogenation steel bomb. The mixture was sealed and hydrogenated at 200 psi and 70° C. for 48 hours. The mixture was filtered through Celite and concentrated to give cis-(+/−)-tert-butyl 5-methylpiperidin-3-ylcarbamate. LCMS (m/z): 215.1 (MH⁺).

Synthesis of cis-(+/−)-tert-butyl 5-methyl-1-(3-nitropyridin-4-yl)piperidin-3-ylcarbamate

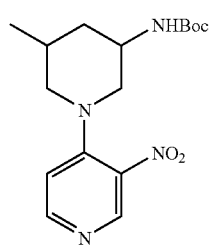

Method 1 was followed using crude cis-(+/−)-tert-butyl 5-methylpiperidin-3-ylcarbamate yielding cis-(+/−)-tert-butyl 5-methyl-1-(3-nitropyridin-4-yl)piperidin-3-ylcarbamate (66% yield). LCMS (m/z): 337.1 (MH⁺); LC R$_t$=2.50 min. $^1$H NMR(CDCl$_3$) δ 8.84 (s, 1H), 8.36 (d, 1H), 7.04 (m, 1H), 4.44 (m, 1H), 3.90 (m, 1H), 3.71 (m, 1H), 3.09 (d, 1H), 2.66 (q, 2H), 2.10 (d, 1H), 1.84 (m, 1H), 1.56 (s, 9H), 0.93 (d, 3H).

Synthesis of cis-(+/−)-tert-butyl 1-(3-aminopyridin-4-yl)-5-methylpiperidin-3-ylcarbamate

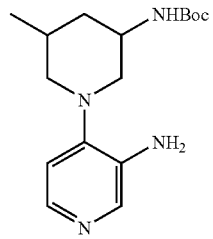

Method 2 was followed using cis-(+/−)-tert-butyl 5-methyl-1-(3-nitropyridin-4-yl)piperidin-3-ylcarbamate yielding cis-(+/−)-tert-butyl 5-methyl-1-(3-aminopyridin-4-yl)piperidin-3-ylcarbamate (98% yield). LCMS (m/z): 307.1 (MH⁺); LC R$_t$=2.44 min. $^1$H NMR(CDCl$_3$) δ 8.01 (s, 1H), 7.95 (d, 1H), 6.76 (d, 1H), 4.40 (m, 1H), 3.70 (m, 3H), 3.58 (dq, 1H), 3.21 (dq, 1H), 2.15 (m, 3H), 1.90 (m, 1H), 1.58 (s, 9H), 0.97 (d, 3H).

Synthesis of tert-butyl 5-(trifluoromethyl)pyridin-3-ylcarbamate

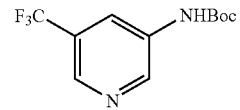

To a solution of 5-trifluoromethylpyridin-3-amine (1 eq.) in THF (80 mL) at r.t. was added 1M sodium bis(trimethylsilylamide) in THF (2 eq.), stirred for 15 min, followed by di-tert-butyldicarbonate (1 eq.) in THF. The reaction was stirred at r.t overnight and concentrated. The concentrate was treated with 0.2M HCl aq. and EtOAc, and the organic layer was extracted, washed with NaHCO$_{3(sat.)}$ and brine, dried over Na$_2$SO$_4$, filtered and concentrated. The concentrate was purified using flash chromatography on silica gel (40% EtOAc:Hexane) to give a yellow solid as product tert-butyl 5-(trifluoromethyl)pyridin-3-ylcarbamate (31% yield). LCMS (m/z): 263.0 (MH⁺); LC R$_t$=3.84 min. $^1$H NMR (CDCl$_3$) δ 8.56 (m, 2H), 8.34 (s, 1H), 6.71 (s, 1H), 1.55 (s, 9H).

Synthesis of cis-(+/−)-tert-butyl 5-(trifluoromethyl)piperidin-3-ylcarbamate

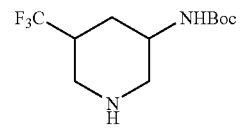

To a solution of tert-butyl 5-(trifluoromethyl)pyridin-3-ylcarbamate (3 g, 14 mmol) in glacial acetic acid (50 mL) was added 5% Rhodium on active carbon (0.5 g) and Platinum (IV) oxide (0.5 g) in the hydrogenation steel bomb. The mixture was sealed and hydrogenated at 200 psi and 70° C. for 48 h. the mixture was filtered through Celite and concentrated to give cis-(+/−)-tert-butyl 5-(trifluoromethyl)piperidin-3-ylcarbamate. LCMS (m/z): 269.1 (MH$^+$).

Synthesis of cis-(+/−)-tert-butyl 1-(3-nitropyridin-4-yl)-5-(trifluoromethyl)piperidin-3-ylcarbamate

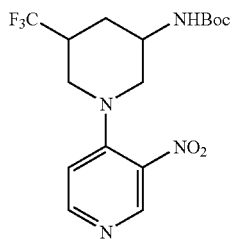

Method 1 was followed using crude cis-(+/−)-tert-butyl 5-(trifluoromethyl)piperidin-3-ylcarbamate yielding cis-(+/−)-tert-butyl 1-(3-nitropyridin-4-yl)-5-(trifluoromethyl)piperidin-3-ylcarbamate (42% yield over two steps). LCMS (m/z): 391.1 (MH$^+$); LC R$_t$=2.92 min. $^1$H NMR(CDCl$_3$) δ 8.93 (s, 1H), 8.47 (d, 1H), 7.01 (d, 1H), 4.50 (m, 1H), 3.80 (m, 2H), 3.45 (m, 1H), 3.00 (t, 1H), 2.66 (m, 1H), 2.63 (m, 1H), 2.38 (d, 1H), 1.56 (s, 9H).

Synthesis cis-(+/−)-tert-butyl 1-(3-aminopyridin-4-yl)-5-(trifluoromethyl)piperidin-3-ylcarbamate

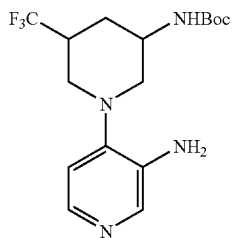

Method 2 was followed using cis-(+/−)-tert-butyl 1-(3-nitropyridin-4-yl)-5-(trifluoromethyl)piperidin-3-ylcarbamate yielding cis-(+/−)-tert-butyl 1-(3-aminopyridin-4-yl)-5-(trifluoromethyl)piperidin-3-ylcarbamate. LCMS (m/z): 361.0 (MH$^+$); LC R$_t$=2.72 min. $^1$H NMR(CDCl$_3$) δ 8.05 (s, 1H), 7.98 (d, 1H), 6.79 (d, 1H), 4.46 (m, 1H), 3.83 (m, 1H), 3.72 (s, 2H), 3.62 (m, 1H), 3.49 (m, 1H), 2.59 (m, 2H), 2.36 (m, 1H), 2.23 (t, 1H), 1.58 (s, 9H).

Synthesis of cis(+/−)-1-benzyl 3-methyl 5-(tert-butoxycarbonylamino)piperidine-1,3-dicarboxylate

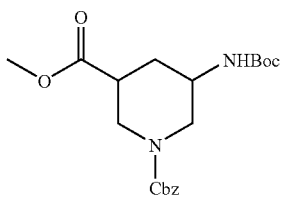

To a solution of cis(+/−)-1-(benzyloxycarbonyl)-5-(tert-butoxycarbonylamino)piperidine-3-carboxylic acid (1.0 eq), methanol (20 eq.) and EDC (1.3 eq) in dichloromethane at a concentration of 0.25 M at 0° C. was added dimethylaminopyridine (0.1 eq). After stirring for 48 hours as the reaction was allowed to warm to rt the volatiles were removed in vacuo. Upon addition of ethyl acetate and washing with H$_2$O (3×), 1N HCl, NaHCO$_{3(sat.)}$ and brine, the solution was dried over MgSO$_4$, filtered, concentrated and purified by column chromatography (25% ethyl acetate/hexanes) to yield cis (+/−)-1-benzyl 3-methyl 5-(tert-butoxycarbonylamino)-piperidine-1,3-dicarboxylate. LCMS (m/z): 293.1 (MH-Boc$^+$); LC R$_t$=4.09 min Synthesis of cis(+/−)-benzyl 3-(tert-butoxycarbonylamino)-5-(hydroxymethyl)piperidine-1-carboxylate

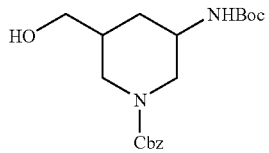

A solution of cis(+/−)-1-benzyl 3-methyl 5-(tert-butoxycarbonylamino)piperidine-1,3-dicarboxylate (1.0 eq.) in THF at a concentration of 0.08 M was cooled at 0° C. and then LiCl (2.3 eq.) and sodium borohydride (2.3 eq.) were added. After stirring for 20 hours as the reaction warmed to rt, the pH was adjusted with 1M citric acid to pH 4-5. After removal of the volatiles in vacuo, the product was extracted in dichloromethane, washed with H$_2$O and brine, dried over MgSO$_4$. Upon filtering and removal of the volatiles in vacuo, cis(+/−)-benzyl 3-(tert-butoxycarbonylamino)-5-(hydroxymethyl)piperidine-1-carboxylate was obtained as a white foamy solid. LCMS (m/z): 265.0 (MH-Boc$^+$); LC R$_t$=3.37 min.

Synthesis of cis(+/−)-benzyl 3-(tert-butoxycarbonylamino)-5-((tert-butyldimethylsilyloxy)methyl)piperidine-1-carboxylate

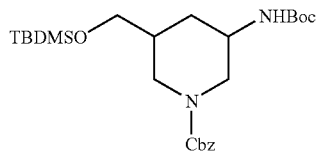

A solution of cis(+/−)-benzyl 3-(tert-butoxycarbonylamino)-5-(hydroxymethyl)piperidine-1-carboxylate (1.0 eq.), imidazole (1.1 eq.), tert-butyldimethylsilylchloride (1.1 eq.) and dimethylaminopyridine (0.1 eq.) in dichloromethane at a concentration of 0.1 M was stirred for 18 hours at which time the volatiles were removed in vacuo. Direct purification of the crude material by column chromatography (20% ethyl acetate/hexanes) yielded cis(+/−)-benzyl 3-(tert-butoxycarbonylamino)-5-((tert-butyldimethylsilyloxy)methyl)piperidine-1-carboxylate. LCMS (m/z): 379.0 (MH-Boc$^+$); LC R$_t$=5.95 min.

Synthesis of cis(+/−)-tert-butyl 5-((tert-butyldimethylsilyloxy)methyl)piperidin-3-ylcarbamate

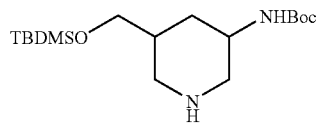

Method 2 was followed to deprotect cis(+/−)-benzyl 3-(tert-butoxy-carbonylamino)-5-(((tert-butyldimethylsilyloxy)methyl)piperidine-1-carboxylate yielding cis(+/−)-tert-butyl 5-(((tert-butyldimethylsilyloxy)methyl)piperidin-3-ylcarbamate. LCMS (m/z): 344.1 (MH$^+$).

Synthesis of cis(+/−)-tert-butyl 5-((tert-butyldimethylsilyloxy)methyl)-1-(3-nitropyridin-4-yl)piperidin-3-ylcarbamate

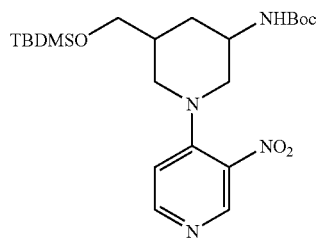

Method 1 was followed using cis(+/−)-tert-butyl 5-((tert-butyldimethylsilyloxy)methyl)piperidin-3-ylcarbamate and 4-chloro-3-nitropyridine yielding cis(+/−)-tert-butyl 5-(((tert-butyldimethylsilyloxy)methyl)-1-(3-nitropyridin-4-yl)-piperidin-3-ylcarbamate. LCMS (m/z): 467.0 (MH$^+$); LC R$_t$=4.02 min.

Synthesis of cis(+/−)-tert-butyl 1-(3-aminopyridin-4-yl)-5-((tert-butyldimethylsilyloxy)methyl)piperidin-3-ylcarbamate

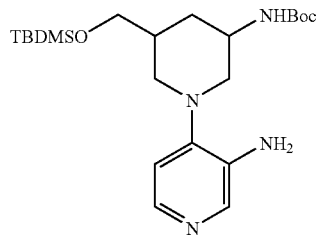

Following Method 2, cis(+/−)-tert-butyl 5-(((tert-butyldimethylsilyloxy)methyl)-1-(3-nitropyridin-4-yl)piperidin-3-ylcarbamate was reduced yielding cis(+/−)-tert-butyl 1-(3-aminopyridin-4-yl)-5-(((tert-butyldimethylsilyloxy)methyl) piperidin-3-ylcarbamate. LCMS (m/z): 437.2 (MH$^+$); LC R$_t$=3.86 min.

Synthesis of cis(+/−)-benzyl 3-(tert-butoxycarbonylamino)-5-(fluoromethyl)piperidine-1-carboxylate

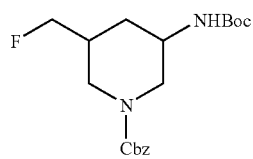

A solution of cis(+/−)-benzyl 3-(tert-butoxycarbonylamino)-5-(hydroxymethyl)piperidine-1-carboxylate (1 eq.), perfluorobutanesulfonylfluoride (2 eq.), triethylamine-HF (4 eq.) and triethylamine (6 eq.) in tetrahydrofuran at a concentration of 0.16 M was stirred for 36 hours. Upon dilution with ethyl acetate (50×) the solution was washed with 1N HCl, NaHCO$_{3(sat.)}$ and brine, was dried over MgSO$_4$, filtered, concentrated and purified by column chromatography (25-40% ethyl acetate/hexanes) to yield cis(+/−)-benzyl 3-(tert-butoxycarbonylamino)-5-(fluoromethyl)piperidine-1-carboxylate (45% yield). LCMS (m/z): 267.1 (MH$^+$); LC R$_t$=4.23 min.

Synthesis of cis(+/−)-tert-butyl 5-(fluoromethyl)piperidin-3-ylcarbamate

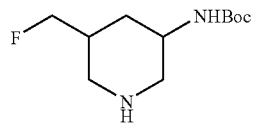

Method 2 was followed to deprotect cis(+/−)-benzyl 3-(tert-butoxycarbonylamino)-5-(fluoromethyl)piperidine-1-carboxylate yielding cis(+/−)-tert-butyl 5-(fluoromethyl)piperidin-3-ylcarbamate. LCMS (m/z): 233.1 (MH$^+$).

Synthesis of cis(+/−)-tert-butyl 5-(fluoromethyl)-1-(3-nitropyridin-4-yl)piperidin-3-ylcarbamate

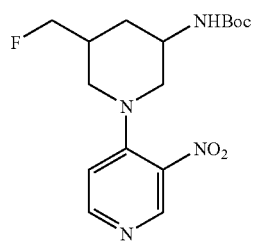

Method 1 of example 1 was followed using cis(+/−)-tert-butyl 5-(fluoromethyl)piperidin-3-ylcarbamate and 4-chloro-3-nitropyridine yielding cis(+/−)-tert-butyl 5-(fluoromethyl)-1-(3-nitropyridin-4-yl)piperidin-3-ylcarbamate. LCMS (m/z): 355.1 (MH$^+$); LC R$_t$=2.41 min.

Synthesis of cis(+/−)-tert-butyl 1-(3-aminopyridin-4-yl)-5-(fluoromethyl)piperidin-3-ylcarbamate

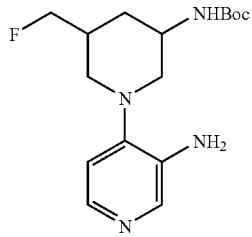

Following Method 2, cis(+/−)-tert-butyl 5-(fluoromethyl)-1-(3-nitropyridin-4-yl)piperidin-3-ylcarbamate was reduced yielding cis(+/−)-tert-butyl 1-(3-aminopyridin-4-yl)-5-(fluoromethyl)piperidin-3-ylcarbamate. LCMS (m/z): 325.1 (MH$^+$); LC R$_t$=2.27 min.

Synthesis of (3R,4R)-benzyl 3-(tert-butoxycarbonylamino)-4-(methylsulfonyloxy)piperidine-1-carboxylate

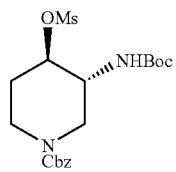

To a solution of (3R,4R)-benzyl 3-(tert-butoxycarbonylamino)-4-hydroxypiperidine-1-carboxylate in dichloromethane (0.13 M) was added triethylamine (1.5 equiv.) followed by methanesulfonyl chloride (1.3 equiv.). The reaction was allowed to stir at room temperature for 15 h. The solution was then quenched with saturated NaHCO$_3$, extracted with dichloromethane, dried with sodium sulfate, and concentrated to give the crude (3R,4R)-benzyl 3-(tert-butoxycarbonylamino)-4-(methylsulfonyloxy)piperidine-1-carboxylate in >95% yield. LCMS (m/z): 428.9/328.9 (MH$^+$), R$_t$=3.81 min.

Synthesis of (3aR,7aS)-benzyl 2-oxohexahydrooxazolo[4,5-c]pyridine-5(6H)-carboxylate

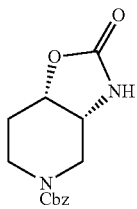

A solution of (3R,4R)-benzyl 3-(tert-butoxycarbonylamino)-4-(methylsulfonyloxy)piperidine-1-carboxylate in pyridine (0.16 M) was heated to 120° C. in the microwave for 10 minutes. The solution was then concentrated to almost dryness and the forming solid was filtered to give the desired product. The filtrate was further purified via silica gel column chromatography eluting with ethyl acetate (100%) to yield (3aR,7aS)-benzyl 2-oxohexahydrooxazolo[4,5-c]pyridine-5(6H)-carboxylate in 75% combined yield. LCMS (m/z): 277.1 (MH$^+$), R$_t$=2.327 min.

Synthesis of (3aR,7aS)-5-benzyl 3-tert-butyl 2-oxotetrahydrooxazolo[4,5-c]pyridine-3,5(2H,6H)-dicarboxylate

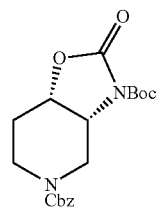

To a solution of (3aR,7aS)-benzyl 2-oxohexahydrooxazolo[4,5-c]pyridine-5(6H)-carboxylate (1.0 equiv.) in dichloromethane (0.09 M) was added BOC$_2$O (1.1 equiv.), triethylamine (1.1 equiv.), and a catalytic amount of DMAP. The reaction was stirred at room temperature for one hour at which point it was concentrated under vacuo and filtered through a plug of silica gel eluting with ethylacetate. The product was dried under vacuo to yield (3aR,7aS)-5-benzyl 3-tert-butyl 2-oxotetrahydrooxazolo[4,5-c]pyridine-3,5(2H,6H)-dicarboxylate as a white solid in 75% yield. LCMS (m/z): 277.2 (MH$^+$), R$_t$=3.43 min.

Synthesis of (3aR,7aS)-tert-butyl 5-(3-nitropyridin-4-yl)-2-oxohexahydrooxazolo[4,5-c]pyridine-3(2H)-carboxylate

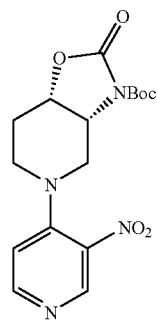

To a solution of (3aR,7aS)-5-benzyl 3-tert-butyl 2-oxotetrahydrooxazolo[4,5-c]pyridine-3,5(2H,6H)-dicarboxylate in a mixture of EtOH and EtOAc (1:1, 0.07 M) was added Pd/C (10% by weight) and the reaction was stirred under a hydrogen balloon for 15 h. The solution was then filtered through a pad of Celite and the filtrate was concentrated to dryness to give a clear oil. To a solution of (3aR,7aS)-tert-butyl 2-oxohexahydrooxazolo[4,5-c]pyridine-3(2H)-carboxylate in i-PrOH (0.12 M) was added 4-chloro-3-nitropyridine (1.2 equiv.) and DIEA (4.0 equiv.) The reaction was heated to 75° C. for 2 h, then cooled to room temperature and concentrated under vacuo. The crude mixture was diluted with EtOAc, water was added, the organic layer was extracted, washed with brine, dried with Na$_2$SO$_4$, and concentrated. The crude was purified via silica gel column chromatography eluting with EtOAc (100%) to yield (3aR,7aS)-tert-butyl 5-(3-nitro-pyridin-4-yl)-2-oxohexahydrooxazolo[4,5-c]pyridine-3(2H)-carboxylate as a yellow foam in 89% yield). LCMS (m/z): 365.1 (MH+), R$_t$=1.79 min.

Synthesis of (3aR,7aS)-tert-butyl 5-(3-aminopyridin-4-yl)-2-oxohexahydrooxazolo[4,5-c]pyridine-3(2H)-carboxylate

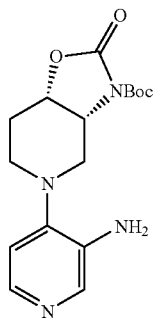

To a solution of (3aR,7aS)-tert-butyl 5-(3-nitropyridin-4-yl)-2-oxohexahydrooxazolo[4,5-c]pyridine-3(2H)-carboxylate in EtOH and EtOAc (1:1, 0.15 M) was added Pd/C (10% by weight) and the reaction was stirred under a hydrogen balloon for 15 h. The solution was filtered through a pad of Celite, and the filtrate was concentrated to yield (3aR,7aS)-tert-butyl 5-(3-aminopyridin-4-yl)-2-oxohexahydrooxazolo[4,5-c]pyridine-3(2H)-carboxylate as a clear oil in >95% yield. LCMS (m/z): 335.0 (MH+), R$_t$=1.68 min.

Synthesis of benzyl 3-azido-4-hydroxypiperidine-1-carboxylate and benzyl 4-azido-3-hydroxypiperidine-1-carboxylate

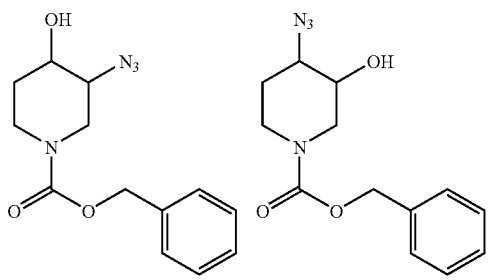

To a solution of benzyl 7-oxa-3-azabicyclo[4.1.0]heptane-3-carboxylate (1.0 equiv.) in MeOH and water (0.17M) was added sodium azide (2.0 equiv.) and ammonium chloride (1.0 equiv.). The reaction was stirred at 65° C. in an oil bath for 7 h, then concentrated to remove the methanol. Ethyl acetate was added, the organic phase was separated, dried with Na$_2$SO$_4$, and concentrated under vacuo to give benzyl 3-azido-4-hydroxypiperidine-1-carboxylate and benzyl 4-azido-3-hydroxypiperidine-1-carboxylate as a clear oil in >95% yield. LCMS (m/z): 276.9 (MH+), R$_t$=2.98 min.

Synthesis of benzyl 3,7-diazabicyclo[4.1.0]heptane-3-carboxylate

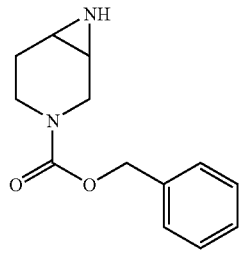

To a solution of benzyl 3-azido-4-hydroxypiperidine-1-carboxylate and benzyl 4-azido-3-hydroxypiperidine-1-carboxylate (1.0 equiv.) in dioxane (0.14M) was added PPh$_3$ (2.0 equiv.) and the reaction was heated to reflux for 1 h. The solution was then concentrated under vacuo and purified via silica gel column chromatography eluting with DCM, 10% MeOH and 1% Et$_3$N to give benzyl 3,7-diazabicyclo[4.1.0]heptane-3-carboxylate as a clear oil in 25% yield. LCMS (m/z): 233.0 (MH+), R$_t$=1.94 min.

Synthesis of benzyl 7-(diethoxyphosphoryl)-3,7-diazabicyclo[4.1.0]heptane-3-carboxylate

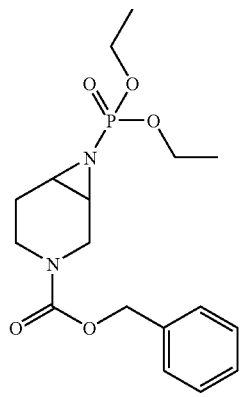

To a solution of benzyl 3,7-diazabicyclo[4.1.0]heptane-3-carboxylate (1.0 equiv.) in DCM (0.26M) was added diethyl phosphorochloridate (1.3 equiv.) and triethyl amine (1.5 equiv.). The reaction was stirred for 24 h, then concentrated to dryness. Added water and ethyl acetate, the organics were extracted, dried with Na$_2$SO$_4$, and concentrated. The crude was purified via silica gel column chromatography eluting with ethyl acetate and hexanes (50% to 100% ethyl acetate) to yield benzyl 7-(diethoxyphosphoryl)-3,7-diazabicyclo[4.1.0]heptane-3-carboxylate as a clear oil in 21% yield. LCMS (m/z): 369.0 (MH+).

Synthesis of benzyl 3-(diethoxyphosphorylamino)-4-methylpiperidine-1-carboxylate

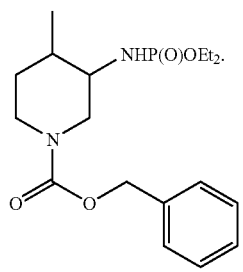

To a suspension of CuI (0.3 equiv.) in anhydrous THF (0.1M) was added methyl magnesium bromide (3M solution in Et$_2$O, 10 equiv.) at −40° C. The reaction was stirred for 30 min, followed by addition of benzyl 7-(diethoxyphosphoryl)-3,7-diazabicyclo[4.1.0]heptane-3-carboxylate (1.0 equiv.) in THF (0.1M) at −40° C. Allowed the reaction to warm to 10° C. over 5 h, then quenched with water and extracted with ethyl acetate. The organic phase was concentrated under vacuo and purified via silica gel column chromatography eluting with ethyl acetate and hexanes (50% to 100% ethyl acetate) to yield benzyl 3-(diethoxyphosphorylamino)-4-methylpiperidine-1-carboxylate in 35% yield. LCMS (m/z): 385.0 (MH$^+$), R$_t$=3.38 min.

Synthesis of diethyl 4-methylpiperidin-3-ylphosphoramidate

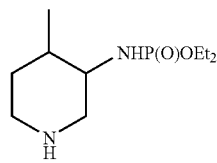

To a solution of benzyl 3-(diethoxyphosphorylamino)-4-methylpiperidine-1-carboxylate (1.0 equiv.) in degassed MeOH was added Pd/C (10% by weight) and the reaction was stirred under a hydrogen atmosphere for 1 h. The solution was filtered, then concentrated to yield diethyl 4-methylpiperidin-3-ylphosphoramidate in 83% yield. LCMS (m/z): 251.1 (MH$^+$).

Synthesis of diethyl 4-methyl-1-(3-nitropyridin-4-yl) piperidin-3-ylphosphoramidate

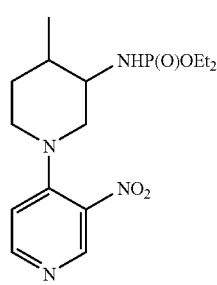

To a solution of diethyl 4-methylpiperidin-3-ylphosphoramidate (1.0 equiv.) in isopropyl alcohol was added 4-chloro-3-nitropyridine (2.0 equiv.) and DIEA (1.1 equiv.). The reaction was heated to 70° C. for 18 h, then quenched with water and extracted with ethyl acetate. The organics were dried and concentrated under vacuo. The crude was purified via ISCO (ethyl acetate and hexanes) to yield diethyl 4-methyl-1-(3-nitropyridin-4-yl)piperidin-3-ylphosphoramidate in 52% yield. LCMS (m/z): 373.0 (MH$^+$), R$_t$=1.93 min.

Synthesis of diethyl 1-(3-aminopyridin-4-yl)-4-methylpiperidin-3-ylphosphoramidate

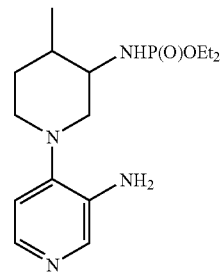

To a solution of diethyl 4-methyl-1-(3-nitropyridin-4-yl) piperidin-3-ylphosphoramidate (1.0 equiv.) in degassed EtOAc (0.1M) was added Pd/C (10% by weight) and the reaction was stirred under a hydrogen atmosphere for 18 h. Filtered and concentrated the filtrate to yield diethyl 1-(3-aminopyridin-4-yl)-4-methylpiperidin-3-ylphosphoramidate in 86% yield. LCMS (m/z): 343.0 (MH$^+$), R$_t$=1.85 min.

Synthesis of benzyl 4-chloro-3-(diethoxyphosphorylamino)piperidine-1-carboxylate

To a solution of benzyl 7-(diethoxyphosphoryl)-3,7-diazabicyclo[4.1.0]heptane-3-carboxylate (1.0 equiv.) and triethyl amine hydrochloride (4 equiv.) in DCM (0.1M) was added BF$_3$.OEt$_2$ (2.0 equiv.) and the reaction was allowed to stir at room temperature for 2 h under a nitrogen atmosphere. The solution was then quenched with water and extracted with DCM. The crude product was purified via silica gel column chromatography (ISCO eluting with EtOAc and Hexanes 50% to 100% EtOAc) to yield benzyl 4-chloro-3-(diethoxyphosphorylamino)piperidine-1-carboxylate in 89% yield. LCMS (m/z): 405.1 (MH$^+$), R$_t$=2.73 min.

Synthesis of diethyl 4-chloropiperidin-3-ylphosphoramidate

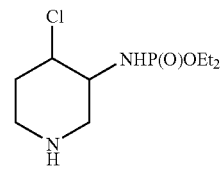

To a solution of benzyl 4-chloro-3-(diethoxyphosphorylamino)piperidine-1-carboxylate (1.0 equiv.) in degassed MeOH was added Pd/C (10% by weight) and the reaction was stirred under a hydrogen atmosphere for 1 h. The solution was filtered, then concentrated to yield diethyl 4-chloropiperidin-3-ylphosphoramidate in 92% yield. LCMS (m/z): 271.0 (MH$^+$).

Synthesis of diethyl 4-chloro-1-(3-nitropyridin-4-yl)piperidin-3-ylphosphoramidate

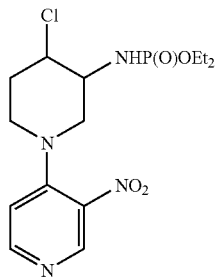

To a solution of diethyl 4-chloropiperidin-3-ylphosphoramidate (1.0 equiv.) in isopropyl alcohol (0.1M) was added 4-chloro-3-nitropyridine (2.0 equiv.) and DIEA (1.1 equiv.). The reaction was heated to 70° C. for 18 h, then quenched with water and extracted with ethyl acetate. The organics were dried and concentrated under vacuo. The crude was purified via ISCO (ethyl acetate and hexanes then 10% methanol in DCM) to yield diethyl 4-chloro-1-(3-nitropyridin-4-yl)piperidin-3-ylphosphoramidate in 69% yield. LCMS (m/z): 393.1 (MH$^+$), $R_f$=2.01 min.

Synthesis of diethyl 1-(3-aminopyridin-4-yl)-4-chloropiperidin-3-ylphosphoramidate

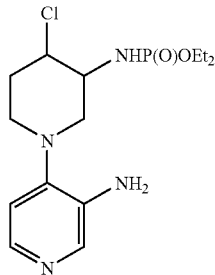

To a solution of diethyl 4-chloro-1-(3-nitropyridin-4-yl)piperidin-3-ylphosphoramidate (1.0 equiv.) in degassed EtOAc (0.1M) was added Pd/C (10% by weight) and the reaction was stirred under a hydrogen atmosphere for 18 h. Filtered and concentrated the filtrate to yield diethyl 1-(3-aminopyridin-4-yl)-4-chloropiperidin-3-ylphosphoramidate in 83% yield. LCMS (m/z): 363.1 (MH$^+$), $R_f$=1.89 min.

Synthesis of 3-oxocyclohex-1-enyl trifluoromethanesulfonate

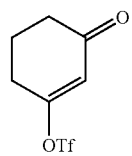

To a solution of cyclohexane-1,3-dione (1 equiv) in DCM (0.4M) was added Na$_2$CO$_3$ (1.0 equiv.) and cooled to 0° C. Added Tf$_2$O (1.0 equiv.) in DCM (5M) dropwise over 1 hr at room temperature under a nitrogen atmosphere. Upon addition, the reaction was stirred for 2 hr (dark red solution). The solution was filtered and to the filtrate was added saturated NaHCO$_3$ (carefully), then extracted the organics, dried with brine, then Na$_2$SO$_4$, and concentrated. The crude was purified via SiO$_2$ column chromatography eluting with DCM and hexanes (1:1) or alternatively via a neutral alumina plug eluting with DCM to afford 3-oxocyclohex-1-enyl trifluoromethanesulfonate in 30% or 67% yield respectively. The triflate decomposes upon storage and should be used immediately for the next reaction. LC/MS=244.9/286.0 (M+H and M+CH$_3$CN); Rt=0.88 min.

Synthesis of 3-(4,4,5,5-tetramethyl-1,3,2-dioxaborolan-2-yl)cyclohex-2-enone

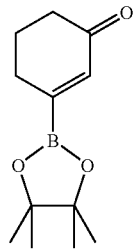

To a solution of 3-oxocyclohex-1-enyl trifluoromethanesulfonate (1.0 equiv.) in degassed dioxane (0.3M) was added bis(pinacolato)diboron (2.0 equiv.), KOAc (3.0 equiv.), and Pd(dppf)Cl$_2$-DCM (0.05 equiv.). The reaction was heated to 80° C. for 2 h, then filtered. The dioxane solution was used for the next step without further purification. LC/MS=140.9 (M+H of boronic acid).

Synthesis of 3-(3-nitropyridin-4-yl)cyclohex-2-enone

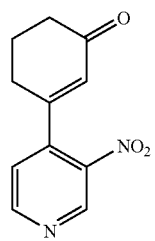

To a solution of 3-(4,4,5,5-tetramethyl-1,3,2-dioxaborolan-2-yl)cyclohex-2-enone (1.0 equiv.) in degassed dioxane and 2M Na$_2$CO$_3$ was added 4-chloro-3-nitropyridine (1.2 equiv.) and Pd(PPh$_3$)$_4$ (0.05 equiv.). The reaction was heated in an oil bath to 120° C. for 30 min. (reaction can also be carried out in the microwave for 10 min at 120° C.). Cooled to room temperature, then diluted with EtOAc, added H$_2$O—dark solution, lots of emulsions. Filtered to get rid of the solids, then extracted the organic phase, dried with Na$_2$SO$_4$, and concentrated. The crude was purified via silica gel chromatography to yield 3-(3-nitropyridin-4-yl)cyclohex-2-enone (64%, 2 steps). LC/MS=219 (M+H), LC=2.29 min.

Synthesis of 3-(3-nitropyridin-4-yl)cyclohex-2-enol

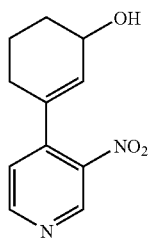

To a solution of 3-(3-nitropyridin-4-yl)cyclohex-2-enone (1.0 equiv.) was added EtOH (1.1 M) and CeCl$_3$·7H$_2$O (1.3 equiv.). The reaction was cooled to 0° C., then NaBH$_4$ (1.3 equiv.) was added in portions. Stirred for 2 h at 0° C., then quenched by adding water, concentrated to remove the EtOH, added EtOAc, extracted the organics, dried with brine, then Na$_2$SO$_4$, and concentrated to yield 3-(3-nitropyridin-4-yl)cyclohex-2-enol (99%). LC/MS=221.1 (M+H), LC=2.24 min.

Synthesis of 2-(3-(3-nitropyridin-4-yl)cyclohex-2-enyl)isoindoline-1,3-dione

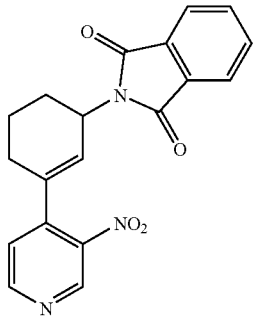

To a homogeneous solution of 3-(3-nitropyridin-4-yl)cyclohex-2-enol (1.0 eq), triphenyl phosphine (1.5 eq), and phthalimide (1.5 eq) in THF (0.2 M) cooled to 0° C., ditert-butyl azodicarboxylate (1.5 eq) in THF was added to the solution. The mixture was stirred at 0° C. for 2 hours. The reaction was concentrated in vacco. The residue was purified by column (5% methanol in 1:1 ethyl acetate and hexanes) to give a solid, which was further triturated with DCM and hexanes to yield pure product, plus filtrate. Further purification of the filtrate yielded more pure product. The total yield of 2-(3-(3-nitropyridin-4-yl)cyclohex-2-enyl)isoindoline-1,3-dione is 58%. LC/MS (m/z): MH$^+$=350.2, Rt=0.96. HPLC Rt=3.73.

Synthesis of 2-(3-(3-aminopyridin-4-yl)cyclohexyl)isoindoline-1,3-dione

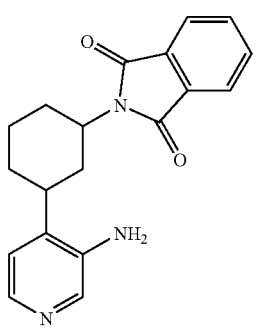

A solution of 2-(3-(3-nitropyridin-4-yl)cyclohex-2-enyl)isoindoline-1,3-dione (1 eq) in Acetic Acid (0.1 M) was purged with nitrogen for 10 min. Then 10% Pd/C (0.15 eq) was added. The reaction mixture was stirred at room temperature for four days under an atmosphere of hydrogen. Solids were removed by filtration over celite, then rinsed with EtOAc and MeOH. The filtrate was concentrated, diluted with EtOAc and washed 2× with sat. aq. 2M Na$_2$CO$_3$. Organic layer was dried with MgSO$_4$, filtered, and concentrated. Triturated from EtOAc/hexanes to give 2-(3-(3-aminopyrin-4-yl)cyclohexyl)isoindoline-1,3-dione in 77% yield. LC/MS (m/z): MH$^+$=322.2, Rt=0.64. HPLC Rt=2.43 min.

Synthesis of 5,5-dimethyl-3-oxocyclohex-1-enyl trifluoromethanesulfonate

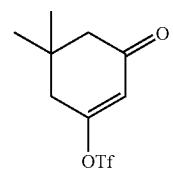

In a 3-neck round bottom flask, 5,5-dimethylcyclohexane-1,3-dione (1.0 eq) was dissolved in DCM (0.2 M). Sodium carbonate (1.1 equiv.) was added and the mixture cooled with magnetic stirring on an ice/salt/water bath to ~−5° C. under N$_2$. Triflic anhydride (1.05 equiv.) diluted in DCM was added drop wise via addition funnel over 90 minutes. Upon completion of addition, the reaction was stirred at ~0° C. for 1 h. From LCMS and $^1$H NMR, there was still starting material left. Additional sodium carbonate (0.51 equiv.) and triflic anhydride (0.50 equiv.) were added. After 2 hours, the mixture was filtered through a coarse frit glass funnel (the cake was washed with DCM), transferred to an Erlenmeyer flask, quenched by careful addition of saturated aqueous sodium bicarbonate with vigorous stirring until pH=7, transferred to a separatory funnel and the layers separated. The organic layer was washed with brine, dried over MgSO$_4$, filtered, concentrated to give 5,5-dimethyl-3-oxocyclohex-1-enyl trifluoromethanesulfonate, which was used to next step without further purification. LC/MS (m/z): MH$^+$=273.1, Rt=1.03 min.

Synthesis of 5,5-dimethyl-3-(4,4,5,5-tetramethyl-1,3,2-dioxaborolan-2-yl)cyclohex-2-enone

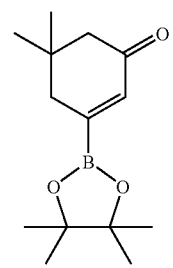

All of reagents 5,5-dimethyl-3-oxocyclohex-1-enyl trifluoromethanesulfonate (1.0 eq), potassium acetate (3.0 eq), and bis(pinacolato)diboron (2.0 eq) were added to 1,4-dioxane (0.2 M) in a round bottom flask and degassed by bubbling $N_2$ through the mixture for 10 min. $PdCl_2$(dppf)-DCM adduct (0.03 eq) was added and the reaction heated to 80° C. fitted with a reflux condenser on an oil bath under $N_2$ overnight. The mixture was cooled to room temperature, filtered through a coarse frit glass funnel, the cake rinsed with 1,4-dioxane to give the 5,5-dimethyl-3-(4,4,5,5-tetramethyl-1,3,2-dioxaborolan-2-yl)cyclohex-2-enone in 1,4-dioxane which was used to next step without further purification. LC/MS (m/z): $MH^+$ (boronic acid)=169.1, Rt=0.50 min.

Synthesis of 5,5-dimethyl-3-(3-nitropyridin-4-yl)cyclohex-2-enone

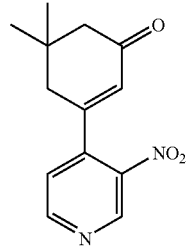

The boronate ester 5,5-dimethyl-3-(4,4,5,5-tetramethyl-1,3,2-dioxaborolan-2-yl)cyclohex-2-enone (1.0 eq) was dissolved in 1,4-dioxane in a round bottom flask was degassed by bubbling $N_2$ through the solution for 30 minutes. 4-chloro-3-nitro-pyridine (1.3 eq) and 2M(aq) sodium carbonate (2.0 eq) were added and $N_2$ was bubbled through for 10 minutes and then $PdCl_2$(dppf)-DCM (0.05 eq) was added. The reaction mixture was stirred at 110° C. for 2 hr. The mixture was added EtOAc and water. The resulting mixture was filtered through celite, the cake was washed with EtOAc. The organic layer was separated. The aqueous was extracted with EtOAc. The combined organic layers were washed with brine, dried over $MgSO_4$, concentrated. The residue was purified by silica gel chromatography (eluted with EtOAc:Hexanes=1:10 to 2:1) to give 5,5-dimethyl-3-(3-nitropyridin-4-yl)cyclohex-2-enone (46.7% for three steps). LC/MS (m/z): $MH^+$=247.2, Rt=0.79 min.

Synthesis of 5,5-dimethyl-3-(3-nitropyridin-4-yl)cyclohex-2-enol

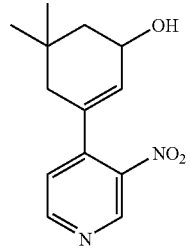

To a solution of 5,5-dimethyl-3-(3-nitropyridin-4-yl)cyclohex-2-enone (1.0 eq), and $CeCl_3$-$7H_2O$ (1.2 eq) in MeOH (0.2 M) was added $NaBH_4$ (1.0 eq) at 0° C. The solution was stirred for 1 hour, and then quenched by 5 mL of water. The volatiles were removed in vacuum and the residue was partitioned between EtOAc and $H_2O$. The organic layer was separated and washed with brine. The combined aqueous was back extracted with EtOAc and the organic was washed with brine. The combined organics were dried over $MgSO_4$, filtered and concentrated. The residue was purified by column (5% methanol in 1:1 ethyl acetate and hexanes) to give 5,5-dimethyl-3-(3-nitropyridin-4-yl)cyclohex-2-enol (74%). LC/MS (m/z): $MH^+$=249.2, Rt=0.76 min.

Synthesis of 2-(5,5-dimethyl-3-(3-nitropyridin-4-yl)cyclohex-2-enyl)isoindoline-1,3-dione

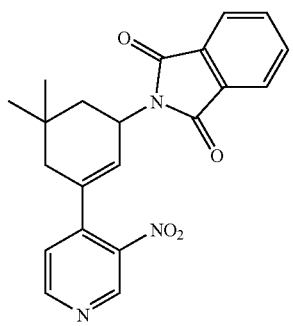

To a homogeneous solution of 5,5-dimethyl-3-(3-nitropyridin-4-yl)cyclohex-2-enol (1.0 eq), triphenyl phosphine (1.5 eq), and phthalimide (1.5 eq) in THF (0.2 M) cooled to 0° C., ditertbutyl azodicarboxylate (1.5 eq) in THF was added to the solution. The mixture was stirred at 0° C. for 2 hours. The reaction was concentrated in vacco. The residue was purified by column (5% methanol in 1:1 ethyl acetate and hexanes) to give 2-(5,5-dimethyl-3-(3-nitropyridin-4-yl)cyclohex-2-enyl)isoindoline-1,3-dione (99%). LC/MS (m/z): $MH^+$=378.2, Rt=1.10 min.

Synthesis of 2-(3-(3-aminopyridin-4-yl)-5,5-dimethylcyclohex-2-enyl)isoindoline-1,3-dione

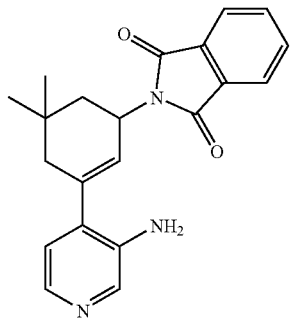

A solution of 2-(5,5-dimethyl-3-(3-nitropyridin-4-yl)cyclohex-2-enyl)isoindoline-1,3-dione (1 eq) in Acetic Acid (0.1 M) was purged with nitrogen for 10 min. Then 10% Pd/C (0.10 eq) was added. The reaction mixture was stirred at room temperature overnight an atmosphere of hydrogen. Solids were removed by filtration over celite, then rinsed with EtOAc and MeOH. The filtrate was concentrated, diluted with EtOAc and washed 2× with sat. aq. 2M $Na_2CO_3$. Organic layer was dried with MgSO$_4$, filtered, and concentrated. The residue was purified by column (5% methanol in 1:1 ethyl acetate and hexanes) to give 2-(3-(3-aminopyridin-4-yl)-5,5-dimethylcyclohex-2-enyl)isoindoline-1,3-dione (89%). LC/MS (m/z): MH$^+$=348.3, Rt=0.79 min.

Synthesis of 2-(5-(3-aminopyridin-4-yl)-3,3-dimethylcyclohexyl)isoindoline-1,3-dione

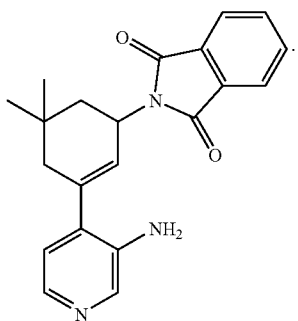

A solution of 2-(3-(3-aminopyridin-4-yl)-5,5-dimethylcyclohex-2-enyl)isoindoline-1,3-dione (1.0 eq) in acetic acid (0.1 M) was purged with nitrogen for 10 min. Then 10% Pd/C (0.1 eq) was added. The reaction mixture was stirred at 45° C., 300 psi hydrogen atmosphere in a steel bomb overnight and at 65° C., 300 psi for 5 hours. Solids were removed by filtration over celite, then rinsed with EtOAc and MeOH. The filtrate was concentrated, diluted with EtOAc and washed 2× with sat. aq. 2M Na$_2$CO$_3$. Organic layer was dried with MgSO$_4$, filtered, and concentrated. The residue was purified by column (5% methanol in 1:1 ethyl acetate and hexanes) to give 2-(5-(3-aminopyridin-4-yl)-3,3-dimethylcyclohexyl)isoindoline-1,3-dione (53%). LC/MS (m/z): MH$^+$=350.3, Rt=0.78 min. The enantiomerically pure 2-((1R,5R)-5-(3-aminopyridin-4-yl)-3,3-dimethylcyclohexyl)isoindoline-1,3-dione and 2-((1S,5S)-5-(3-aminopyridin-4-yl)-3,3-dimethylcyclohexyl)isoindoline-1,3-dione were resolved by chiral HPLC (For analysis R$_t$=7.53 min and 13.11 min respectively; hexanes:ethanol=80:20 (v:v), Chiralcel OJ-H 100×4.6 mm at 1 mL/min. For preparative separation, hexanes:ethanol=80:20 (v:v), Chiralcel OJ-H 250×20 mm at 20 mL/min ). $^1$H NMR (CDCl$_3$): δ 8.04 (s, 1H), 8.00 (d, 1H), 7.82 (m, 2H), 7.71 (m, 2H), 7.06 (d, 1H), 4.54 (m, 1H), 3.71 (m, 2H), 2.89 (m, 1H), 2.23-2.44 (m, 2H), 1.90 (m, 1H), 1.20-1.60 (m, 3H), 1.18 (s, 3H), 1.07 (s, 3H).

Synthesis of 5-methyl-3-oxocyclohex-1-enyltrifluoromethanesulfonate

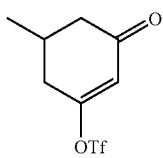

To a solution of 5-methylcyclohexane-1,3-dione (1 equiv) in DCM (0.4M) was added Na$_2$CO$_3$ (1.0 equiv.) and cooled to 0° C. Added Tf$_2$O (1.0 equiv.) in DCM (5M) dropwise over 1 hr at 0° C. under a nitrogen atmosphere. Upon addition, the reaction was stirred for 2 hr at room temperature (dark red solution). The solution was filtered and to the filtrate was added saturated NaHCO$_3$ (carefully), then extracted the organics, dried with brine, then Na$_2$SO$_4$, and concentrated. The crude was purified via SiO$_2$ column chromatography eluting with DCM and hexanes (1:1) or alternatively via a neutral alumina plug eluting with DCM to afford 5-methyl-3-oxocyclohex-1-enyl trifluoromethanesulfonate in 30% or 67% yield respectively. The triflate decomposes upon storage and should be used immediately for the next reaction. LC/MS=259.1/300.1 (M+H and M+CH$_3$CN); Rt=0.94 min, LC=3.84 min.

Synthesis of 5-methyl-3-(4,4,5,5-tetramethyl-1,3,2-dioxaborolan-2-yl)cyclohex-2-enone

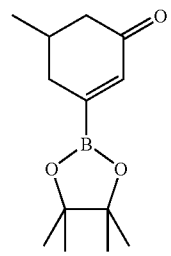

To a solution of 5-methyl-3-oxocyclohex-1-enyl trifluoromethanesulfonate (1.0 equiv.) in degassed dioxane (0.3M) was added bis(pinacolato)diboron (2.0 equiv.), KOAc (3.0 equiv.), and Pd(dppf)Cl$_2$-DCM (0.05 equiv.). The reaction was heated to 80° C. for 10 h, then filtered. The dioxane solution was used for the next step without further purification. LC/MS=155.1 (M+H of boronic acid); Rt=0.41 min, LC=1.37 min.

Synthesis of 5-methyl-3-(3-nitropyridin-4-yl)cyclohex-2-enone

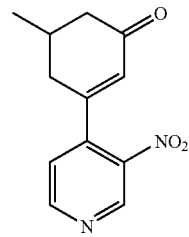

To a solution of 5-methyl-3-(4,4,5,5-tetramethyl-1,3,2-dioxaborolan-2-yl)cyclohex-2-enone (1.0 equiv.) in degassed dioxane and 2M Na$_2$CO$_3$ was added 4-chloro-3-nitropyridine (1.2 equiv.) and Pd(PPh$_3$)$_4$ (0.05 equiv.). The reaction was heated in an oil bath to 120° C. for 2 h. (reaction can also be carried out in the microwave for 10 min at 120° C.). Cooled to room temperature, then diluted with EtOAc, added H$_2$O—dark solution, lots of emulsions. Filtered to get rid of the solids, then extracted the organic phase, dried with Na$_2$SO$_4$, and concentrated. The crude was purified via silica gel chromatography to yield 5-methyl-3-(3-nitropyridin-4-yl)cyclohex-2-enone. LC/MS=233.2 (M+H); Rt=0.69 min, LC=2.70 min.

Synthesis of cis-(+/−)-5-methyl-3-(3-nitropyridin-4-yl)cyclohex-2-enol

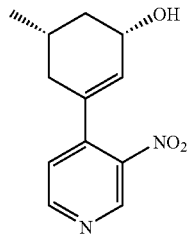

To a solution of 5-methyl-3-(3-nitropyridin-4-yl)cyclohex-2-enone (1.0 equiv.) was added EtOH (1.1 M) and CeCl$_3$·7H$_2$O (1.3 equiv.). The reaction was cooled to 0° C., then NaBH$_4$ (1.3 equiv.) was added in portions. Stirred for 2 h at 0° C., then quenched by adding water, concentrated to remove the EtOH, added EtOAc, extracted the organics, dried with brine, then Na$_2$SO$_4$, and concentrated to yield 5-methyl-3-(3-nitropyridin-4-yl)cyclohex-2-enol (91%). LC/MS=235.2 (M+H), LC=2.62 min.

Synthesis of cis-(+/−)-4-(3-(tert-butyldimethylsilyloxy)-5-methylcyclohex-1-enyl)-3-nitropyridine

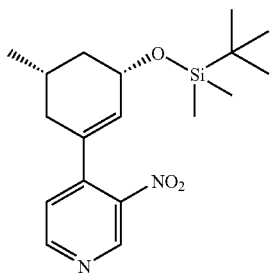

To a solution of 5-methyl-3-(3-nitropyridin-4-yl)cyclohex-2-enol (1.0 equiv.) in DMF (0.5 M) was added imidazole (4.0 equiv.) and TBDSMCl (2.5 equiv.). After stirring for 18 hours the solution was portioned between EtOAc and H$_2$O and separated. After washing further with H$_2$O (3×) and NaCl$_{(sat.)}$, drying over MgSO4, filtering and removal of solvents, 4-(3-(tert-butyldimethylsilyloxy)-5-methylcyclohex-1-enyl)-3-nitropyridine was obtained (85%). LC/MS=349.2 (M+H), LC=5.99 min.

Synthesis of cis-(+/−)-4-(3-(tert-butyldimethylsilyloxy)-5-methylcyclohexyl)pyridin-3-amine

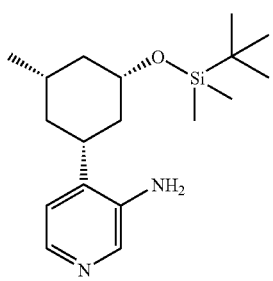

To a solution of cis-(tert-butyldimethylsilyloxy)-5-methylcyclohex-1-enyl)-3-nitropyridine (1.0 equiv.) in methanol, at a concentration of 0.1 M, was added 10% palladium on carbon (0.1 eq.). The resultant heterogeneous solution was put under an atmosphere of hydrogen and was stirred for 15 hours. At this time the mixture was filtered through a pad of celite eluting with methanol. The volatiles were removed in vacuo yielding all cis-4-(3-(tert-butyldimethylsilyloxy)-5-methylcyclohexyl)pyridin-3-amine (90%). LCMS (m/z): 321.3 (MH$^+$); LC R$_t$=3.85 min.

Synthesis of cis(+/−)benzyl 4-(3-(tert-butyldimethylsilyloxy)-5-methylcyclohexyl)pyridin-3-ylcarbamate

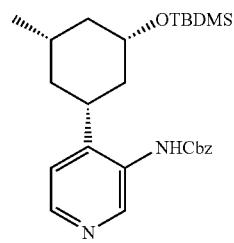

To a solution of cis-(+/−)-4-(3-(tert-butyldimethylsilyloxy)-5-methylcyclohexyl)pyridin-3-amine in dichloromethane at a concentration of 0.5M was added benzyl 2,5-dioxopyrrolidin-1-yl carbonate (1.1 equiv.) and DMAP (0.05 equiv.). After stirring for 16 hours at rt, additional benzyl 2,5-dioxopyrrolidin-1-yl carbonate (0.55 equiv.) and DMAP (0.03 equiv.) were added. After stirring for an additional 24 hours at rt, additional benzyl 2,5-dioxopyrrolidin-1-yl carbonate (0.1 equiv.) and DMAP (0.03 equiv.) were added. After stirring for 18 more hours the solution was partitioned between EtOAc and Na$_2$CO$_{3(sat.)}$ and separated. Upon further washing with Na$_2$CO$_{3(sat.)}$ (2×) and NaCl$_{(sat.)}$, drying over MgSO$_4$, filtering and removal of solvents, cis(+/−)benzyl 4-(3-(tert-butyldimethylsilyloxy)-5-methylcyclohexyl)pyridin-3-ylcarbamate was obtained. The crude material was used as is. LC/MS=455.3 (M+H), LC=4.39 min.

Synthesis of cis-(+/−)benzyl 4-(3-hydroxy-5-methylcyclohexyl)pyridin-3-ylcarbamate

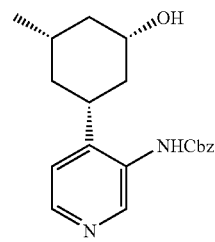

A solution of cis(+/−)benzyl 4-(3-(tert-butyldimethylsilyloxy)-5-methylcyclohexyl)pyridin-3-ylcarbamate in 1:2:1 6N HCl/THF/MeOH at a concentration of 0.1 M was stirred at rt for 6 hours. The pH was than adjusted to pH=7 by addition of 6N NaOH and the volatiles were removed in vacuo. The aqueous layer was extracted with EtOAc and the organic was washed with NaCl$_{(sat.)}$. dried over MgSO$_4$, filtered and upon removal of the volatiles in vacuo, cis-(+/−)benzyl 4-(3-hydroxy-5-methylcyclohexyl)pyridin-3-ylcarbamate was obtained. The crude material was used as is. LC/MS=341.2 (M+H), LC=2.38 min.

Synthesis of cis(+/−)-benzyl 4-(3-methyl-5-oxocyclohexyl)pyridin-3-ylcarbamate

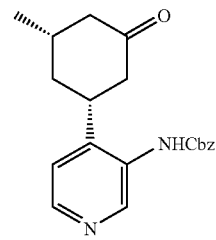

To a 0° C. solution of cis-(+/−)-benzyl 4-(3-hydroxy-5-methylcyclohexyl)pyridin-3-ylcarbamate in wet $CH_2Cl_2$ at a concentration of 0.16 M was added Dess-Martin Periodinane (1.5 equiv.) and the solution was stirred for 18 hours as it warmed to rt. The solution was partitioned between EtOAc and 1:1 10% $Na_2S_2O_3$/$NaHCO_{3(sat.)}$ and separated. Upon further washing with 1:1 10% $Na_2S_2O_3$/$NaHCO_{3(sat.)}$ (2×) and $NaCl_{(sat.)}$, drying over $MgSO_4$, filtering, removal of solvents and purification by silica gel chromatography (75-100% EtOAc/hexanes), cis-(+/−)-benzyl-4-(3-methyl-5-oxocyclohexyl)pyridin-3-ylcarbamate was obtained as a white solid (53%, 5 steps). LC/MS=339.2 (M+H).

Synthesis of cis-(+/−)-benzyl 4-(-3-(benzylamino)-5-methylcyclohexyl)pyridin-3-ylcarbamate

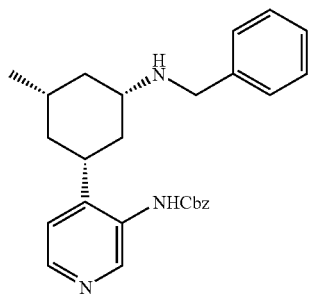

A solution of cis-(+/−)-benzyl-4-(3-methyl-5-oxocyclohexyl)pyridin-3-ylcarbamate (1.0 equiv) and benzylamine (3.0 equiv) in MeOH, at a concentration of 0.25 M, was stirred at rt for 2 hours. Upon cooling in a −78° C. bath, $LiBH_4$ (1.1 equiv, 2.0 M in THF) was added and the solution was allowed to warm to rt with stirring over 16 hours. The solution was partitioned between EtOAc and $NaHCO_{3(sat.)}$, separated, washed further with $NaHCO_{3(sat.)}$ and $NaCl_{(sat.)}$, dried over $MgSO_4$, filtered and the after removal of volatiles in vacuo, cis-(+/−)-benzyl 4-(-3-(benzylamino)-5-methylcyclohexyl) pyridin-3-ylcarbamate was obtained as a 4:1 mixture of isomers, with the all cis as predominant LC/MS=430.3 (M+H), LC=0.62 min.

Synthesis of cis(+/−)-tert-butyl(-3-(3-aminopyridin-4-yl)-5-methylcyclohexylcarbamate

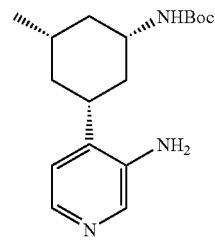

To a solution of cis-(+/−)-benzyl 4-(-3-(benzylamino)-5-methylcyclohexyl)pyridin-3-ylcarbamate was (1.0 equiv.) in methanol, at a concentration of 0.07 M, was added 20% palladium hydroxide on carbon (0.2 eq.). The resultant heterogeneous solution was put under an atmosphere of hydrogen and was stirred for 14 hours. At this time the reaction was purged with Ar, $Boc_2O$ (1.0 equiv.) was added and the solution was stirred for 8 hours. Additional $Boc_2O$ (1.0 equiv.) was added and the solution was stirred for 16 more hours. At this time the mixture was filtered through a pad of celite eluting with methanol. Upon removal of volatiles in vacuo, purification by silical gel chromatography (2.5-2.5 MeOH/$CH_2Cl_2$ with 0.1% DIEA) and recrystallization from 10% EtOAc/hexanes yielded cis(+/−)-tert-butyl(-3-(3-aminopyridin-4-yl)-5-methylcyclohexylcarbamate (49%). LCMS (m/z): 306.3 (MH$^+$), LC $R_t$=2.59 min. Pure enantiomers could be obtained by chiral chromatography.

Synthesis of 4-(cyclohexa-1,3-dienyl)-3-nitropyridine

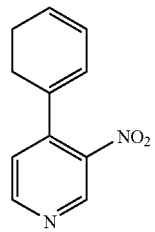

To a solution of 3-(3-nitropyridin-4-yl)cyclohex-2-enol (1.0 equiv.) was added dioxane (0.18M) and p-TSA (1.1 equiv.). The solution was heated to 100° C. for 4 h. Cooled to room temperature, worked up with sat. $NaHCO_3$ and ethyl acetate, the organic phase was dried with $Na_2SO_4$ and concentrated. The crude was purified via silica gel column chromatography eluting with 100% DCM to give 4-(cyclohexa-1,3-dienyl)-3-nitropyridine as a yellow oil (27% yield). LCMS (m/z): 203.1 (MH$^+$), LC $R_t$=3.53 min, H-NMR ($CDCl_3$): 9.02 (s, 1H), 8.70 (d, J=5.3, 1H), 7.30 (d, J=5.3, 1H), 6.15-6.17 (m, 1H), 6.02-6.11 (m, 2H), 2.35-2.38 (m, 4H).

Synthesis of tert-butyl 6-hydroxy-3-(3-nitropyridin-4-yl)cyclohex-2-enylcarbamate

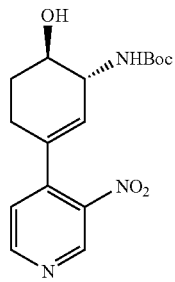

To a solution of 2-azido-4-(3-nitropyridin-4-yl)cyclohex-3-enol (1.0 equiv.) in Pyridine and NH$_4$OH (8:1, 0.23 M) was added trimethylphosphine (3.0 equiv.) at room temperature. The mixture was stirred at room temperature for 3 hours. Solvents were removed. To the residue was added ethanol. Then ethanol was removed in vacuo to ensure removal of the ammonia totally. The residue was dissolved in 1,4-Dioxane and sat. aq. sodium bicarbonate, and then Boc$_2$O (1.0 eq) in THF were added to the mixture. The resulting mixture was stirred at room temperature for 2 hours. The reaction mixture was diluted with ethyl acetate, and washed with sat NaCl. The organic was dried with MgSO$_4$, filtered and concentrated. The residue was purified by column (5% methanol in 1:1 ethyl acetate and hexanes) to give tert-butyl 6-hydroxy-3-(3-nitropyridin-4-yl)cyclohex-2-enylcarbamate (82%). LC/MS (m/z): MH$^+$=336.0, Rt=0.71

Synthesis of (+/−)-4-(3-azido-4-(tert-butyldimethylsilyloxy)cyclohex-1-enyl)-3-nitropyridine

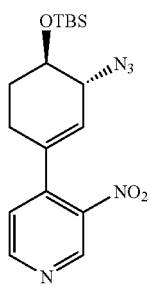

To a solution of (+/−)-2-azido-4-(3-nitropyridin-4-yl)cyclohex-3-enol (1.0 equiv.) in DCM (0.15M) was added TBSCl (2.0 equiv.), imidazole (2.0 equiv.) and DMAP (0.1 equiv.) at room temperature. After 18 h, water was added, the organics were dried with brine, then Na$_2$SO$_4$, and concentrated. The crude material was loaded to silica gel and purified via ISCO eluting with ethyl acetate and hexanes (20%). Obtained (+/−)-4-(3-azido-4-(tert-butyldimethylsilyloxy)cyclohex-1-enyl)-3-nitropyridine as a yellow oil in 60% yield. LCMS (m/z): 376.3 (MH$^+$), LC R$_t$=5.848 min.

Synthesis of (+/−)-tert-butyl 6-(tert-butyldimethylsilyloxy)-3-(3-nitropyridin-4-yl)cyclohex-2-enylcarbamate

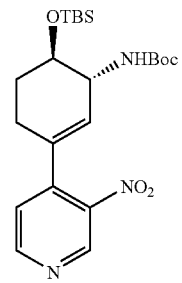

In a round-bottomed flask was added (+/−)-4-(3-azido-4-(tert-butyldimethylsilyloxy)cyclohex-1-enyl)-3-nitropyridine (1.0 equiv.) and pyridine (0.1M) to give a yellow solution. Ammonium hydroxide (10:1 pyridine:ammonium hydroxide) was added followed by PMe$_3$ (3.0 equiv.). The reaction turned dark brown after 10 min. Stirred at room temperature for 1.5 h. Quenched by adding EtOH, and concentrated. Repeated 2 more times. To the crude was added sat. NaHCO$_3$ and dioxane (1:1, 0.1M). Boc$_2$O (1.0 equiv.) was added. Stirred for one hour at room temperature. Washed with H$_2$O and EtOAc, the organic phase was dried with MgSO$_4$, filtered and concentrated. The residue was purified via ISCO (5:1 Hex/EtOAc). Collected the pure fractions and concentrated to give (+)-tert-butyl 6-(tert-butyldimethylsilyloxy)-3-(3-nitropyridin-4-yl)cyclohex-2-enylcarbamate as a foam. LCMS (m/z): 450.3 (MH$^+$), LC R$_t$=5.83 min.

Synthesis of (+/−)-tert-butyl 3-(3-aminopyridin-4-yl)-6-(tert-butyldimethylsilyloxy)cyclohex-2-enylcarbamate

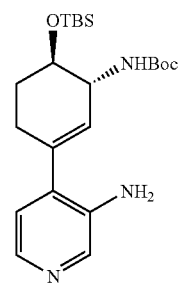

To a solution of (+/−)-tert-butyl 6-(tert-butyldimethylsilyloxy)-3-(3-nitropyridin-4-yl)cyclohex-2-enylcarbamate (1.0 equiv.) in AcOH (0.18 M) was added Fe (6.0 equiv.) and the reaction was stirred for 20 h. Worked up by diluting the reaction with methanol, filtered, and concentrated the filtrate. To the crude was added ethyl acetate and saturated NaHCO$_3$, the organics were dried with sodium sulfate and concentrated to give (+/−)-tert-butyl 3-(3-aminopyridin-4-yl)-6-(tert-butyldimethylsilyloxy)cyclohex-2-enylcarbamate as a yellow oil in 94% yield. LCMS (m/z): 420.3 (MH$^+$), LC R$_t$=3.88 min.

Synthesis of (+/−)-tert-butyl 5-(3-aminopyridin-4-yl)-2-(tert-butyldimethylsilyloxy)cyclohexylcarbamate

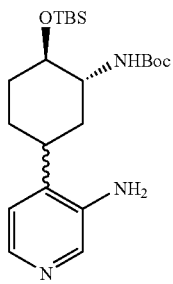

To a solution of (+/−)-tert-butyl 3-(3-aminopyridin-4-yl)-6-(tert-butyldimethylsilyloxy)cyclohex-2-enylcarbamate (1.0 equiv.) in MeOH (0.1M) was added Pd/C (20% by wt) and the reaction was stirred under a hydrogen balloon for 18 h. LC/MS of the reaction indicated mixture of diastereomers, the reaction was filtered, washed with EtOAc and concentrated the filtrate. The crude material was purified via prep-HPLC (in DMSO), and the pure fractions were combined, neutralized with solid NaHCO$_3$, extracted with ethyl acetate, washed with brine, dried under Na$_2$SO$_4$, and concentrated to give product A (8% yield) and product B (51% yield).

Product A: LCMS (m/z): 422.4 (MH$^+$), LC R$_t$=3.75 min.
Product B: LCMS (m/z): 422.4 (MH$^+$), LC R$_t$=3.94 min.

Synthesis of 2-(tert-butoxycarbonylamino)-4-(3-nitropyridin-4-yl)cyclohex-3-enyl methanesulfonate

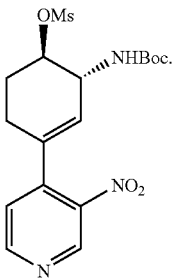

To a solution of tert-butyl 6-hydroxy-3-(3-nitropyridin-4-yl)cyclohex-2-enylcarbamate (1.0 equiv.) and triethyl amine (1.5 equiv.) in CH$_2$Cl$_2$ (0.2 M) was added methanesulfonyl chloride (1.2 equiv.) at 0° C. The mixture was stirred for 2 hours at that temperature. The reaction mixture was diluted with ethyl acetate, and washed with sat NaCl. The organic was dried with MgSO$_4$, filtered and concentrated to give 2-(tert-butoxycarbonylamino)-4-(3-nitropyridin-4-yl)cyclohex-3-enyl methanesulfonate (85%), which was used in the next step without further purification. LC/MS (m/z): MH$^+$=414.0, Rt=0.82

Synthesis of (+/−)-5-(3-nitropyridin-4-yl)-3,3a,7,7a-tetrahydrobenzo[d]oxazol-2(6H)-one The mixture of 2-(tert-butoxycarbonylamino)-4-(3-nitropyridin-4-yl)cyclohex-3-enyl methanesulfonate (1.0 equiv.) in pyridine (0.21 M) was stirred at 110° C. for 10 min in microwave. Pyridine was removed under reduced pressure. The residue was dissolved in ethyl acetate, and washed with sat NaCl. The organic was dried with MgSO$_4$, filtered and concentrated to give 5-(3-nitropyridin-4-yl)-3,3a,7,7a-tetrahydrobenzo[d]oxazol-2(6H)-one (85%), which was used in the next step without further purification. LC/MS (m/z): MH$^+$=262.1, Rt=0.49

Synthesis of (+/−)-tert-butyl 5-(3-nitropyridin-4-yl)-2-oxo-3a,6,7,7a-tetrahydrobenzo[d]oxazole-3(2H)-carboxylate

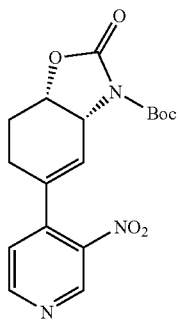

To a solution of 5-(3-nitropyridin-4-yl)-3,3a,7,7a-tetrahydrobenzo[d]oxazol-2(6H)-one (1.0 equiv.), TEA (1.8 equiv.), and catalytic amount DMAP in CH$_2$Cl$_2$ (0.19 M) was added di-tert-butyl dicarbonate (1.2 eqiv) at room temperature. The reaction mixture was stirred for 1 hour. The reaction mixture was diluted with ethyl acetate (100 mL), and washed with sat NaCl (30 mL). The organic was dried with MgSO$_4$, filtered and concentrated. The residue was purified by column (5% methanol in 1:1 ethyl acetate and hexanes) to give tert-butyl 5-(3-nitropyridin-4-yl)-2-oxo-3a,6,7,7a-tetrahydrobenzo[d]oxazole-3(2H)-carboxylate (98%). LC/MS (m/z): MH$^+$=306.0, Rt=0.75

Synthesis of (+/−)-tert-butyl 5-(3-aminopyridin-4-yl)-2-oxohexahydrobenzo[d]oxazole-3(2H)-carboxylate

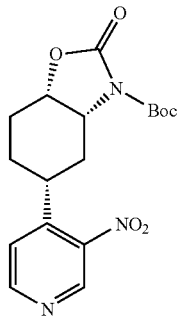

To a solution of tert-butyl 5-(3-nitropyridin-4-yl)-2-oxo-3a,6,7,7a-tetrahydrobenzo[d]oxazole-3(2H)-carboxylate (1.0 equiv.) in methanol and ethyl acetate (1;1, 0.1 M) was added Pd/C (10%). The resulting mixture was stirred under $H_2$ atmosphere for 6 hours. The solid was removed by filtration. The filtrate was concentrated under reduced pressure to give tert-butyl 5-(3-aminopyridin-4-yl)-2-oxohexahydrobenzo[d]oxazole-3(2H)-carboxylate (87%), which was used in the next step without further purification. LC/MS (m/z): MH$^+$=334.1, Rt=0.51.

Synthesis of (+/−)-4-(5-methylcyclohexa-1,3-dienyl)-3-nitropyridine

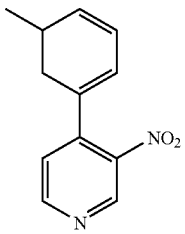

To a solution of 5-methyl-3-(3-nitropyridin-4-yl)cyclohex-2-enol (1.0 equiv.) in dioxane (0.1M) was added p-TSA (1.0 equiv.), and the reaction was stirred at 100° C. for 3 h. The solution was cooled to room temperature, then passed through a pad of neutral alumina eluting with EtOAc to yield (+/−)-4-(5-methylcyclohexa-1,3-dienyl)-3-nitropyridine as a yellow oil in 68% yield. LC/MS=217.1 (M+H), LC=3.908 min.

Synthesis of (+/−)-6-bromo-5-methyl-3-(3-nitropyridin-4-yl)cyclohex-2-enol

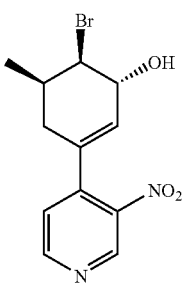

To a solution of 4-(5-methylcyclohexa-1,3-dienyl)-3-nitropyridine (1.0 equiv.) in THF and water (1:1, 0.13M) was added NBS (1.5 equiv.) and the reaction was stirred at room temperature for 30 min. Upon completion, ethyl acetate and water were added to the reaction, the organic phase was dried with brine, then sodium sulfate, filtered, and concentrated. The crude material was purified via silica gel column chromatography eluting with ethyl acetate and hexanes (1:1) to give (+/−)-6-bromo-5-methyl-3-(3-nitropyridin-4-yl)cyclohex-2-enol as a yellow oil in 80% yield. LC/MS=315.0/313.0 (M+H), LC=2.966 min.

Synthesis of (+/−)-2-azido-6-methyl-4-(3-nitropyridin-4-yl)cyclohex-3-enol

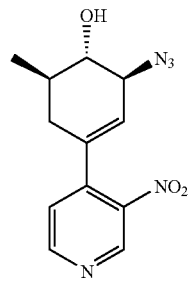

To a solution of (+/−)-6-bromo-5-methyl-3-(3-nitropyridin-4-yl)cyclohex-2-enol (1.0 equiv.) in THF (0.1M) was added potassium tert-butoxide (1.5 equiv.). The reaction turned from orange to black almost immediately. By TLC, the formation of product is clean in 30 min. Quenched by adding saturated ammonium chloride and ethyl acetate. The organic phase was dried with brine, then sodium sulfate, filtered, and concentrated. The crude product was dissolved in ethanol and water (3:1, 0.1M), and ammonium chloride (2.0 equiv) and sodium azide (2.0 equiv.) were added. The dark orange reaction was stirred at room temperature overnight. The conversion to product is clean as indicated by LC/MS. The reaction was concentrated to remove the ethanol, ethyl acetate and water were added, the organic phase was dried with sodium sulfate, filtered, and concentrated. The crude material was purified via silica gel column chromatography eluting with ethyl acetate and hexanes (1:1) to give (+/−)-2-azido-6-methyl-4-(3-nitropyridin-4-yl)cyclohex-3-enol in 55% yield. LC/MS=276.0 (M+H), LC=2.803 min.

Synthesis of (+/−)-tert-butyl 6-hydroxy-5-methyl-3-(3-nitropyridin-4-yl)cyclohex-2-enylcarbamate

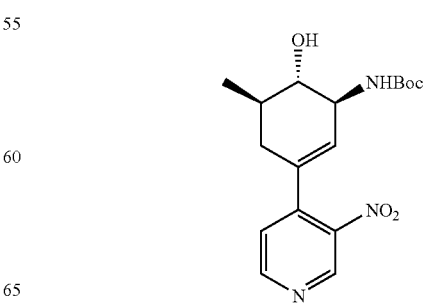

To a solution of (+/−)-2-azido-6-methyl-4-(3-nitropyridin-4-yl)cyclohex-3-enol (1.0 equiv.) in pyridine and ammonium hydroxide (8:1, 0.08 M) was added trimethylphosphine (3.0 equiv.) and the brown solution was stirred at room temperature for 2 h. Upon completion, EtOH was added and the solution was concentrated in vacuo. More ethanol was added and the reaction was concentrated again. Dioxane and sat. NaHCO$_3$ (1:1, 0.08M) were added to the crude, followed by Boc$_2$O (1.0 equiv.). Stirred the reaction mixture at room temperature for 2 h, then added water and ethyl acetate. The organic phase was dried with MgSO$_4$, and concentrated. The crude product was purified via silica gel column chromatography eluting with ethyl acetate and hexanes (1:1) to afford (+/−)-tert-butyl 6-hydroxy-5-methyl-3-(3-nitropyridin-4-yl)cyclohex-2-enylcarbamate (59%). LC/MS=350.1 (M+H), Rt: 0.76 min.

Synthesis of (+/−)-2-(tert-butoxycarbonylamino)-6-methyl-4-(3-nitropyridin-4-yl)cyclohex-3-enyl acetate

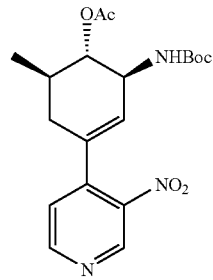

To a solution of (+/−)-tert-butyl 6-hydroxy-5-methyl-3-(3-nitropyridin-4-yl)cyclohex-2-enylcarbamate (1.0 equiv.) in pyridine (0.1M) was added Ac2O (2.0 equiv.) and the reaction was stirred at room temperature overnight. Upon completion, the reaction was concentrated to dryness, then worked-up with ethyl acetate and water. The organic phase was dried with brine, then sodium sulfate, filtered, and concentrated to give (+/−)-2-(tert-butoxycarbonylamino)-6-methyl-4-(3-nitropyridin-4-yl)cyclohex-3-enyl acetate in 94% yield. LC/MS=392.2 (M+H), Rt=0.94 min.

Synthesis of (+/−)-4-(3-aminopyridin-4-yl)-2-(tert-butoxycarbonylamino)-6-methylcyclohexyl acetate

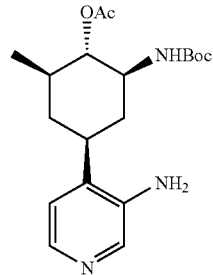

To a degassed solution of (+/−)-2-(tert-butoxycarbonylamino)-6-methyl-4-(3-nitropyridin-4-yl)cyclohex-3-enyl acetate (1.0 equiv.) in MeOH and EtOAc (1:1, 0.1M) was added Pd/C (0.1 equiv.) and the reaction was stirred at room temperature under a hydrogen balloon for 3 days. Upon completion, the solution was filtered through a pad of Celite, the pad was washed with ethyl acetate and the filtrate was concentrated. The crude material contained about 10% of the undesired isomer. The crude was dissolved in ethyl acetate (~20%) and hexanes and heated until all dissolved. The solution was allowed to sit at room temperature for 2 days. The precipitate was then collected to give (+/−)-4-(3-aminopyridin-4-yl)-2-(tert-butoxycarbonylamino)-6-methylcyclohexyl acetate as the pure product in 59% yield. LC/MS=364.3 (M+H), Rt=0.63 min.

Synthesis of 2-(tert-butoxycarbonylamino)-6-methyl-4-(3-nitropyridin-4-yl)cyclohex-3-enyl methanesulfonate

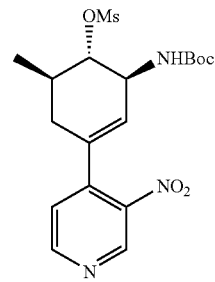

To a solution of tert-butyl 6-hydroxy-5-methyl-3-(3-nitropyridin-4-yl)cyclohex-2-enylcarbamate (1.0 equiv.) in DCM (0.09 M) was added triethylamine (1.5 equiv.) and the reaction was cooled to 0° C. MsCl (1.2 equiv.) was added to the reaction and stirred for 3 h. Another 1.0 equiv. of MsCl was added to the reaction and stirred for another 2 h. Worked up the reaction by adding water, the organic phase was dried with brine, sodium sulfate, and concentrated. The crude product was purified via silica gel column chromatography eluting with ethyl acetate and hexanes (1:1) to afford 2-(tert-butoxycarbonylamino)-6-methyl-4-(3-nitropyridin-4-yl)cyclohex-3-enyl methanesulfonate as a white foam in 65% yield. LC/MS=428.2 (M+H), LC: 3.542 min.

Synthesis of (+/−)-tert-butyl 7-methyl-5-(3-nitropyridin-4-yl)-2-oxo-3a,6,7,7a-tetrahydrobenzo[d]oxazole-3(2H)-carboxylate

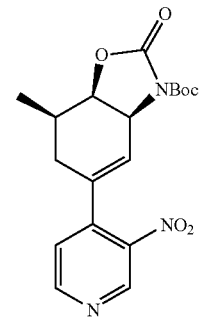

A solution of (+/−)-2-(tert-butoxycarbonylamino)-6-methyl-4-(3-nitropyridin-4-yl)cyclohex-3-enyl methanesulfonate (1.0 equiv.) in pyridine (0.2M) was heated in the microwave at 110° C. for 10 min. The orange reaction was then concentrated under vacuo, the crude was dissolved in ethyl acetate and water, the organic phase was dried with sodium sulfate and concentrated under vacuo. The crude material was dissolved in DCM (0.2M), triethylamine (1.8 equiv.) was added, followed by Boc$_2$O (1.2 equiv.). The reaction was stirred for 40 min, then concentrated to dryness. The crude material was purified via silica gel column chromatography eluting with hexane and ethyl acetate (1:1) to afford (+/−)-tert-butyl 7-methyl-5-(3-nitropyridin-4-yl)-2-oxo-3a,6,7,7a-tetrahydrobenzo[d]oxazole-3(2H)-carboxylate as a white foam in 66% yield. LC/MS=376.0 (M+H), LC: 3.424 min.

Synthesis of (+/−)-tert-butyl 5-(3-aminopyridin-4-yl)-7-methyl-2-oxohexahydrobenzo[d]oxazole-3(2H)-carboxylate

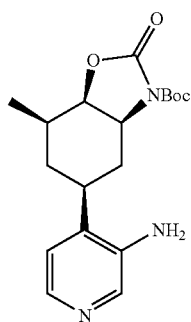

To a degassed solution of (+/−)-tert-butyl 7-methyl-5-(3-nitropyridin-4-yl)-2-oxo-3a,6,7,7a-tetrahydrobenzo[d]oxazole-3(2H)-carboxylate (1.0 equiv.) in MeOH and EtOAc (1:1, 0.1M) was added Pd/C (0.1 equiv.). The reaction was stirred under a hydrogen balloon overnight. Upon completion, the solution was filtered through a pad of Celite and the pad was washed with ethyl acetate. The filtrate was concentrated under vacuo to give (+/−)-tert-butyl 5-(3-aminopyridin-4-yl)-7-methyl-2-oxohexahydrobenzo[d]oxazole-3(2H)-carboxylate as the desired product as a yellow foam in 93% yield. LC/MS=348.1 (M+H), Rt=055 min.

Synthesis of tert-butyl(2R)-1-(benzyloxy)-3-hydroxy-4-methylhex-5-en-2-ylcarbamate

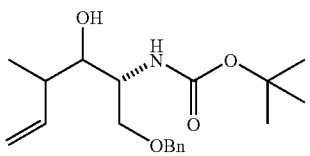

To a solution of N-Boc, O-benzyl-D-Serine aldehyde (1.0 equiv) in DCM (0.1 M) at −78° C. under an Ar atmosphere was added (Z)-2-(but-2-enyl)-4,4,5,5-tetramethyl-1,3,2-dioxaborolane (1.1 equiv) and the clear solution stirred for 16 hours as it warmed to rt. The solution was added to EtOAc and was washed with H$_2$O (3×), and NaCl$_{(sat.)}$, dried over MgSO$_4$ and purified by silica gel chromatography (15% EtOAc/hexanes) to yield tert-butyl(2R)-1-(benzyloxy)-3-hydroxy-4-methylhex-5-en-2-ylcarbamate (54%) as a 3:1 mixture of isomers as judged by $^1$H NMR. LCMS (m/z): 236.3 (MH$^+$-Boc); LC R$_t$=4.37 and 4.51 min.

Synthesis of (4R)-4-(benzyloxymethyl)-5-(but-3-en-2-yl)oxazolidin-2-one

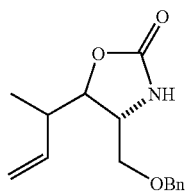

To a solution of (2R)-1-(benzyloxy)-3-hydroxy-4-methylhex-5-en-2-in THF (0.1 M) was added 60% sodium hydride in mineral oil (1.5 equiv.). After stirring for 3 days, the reaction was quenched by addition of NH$_4$Cl$_{(sat.)}$ and solution was diluted with EtOAc and washed with NH$_4$Cl$_{(sat.)}$ and NaCl$_{(sat.)}$, dried over MgSO$_4$ and purified by silica gel chromatography (50% EtOAc/hexanes) to yield (4R)-4-(benzyloxymethyl)-5-(but-3-en-2-yl)oxazolidin-2-one (89%) as a 3:1 mixture. LCMS (m/z): 262.2 (MH$^+$); LC R$_t$=3.47 min.

Synthesis of (4R)-4-(benzyloxymethyl)-5-(1-hydroxypropan-2-yl)oxazolidin-2-one

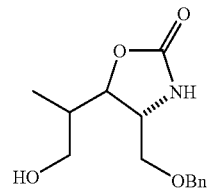

To a solution of (4R)-4-(benzyloxymethyl)-5-(but-3-en-2-yl)oxazolidin-2-one (1.0 equiv.) in 2:1 MeOH/H$_2$O (0.04 M) was added osmium tetroxide 4% in H$_2$O (0.07 equiv) and sodium periodate (3.0 equiv.). After stirring for 3 hours, the white precipitate was filtered and rinsed with EtOAc. The combined filtrate was concentrated in vacuo and the residue was dissolved in EtOAc, washed with NaCl$_{(sat.)}$, dried over MgSO$_4$, filtered and concentrated. The crude aldehyde was dissolved in EtOH (0.08 M) and upon cooling to 0° C., sodium borohydride (2.0 equiv.) was added. After stirring for 15 hours and coming to room temperature the reaction was quenched by addition of H$_2$O. After stirring for 20 minutes, the EtOH was removed in vacuo, EtOAc was added and the solution was washed with 1N HCl, NaHCO$_{3(sat.)}$ and NaCl$_{(sat.)}$, dried over MgSO$_4$, filtered and concentrated yielding after purification by silica gel chromatography (4R)-4-(benzyloxymethyl)-5-(1-hydroxypropan-2-yl)oxazolidin-2-one as a 3:1 mixture of isomers (60%). LCMS (m/z): 266.1 (MH$^+$); LC R$_t$=2.28 min.

Synthesis of (4R)-4-(hydroxymethyl)-5-(1-hydroxypropan-2-yl)oxazolidin-2-one

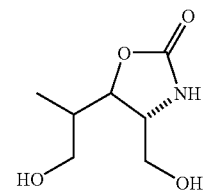

To a solution of (4R)-4-(benzyloxymethyl)-5-(1-hydroxypropan-2-yl)oxazolidin-2-one (1.0 equiv.) in methanol, at a concentration of 0.1 M, was added 10% palladium on carbon (0.1 eq.). The resultant heterogeneous solution was put under an atmosphere of hydrogen and was stirred for 15 hours. At this time the mixture was filtered through a pad of celite eluting with methanol. The volatiles were removed in vacuo yielding (4R)-4-(hydroxymethyl)-5-(1-hydroxypropan-2-yl)oxazolidin-2-one (99%). LCMS (m/z): 176.1 (MH$^+$).

Synthesis of 2-((4R)-2-oxo-4-(tosyloxymethyl)oxazolidin-5-yl)propyl 4-methylbenzenesulfonate

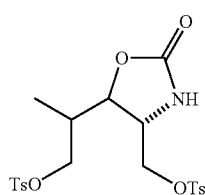

To a solution of (4R)-4-(hydroxymethyl)-5-(1-hydroxypropan-2-yl)oxazolidin-2-one (1.0 equiv.) in pyridine (0.15 M) at 0° C. was added p-toluenesulfonylchloride (2.1 equiv.). The solution was allowed to warm to rt as it stirred for 14 hours, at which time EtOAc was added and the solution was washed with H$_2$O (3×), CuSO$_{4(sat.)}$ (2×), H$_2$O, Na$_2$CO$_{3(sat.)}$ and NaCl$_{(sat.)}$, dried over MgSO$_4$, filtered, concentrated and purified by silica gel chromatography (75% EtOAc/hexanes eluant) yielding 2-((4R)-2-oxo-4-(tosyloxymethyl)oxazolidin-5-yl)propyl 4-methylbenzenesulfonate (68%). LCMS (m/z): 484.1 (MH$^+$); LC R$_t$=4.06 min.

Synthesis of (3aR,7R,7aS)-5-(4-methoxybenzyl)-7-methylhexahydrooxazolo[4,5-c]pyridin-2(3H)-one and (3aR,7S,7aR)-5-(4-methoxybenzyl)-7-methylhexahydrooxazolo[4,5-c]pyridin-2(3H)-one

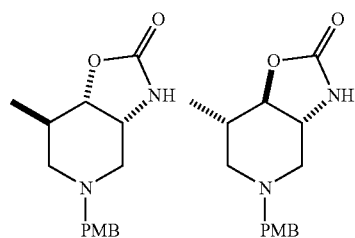

A solution of 2-((4R)-2-oxo-4-(tosyloxymethyl)oxazolidin-5-yl)propyl 4-methylbenzenesulfonate (1.0 equiv.), diisopropylethyl amine (3.0 equiv.) and para-methoxybenzylamine (1.5 equiv.) in NMP (0.05 M) was heated at 100° C. for 14 hours. The solution was purified directly by RP HPLC. The product fractions were desalted by addition to EtOAc and Na$_2$CO$_{3(s)}$, washed further with NaCl(sat.), dried over MgSO$_4$ and concentrated yielding two separate isomers of (3aR,7R,7aS)-5-(4-methoxybenzyl)-7-methylhexahydrooxazolo[4,5-c]pyridin-2(3H)-one and (3aR,7S,7aR)-5-(4-methoxybenzyl)-7-methylhexahydrooxazolo[4,5-c]pyridin-2(3H)-one (27% and 8%). LCMS (m/z): 277.2 (MH$^+$).

Synthesis of (3aR,7R,7aS)-7-methylhexahydrooxazolo[4,5-c]pyridin-2(3H)-one

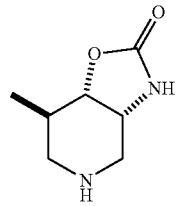

To a solution of (3aR,7R,7aS)-5-(4-methoxybenzyl)-7-methylhexahydrooxazolo[4,5-c]pyridin-2(3H)-one (1.0 equiv.) in methanol, at a concentration of 0.1 M, was added 20% palladium hydroxide on carbon (0.3 eq.). The resultant heterogeneous solution was put under an atmosphere of hydrogen and was stirred for 2 hours. At this time the mixture was filtered through a pad of celite eluting with methanol. The volatiles were removed in vacuo yielding (3aR,7R,7aS)-7-methylhexahydrooxazolo[4,5-c]pyridin-2(3H)-one (99%). LCMS (m/z): 157.1 (MH$^+$).

Synthesis of (3aR,7R,7aS)-tert-butyl 7-methyl-5-(3-nitropyridin-4-yl)-2-oxohexahydrooxazolo[4,5-c]pyridine-3(2H)-carboxylate

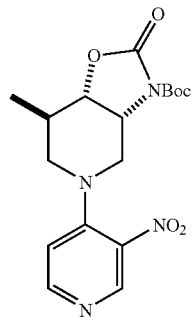

A solution of 4-chloro-3-nitropyridine (1.3 equiv.) and (3aR,7R,7aS)-7-methylhexahydrooxazolo[4,5-c]pyridin-2(3H)-one (1.5 equiv.) in CH$_2$Cl$_2$, at a concentration of 0.1 M, was stirred at rt for 48 hours at which piperidine (0.4 equiv) was added to consume excess 4-chloro-3-nitropyridine. After stirring for an additional 2 hours, di-tert-butyl dicarbonate (2.0 equiv.) and dimethylaminopyridine (0.1 equiv.) were added. After stirring for 4 hours, the solution was partitioned between EtOAc and NaHCO$_{3\ (sat.)}$, was washed further with NaHCO$_{3\ (sat.)}$ and NaCl$_{(sat.)}$, was dried over MgSO$_4$, was filtered and purified by silica gel chromatography yielding (3aR,7R,7aS)-tert-butyl 7-methyl-5-(3-nitropyridin-4-yl)-2-oxohexahydrooxazolo[4,5-c]pyridine-3(2H)carboxylate (62%). LCMS (m/z): 379.0 (MH$^+$).

Synthesis of (3aR,7R,7aS)-tert-butyl 5-(3-aminopyridin-4-yl)-7-methyl-2-oxohexahydrooxazolo[4,5-c]pyridine-3(2H)-carboxylate

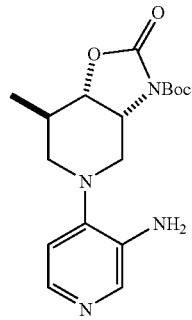

To a solution of (3aR,7R,7aS)-tert-butyl 7-methyl-5-(3-nitropyridin-4-yl)-2-oxohexahydrooxazolo[4,5-c]pyridine-3(2H)-carboxylate (1.0 equiv.) in methanol, at a concentration of 0.1 M, was added 10% palladium on carbon (0.1 eq.). The resultant heterogeneous solution was put under an atmosphere of hydrogen and was stirred for 14 hours. At this time the mixture was filtered through a pad of celite eluting with methanol. The volatiles were removed in vacuo yielding (3aR,7R,7aS)-tert-butyl 5-(3-aminopyridin-4-yl)-7-methyl-2-oxohexahydrooxazolo[4,5-c]pyridine-3(2H)-carboxylate. LCMS (m/z): 349.1 (MH$^+$); LC R$_t$=2.06 min.

Synthesis of (3aR,7S,7aR)-7-methylhexahydrooxazolo[4,5-c]pyridin-2(3H)-one

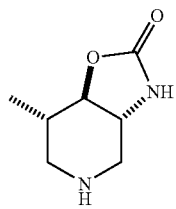

To a solution of (3aR,7S,7aR)-5-(4-methoxybenzyl)-7-methylhexahydrooxazolo[4,5-c]pyridin-2(3H)-one (1.0 equiv.) in methanol, at a concentration of 0.1 M, was added 20% palladium hydroxide on carbon (0.3 eq.). The resultant heterogeneous solution was put under an atmosphere of hydrogen and was stirred for 2 hours. At this time the mixture was filtered through a pad of celite eluting with methanol. The volatiles were removed in vacuo yielding (3aR,7S,7aR)-7-methylhexahydrooxazolo[4,5-c]pyridin-2(3H)-one (99%). LCMS (m/z): 157.1 (MH$^+$).

Synthesis of (3aR,7S,7aR)-tert-butyl 7-methyl-5-(3-nitropyridin-4-yl)-2-oxohexahydrooxazolo[4,5-c]pyridine-3(2H)-carboxylate

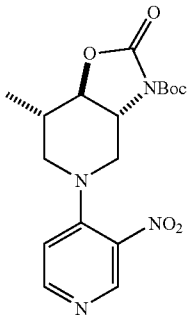

A solution of 4-chloro-3-nitropyridine (1.3 equiv.) and (3aR,7S,7aR)-7-methylhexahydrooxazolo[4,5-c]pyridin-2(3H)-one (1.5 equiv.) in CH$_2$Cl$_2$, at a concentration of 0.1 M, was stirred at rt for 48 hours at which piperidine (0.4 equiv) was added to consume excess 4-chloro-3-nitropyridine. After stirring for an additional 2 hours, di-tert-butyl dicarbonate (2.0 equiv.) and dimethylaminopyridine (0.1 equiv.) were added. After stirring for 4 hours, the solution was partitioned between EtOAc and NaHCO$_3$ $_{(sat.)}$, was washed further with NaHCO$_3$ $_{(sat.)}$, and NaCl$_{(sat.)}$, was dried over MgSO$_4$, was filtered and purified by silica gel chromatography (75% EtOAc/hexanes eluant) yielding (3aR,7S,7aR)-tert-butyl 7-methyl-5-(3-nitropyridin-4-yl)-2-oxohexahydrooxazolo[4,5-c]pyridine-3(2H)-carboxylate (35%). LCMS (m/z): 379.0 (MH$^+$). LC R$_t$=2.42 min.

Synthesis of (3aR,7R,7aS)-tert-butyl 5-(3-aminopyridin-4-yl)-7-methyl-2-oxohexahydrooxazolo[4,5-c]pyridine-3(2H)-carboxylate

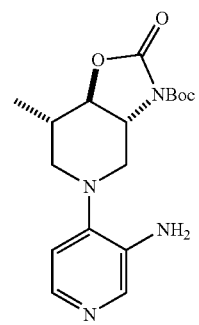

To a solution of (3aR,7S,7aR)-tert-butyl 7-methyl-5-(3-nitropyridin-4-yl)-2-oxohexahydrooxazolo[4,5-c]pyridine-3(2H)-carboxylate (1.0 equiv.) in methanol, at a concentration of 0.1 M, was added 10% palladium on carbon (0.1 eq.). The resultant heterogeneous solution was put under an atmosphere of hydrogen and was stirred for 14 hours. At this time the mixture was filtered through a pad of celite eluting with methanol. The volatiles were removed in vacuo yielding (3aR,7S,7aR)-tert-butyl 5-(3-aminopyridin-4-yl)-7-methyl-2-oxohexahydrooxazolo[4,5-c]pyridine-3(2H)-carboxylate. LCMS (m/z): 349.1 (MH$^+$); LC R$_t$=2.18 min.

METHOD 3

Synthesis of 2,6-difluorobenzothioamide

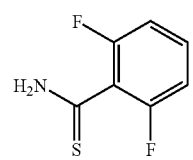

A solution of 2,6 difluorobenzamide (1 eq) and Lawesson's reagent (0.5 eq.) in toluene (0.2 M) was heated at 90° C. for 14 hours. Upon cooling the volatiles were removed in vacuo and purified by SiO$_2$ chromatography (25% EtOAc/hexanes) yielding 2,6-difluorobenzothioamide as a light yellow solid (99%). LCMS (m/z): 174.1 (MH$^+$); LC R$_t$=2.19 min.

Synthesis of cyclohexanecarbothioamide

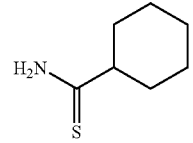

Following Method 3, cyclohexanecarboxamide and Lawesson's reagent were reacted, yielding cyclohexanecarbothioamide. LCMS (m/z): 144.1 (MH$^+$); LC R$_t$=5.10 min.

METHOD 4

Synthesis of ethyl 2-(2,6-difluorophenyl)thiazole-4-carboxylate

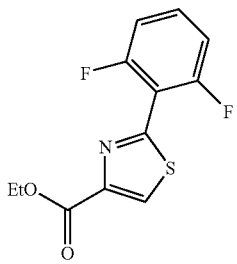

A solution of 2,6-difluorobenzothioamide (1.0 eq) and ethylbromopyruvate (1.0 eq.) in ethanol (1.0 M) was heated in the microwave at 130° C. for 30 minutes. Upon removal of volatiles in vacuo, ethyl acetate was added and the solution was washed with Na$_2$CO$_{3(sat.)}$, with NaCl$_{(sat.)}$, was dried over MgSO$_4$, filtered and concentrated yielding ethyl 2-(2,6-difluorophenyl)thiazole-4-carboxylate (84%). LCMS (m/z): 270.1 (MH$^+$); LC R$_t$=3.79 min.

Synthesis of ethyl 2-cyclohexylthiazole-4-carboxylate

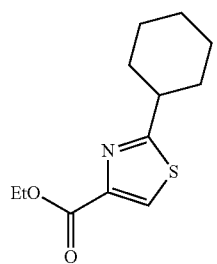

Following Method 4, cyclohexanecarbothioamide was used to yield ethyl 2-cyclohexylthiazole-4-carboxylate. LCMS (m/z): 240.1 (MH$^+$); LC R$_t$=3.90 min.

METHOD 5

Synthesis of 2-(2,6-difluorophenyl)thiazole-4-carboxylic acid

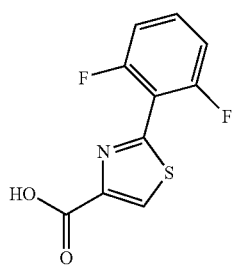

To a solution of ethyl 2-(2,6-difluorophenyl)thiazole-4-carboxylate (1.0 eq.) in 2:1 THF/MeOH (0.17 M) was added 1.0 M LiOH (2.0 eq.). After standing for 16 hours, 1.0 M HCl (2.0 eq.) was added and the THF/MeOH was removed in vacuo. The resulting solid was filtered, rinsed with H$_2$O and dried, yielding 2-(2,6-difluorophenyl)thiazole-4-carboxylic acid (88%) as a crusty solid. LCMS (m/z): 251.1 (MH$^+$); LC R$_t$=2.68 min.

Synthesis of 2-cyclohexylthiazole-4-carboxylic acid

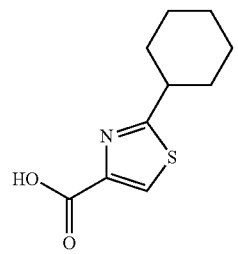

Following Method 5, ethyl 2-cyclohexylthiazole-4-carboxylate was hydrolyzed yielding 2-cyclohexylthiazole-4-carboxylic acid. LCMS (m/z): 212.1 (MH$^+$); LC R$_t$=2.90 min.

Synthesis of ethyl 2-amino-2-cyanoacetate

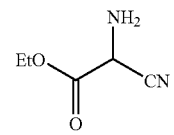

To a solution of ethyl 2-cyano-2-(hydroxyimino)acetate (1 eq) in 70 mL of water and 56 mL of aq. sat. sodium bicarbonate was added portionwise throughout 10 minutes Na$_2$S$_2$O$_4$ (2.8 eq) The reaction mixture was stirred at room temperature for 1 hour. The solution was saturated with sodium chloride, extracted with methylene chloride (300 mL×3) and then the combined organic layers were dried over anhydrous Na$_2$SO$_4$, filtered, and concentrated in vacuo to give the titled compound, which was used to next step without further (55%). LC/MS (m/z): 129.0 (MH$^+$), R$_t$: 0.25 min.

Synthesis of ethyl 2-cyano-2-(2,6-difluorobenzamido)acetate

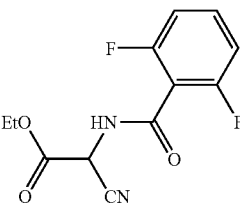

To a solution of ethyl 2-amino-2-cyanoacetate (1 eq) in 6 mL of dichloromethane was added pyridine (1.5 eq) and 2,6-difluorobenzoyl chloride (1 eq) at 0° C. The reaction mixture was stirred at room temperature for 3 hours. The mixture was diluted with ethyl acetate, washed with brine, then dried over anhydrous MgSO$_4$, filtered, and concentrated in vacuo. The crude residue was purified by flash chromatography (EtOAc:hexanes=1:1) to give the titled compound (84%). LC/MS (m/z): 269.1 (MH$^+$), R$_t$: 0.69 min.

Synthesis of 5-amino-2-(2,6-difluorophenyl)thiazole-4-carboxylic acid

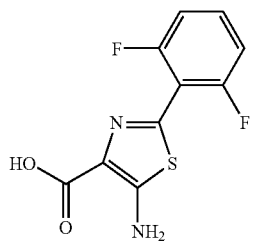

To a solution of the ethyl 2-cyano-2-(2,6-difluorobenzamido)acetate (1 eq) in 10 mL of toluene was added Lawesson reagent. The mixture was stirred at 95° C. for 2 days. Solvents were removed under reduced pressure. The crude residue was purified by flash chromatography (EtOAc:hexanes=1:1) to give the ethyl 5-amino-2-(2,6-difluorophenyl)thiazole-4-carboxylate, which was dissolved in 5 mL of methanol and 5 mL of THF. Then the mixture was added 1M sodium hydroxide (2 eq). The reaction mixture was stirred at room temperature overnight. The reaction was concentrated to remove most of solvents. The residue was extracted with ethyl acetate. The aqueous layer was acidified to pH=4-5 by 1N HCl. The resulting mixture was extracted by ethyl acetate. The organic layer was separated, washed with brine, then dried over anhydrous $MgSO_4$, filtered, and concentrated in vacuo. to give the pure titled compound (34%). LC/MS (m/z): 257.1 ($MH^+$), $R_t$: 0.61 min.

METHOD 6

Synthesis of (S)—N-(4-(3-aminopiperidin-1-yl)pyridin-3-yl)-2-(2,6-difluorophenyl)thiazole-4-carboxamide

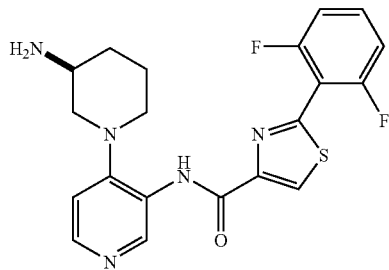

A homogeneous solution of 1 eq each of (S)-tert-butyl 1-(3-aminopyridin-4-yl)piperidin-3-ylcarbamate, 2-(2,6-difluorophenyl)thiazole-4-carboxylic acid, HOAT and EDC in NMP, at a concentration of 0.38 M, was left standing for 48 hours at which time the mixture was directly purified by HPLC. Upon lyophilization, the TFA salt of (S)-tert-butyl 1-(3-(2-(2,6-difluorophenyl)thiazole-4-carboxamido)pyridin-4-yl)piperidin-3-ylcarbamate was obtained. Alternatively, the HPLC fractions could be added to EtOAc and solid $Na_2CO_3$, separated and washed with $NaCl_{(sat.)}$. Upon drying over $MgSO_4$, filtering and removing the volatiles in vacuo, (S)-tert-butyl 1-(3-(2-(2,6-difluorophenyl)thiazole-4-carboxamido)pyridin-4-yl)piperidin-3-ylcarbamate was obtained.

The Boc group was removed by treating with 25% TFA/$CH_2Cl_2$ for 2 hours or with excess 4M HCl in dioxane for 12 hours. Upon removal of the volatiles in vacuo, the material was purified by RP HPLC yielding after lyophilization (S)—N-(4-(3-aminopiperidin-1-yl)pyridin-3-yl)-2-(2,6-difluorophenyl)thiazole-4-carboxamide as the TFA salt. Alternatively, the HPLC fractions could be added to EtOAc and solid $Na_2CO_3$, separated and washed with $NaCl_{(sat.)}$. Upon drying over $MgSO_4$, filtering and removing the volatiles in vacuo the free base was obtained. Upon dissolving in $MeCN/H_2O$, adding 1 eq. of 1 N HCl and lyophilizing, the HCl salt of (S)—N-(4-(3-aminopiperidin-1-yl)pyridin-3-yl)-2-(2,6-difluorophenyl)thiazole-4-carboxamide was obtained (43%). LCMS (m/z): 416.1 ($MH^+$); LC $R_t$=1.95 min.

If benzoyl protected hydroxyls were present they could be deprotected prior to Boc removal by treating with 0.2 M sodium hydroxide (3 eq) in MeOH at room temperature for 3 hours, upon which time the solution was diluted with ethyl acetate, washed with brine, dried over anhydrous $MgSO_4$, filtered, and concentrated in vacuo to yield the Boc protected alcohol.

If an N-Boc1,2 amino alcohol cyclic carbamate was present, prior to Boc deprotection the cyclic carbamate could be cleaved by treating with $Cs_2CO_2$ (0.5 eq) in methanol at a concentration of 0.1 M for three hours. After removal of volatiles in vacuo, the Boc amino group was deprotected as described above.

If TBDMS ethers were present they were deprotected prior to Boc removal by treating with 6N HCl, THF, methanol (1:2:1) at room temperature for 2 h. After removal of volatiles in vacuo, the Boc amino group was deprotected as described above.

If a diethoxyphosphorylamino group was present, the amine was deprotected by heating in a 1:1 solution of dioxane/2N $HCl_{(aq.)}$ at 70° C. overnight. Upon removal of the volatiles in vacuo, the material was purified by RP HPLC.

The following compounds were prepared using Method 6:

| Ex. No. | Structure | Compound Name | LC/MS (M + H on UPCL) | LC/MS (Rf min on UPLC) |
| --- | --- | --- | --- | --- |
| 1 | Chiral | (S)-N-(4-(3-aminopiperidin-1-yl)pyridin-3-yl)-2-(2,6-difluorophenyl)thiazole-4-carboxamide | 416.1 | 1.95 |

-continued

| Ex. No. | Structure | Compound Name | LC/MS (M + H on UPCL) | LC/MS (Rf min on UPLC) |
|---|---|---|---|---|
| 2 | Chiral | N-(4-((3R,4R)-3-amino-4-hydroxypiperidin-1-yl)pyridin-3-yl)-2-(2,6-difluorophenyl)thiazole-4-carboxamide | 432.1 | 1.84 |
| 3 | Chiral | N-(4-((3R,4R)-3-amino-4-fluoropiperidin-1-yl)pyridin-3-yl)-2-(2,6-difluorophenyl)thiazole-4-carboxamide | 434.1 | 2.23 |
| 4 | Chiral | N-(4-((3S,4S)-3-amino-4-fluoropiperidin-1-yl)pyridin-3-yl)-2-(2,6-difluorophenyl)thiazole-4-carboxamide | 434.1 | 2.22 |
| 5 | 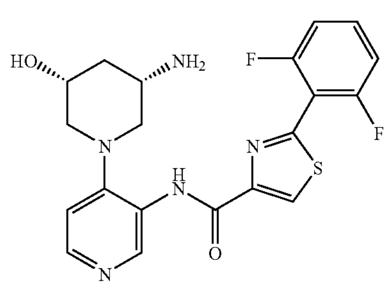 | N-(4-((3S,5R)-3-amino-5-hydroxypiperidin-1-yl)pyridin-3-yl)-2-(2,6-difluorophenyl)thiazole-4-carboxamide | 432 | 1.65 |

-continued

| Ex. No. | Structure | Compound Name | LC/MS (M + H on UPCL) | LC/MS (Rf min on UPLC) |
|---|---|---|---|---|
| 6 | 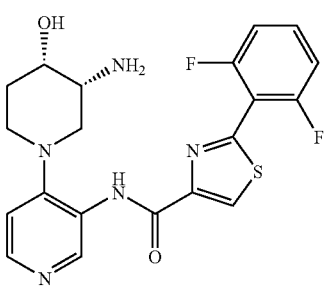 Chiral | N-(4-((3R,4S)-3-amino-4-hydroxypiperidin-1-yl) pyridin-3-yl)-2-(2,6-difluorophenyl)thiazole-4-carboxamide | 432.1 | 1.89 |
| 7 | 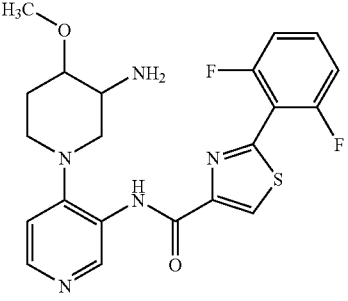 | N-(4-(3-amino-4-methoxypiperidin-1-yl) pyridin-3-yl)-2-(2,6-difluorophenyl)thiazole-4-carboxamide | 445.9 | 1.96 |
| 8 | 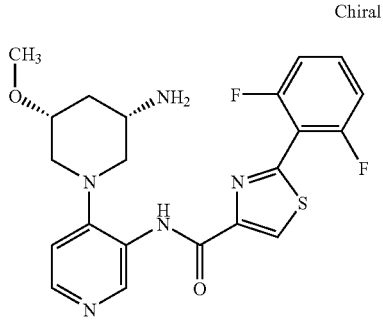 Chiral | N-(4-((3S,5R)-3-amino-5-methoxypiperidin-1-yl) pyridin-3-yl)-2-(2,6-difluorophenyl)thiazole-4-carboxamide | 446.1 | 1.83 |
| 9 | 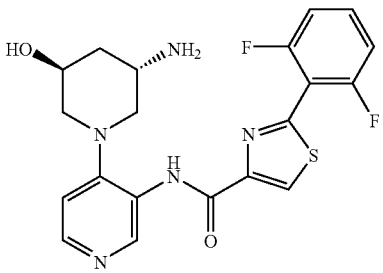 Chiral | N-(4-((3S,5S)-3-amino-5-hydroxypiperidin-1-yl) pyridin-3-yl)-2-(2,6-difluorophenyl)thiazole-4-carboxamide | 432.0 | 1.75 |

-continued

| Ex. No. | Structure | Compound Name | LC/MS (M + H on UPCL) | LC/MS (Rf min on UPLC) |
|---|---|---|---|---|
| 10 | Chiral | (3S,5S)-5-amino-1-(3-(2-(2,6-difluorophenyl)thiazole-4-carboxamido)pyridin-4-yl)piperidin-3-yl benzoate | 536.1 | 2.44 |
| 11 | Chiral | N-(4-((3S,5R)-3-amino-5-fluoropiperidin-1-yl)pyridin-3-yl)-2-(2,6-difluorophenyl)thiazole-4-carboxamide | 433.9 | 1.80 |
| 12 | Chiral | (S)-N-(4-(3-aminopiperidin-1-yl)pyridin-3-yl)-2-cyclohexylthiazole-4-carboxamide | 386.1 | 2.12 |
| 13 | 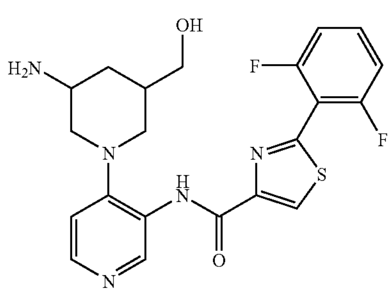 | N-(4-(3-amino-5-(hydroxymethyl)piperidin-1-yl)pyridin-3-yl)-2-(2,6-difluorophenyl)thiazole-4-carboxamide | 446.0 | 1.78 |
| 14 | 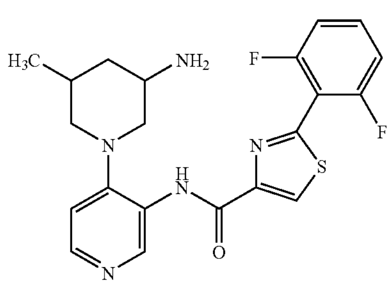 | N-(4-(3-amino-5-methylpiperidin-1-yl)pyridin-3-yl)-2-(2,6-difluorophenyl)thiazole-4-carboxamide | 430.0 | 2.14 |

-continued

| Ex. No. | Structure | Compound Name | LC/MS (M + H on UPCL) | LC/MS (Rf min on UPLC) |
|---|---|---|---|---|
| 15 | 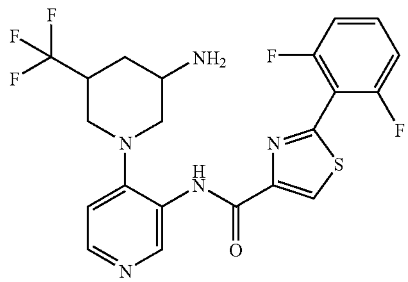 | N-(4-(3-amino-5-(trifluoromethyl)piperidin-1-yl)pyridin-3-yl)-2-(2,6-difluorophenyl)thiazole-4-carboxamide | 484.1 | 2.27 |
| 16 | 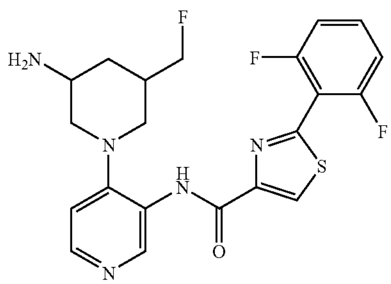 | N-(4-(3-amino-5-(fluoromethyl)piperidin-1-yl)pyridin-3-yl)-2-(2,6-difluorophenyl)thiazole-4-carboxamide | 448.0 | 2.05 |
| 17 | Chiral | N-(4-((3S,5S)-3-amino-5-fluoropiperidin-1-yl)pyridin-3-yl)-2-(2,6-difluorophenyl)thiazole-4-carboxamide | 434.0 | 0.49 |
| 18 | 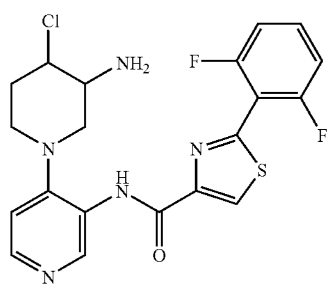 | N-(4-(3-amino-4-chloropiperidin-1-yl)pyridin-3-yl)-2-(2,6-difluorophenyl)thiazole-4-carboxamide | 449.8 | 0.55 |
| 19 | 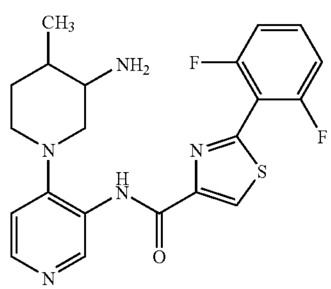 | N-(4-(3-amino-4-methylpiperidin-1-yl)pyridin-3-yl)-2-(2,6-difluorophenyl)thiazole-4-carboxamide | 430.1 | 0.57 |

-continued

| Ex. No. | Structure | Compound Name | LC/MS (M + H on UPCL) | LC/MS (Rf min on UPLC) |
|---|---|---|---|---|
| 20 | 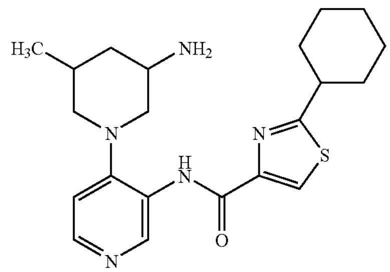 | N-(4-(3-amino-5-methylpiperidin-1-yl)pyridin-3-yl)-2-cyclohexylthiazole-4-carboxamide | 400.1 | 0.64 |
| 21 | 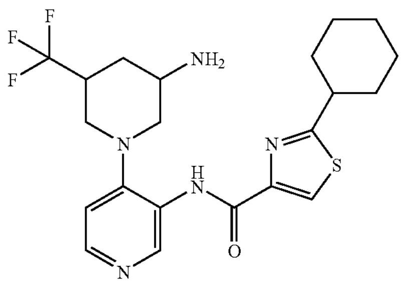 | N-(4-(3-amino-5-(trifluoromethyl)piperidin-1-yl)pyridin-3-yl)-2-cyclohexylthiazole-4-carboxamide | 454.1 | 0.72 |
| 22 | Chiral | N-(4-((3S,5S)-3-amino-5-methoxypiperidin-1-yl)pyridin-3-yl)-2-(2,6-difluorophenyl)thiazole-4-carboxamide | 446.1 | 0.54 |
| 23 | Chiral | N-(4-((3S,5R)-3-amino-5-ethoxypiperidin-1-yl)pyridin-3-yl)-2-(2,6-difluorophenyl)thiazole-4-carboxamide | 460.0 | 0.54 |
| 24 | Chiral | (S)-N-(4-(5-amino-3,3-difluoropiperidin-1-yl)pyridin-3-yl)-2-(2,6-difluorophenyl)thiazole-4-carboxamide | 452.0 | 0.56 |

-continued

| Ex. No. | Structure | Compound Name | LC/MS (M + H on UPCL) | LC/MS (Rf min on UPLC) |
|---|---|---|---|---|
| 25 | 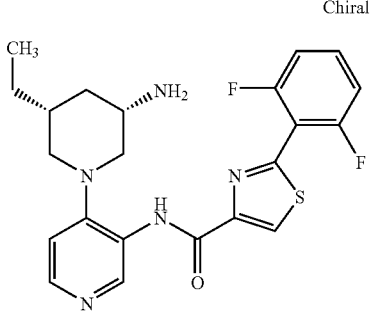 Chiral | N-(4-((3S,5R)-3-amino-5-ethylpiperidin-1-yl)pyridin-3-yl)-2-(2,6-difluorophenyl)thiazole-4-carboxamide | 444.1 | 0.57 |
| 26 | 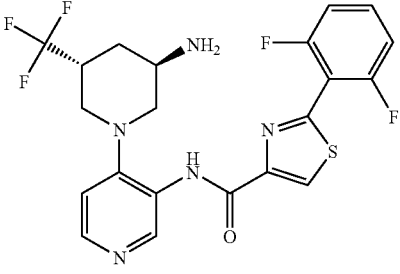 | N-(4-((3R,5R)-3-amino-5-(trifluoromethyl)piperidin-1-yl)pyridin-3-yl)-2-(2,6-difluorophenyl)thiazole-4-carboxamide | 484.1 | 0.57 |
| 27 | 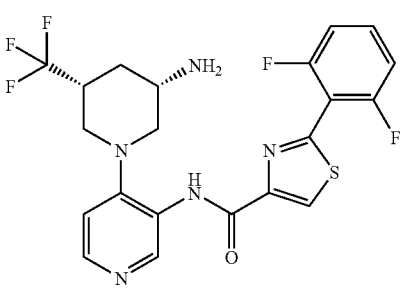 Chiral | N-(4-((3S,5R)-3-amino-5-(trifluoromethyl)piperidin-1-yl)pyridin-3-yl)-2-(2,6-difluorophenyl)thiazole-4-carboxamide | 484.0 | 0.68 |
| 28 | 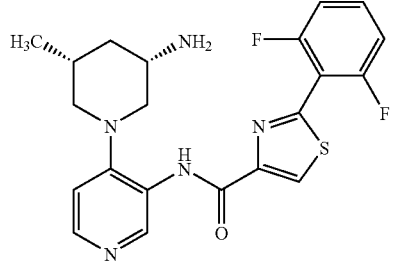 Chiral | N-(4-((3S,5R)-3-amino-5-methylpiperidin-1-yl)pyridin-3-yl)-2-(2,6-difluorophenyl)thiazole-4-carboxamide | 430.2 | 0.60 |

-continued

| Ex. No. | Structure | Compound Name | LC/MS (M + H on UPCL) | LC/MS (Rf min on UPLC) |
|---|---|---|---|---|
| 29 | Chiral | (S)-5-amino-N-(4-(3-aminopiperidin-1-yl)pyridin-3-yl)-2-(2,6-difluorophenyl)thiazole-4-carboxamide | 431.0 | 0.51 |
| 30 | 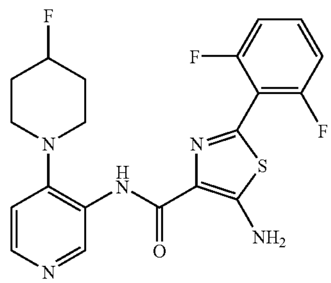 | 5-amino-2-(2,6-difluorophenyl)-N-(4-(4-fluoropiperidin-1-yl)pyridin-3-yl)thiazole-4-carboxamide | 434.0 | 0.75 |
| 31 | 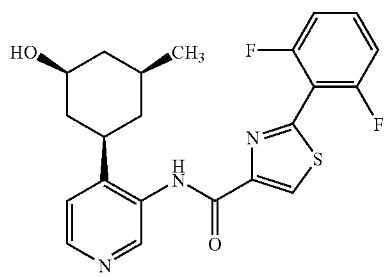 | 2-(2,6-difluorophenyl)-N-(4-((1R,3S,5S)-3-hydroxy-5-methylcyclohexyl)pyridin-3-yl)thiazole-4-carboxamide | 430.1 | 0.7 |
| 32 | 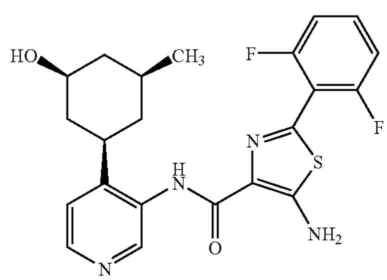 | 5-amino-2-(2,6-difluorophenyl)-N-(4-((1R,3S,5S)-3-hydroxy-5-methylcyclohexyl)pyridin-3-yl)thiazole-4-carboxamide | 445.1 | 0.7 |
| 33 | Chiral | 5-amino-N-(4-((1R,3S)-3-aminocyclohexyl)pyridin-3-yl)-2-(2,6-difluorophenyl)thiazole-4-carboxamide | 430.0 | 0.54 |

-continued

| Ex. No. | Structure | Compound Name | LC/MS (M + H on UPCL) | LC/MS (Rf min on UPLC) |
|---|---|---|---|---|
| 34 | 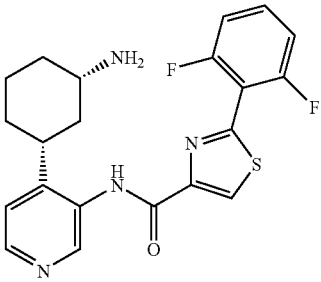 Chiral | N-(4-((1R,3S)-3-aminocyclohexyl)pyridin-3-yl)-2-(2,6-difluorophenyl)thiazole-4-carboxamide | 415.0 | 0.54 |
| 35 | 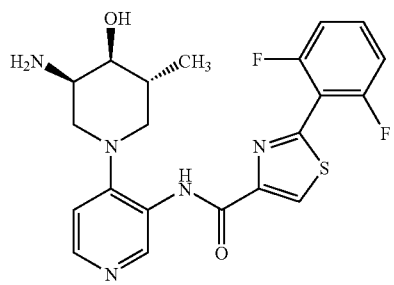 Chiral | N-(4-((3R,4S,5R)-3-amino-4-hydroxy-5-methylpiperidin-1-yl)pyridin-3-yl)-2-(2,6-difluorophenyl)thiazole-4-carboxamide | 446.2 | 0.51 |
| 36 | 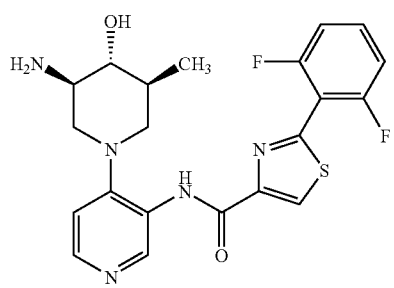 Chiral | N-(4-((3R,4R,5S)-3-amino-4-hydroxy-5-methylpiperidin-1-yl)pyridin-3-yl)-2-(2,6-difluorophenyl)thiazole-4-carboxamide | 446.0 | 0.55 |
| 37 | 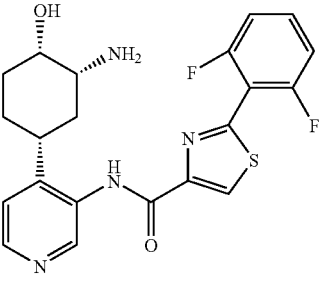 | N-(4-((1R,3R,4S)-3-amino-4-hydroxycyclohexyl)pyridin-3-yl)-2-(2,6-difluorophenyl)thiazole-4-carboxamide | 431.0 | 0.50 |
| 38 | 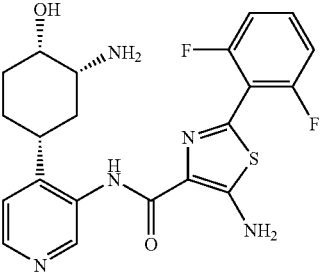 | 5-amino-N-(4-(3-amino-4-hydroxycyclohexyl)pyridin-3-yl)-2-(2,6-difluorophenyl)thiazole-4-carboxamide | 446.1 | 0.51 |

-continued

| Ex. No. | Structure | Compound Name | LC/MS (M + H on UPCL) | LC/MS (Rf min on UPLC) |
|---|---|---|---|---|
| 39 | 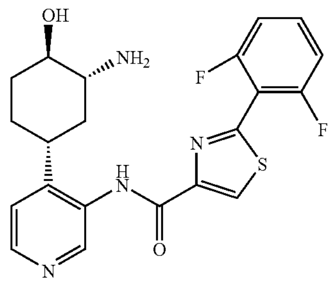 | N-(4-((1R,3R,4R)-3-amino-4-hydroxycyclohexyl)pyridin-3-yl)-2-(2,6-difluorophenyl)thiazole-4-carboxamide | 431.0 | 0.54 |
| 40 | 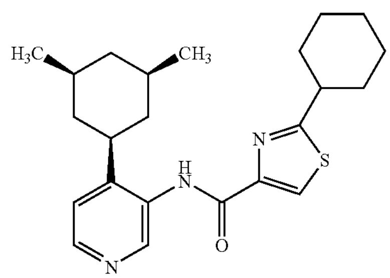 | N-(4-((1R,3S,5S)-3-amino-5-methylcyclohexyl)pyridin-3-yl)-2-cyclohexylthiazole-4-carboxamide | 399.3 | 0.63 |
| 41 | 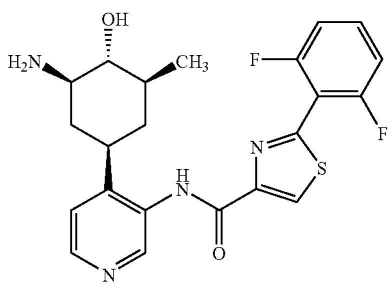 | N-(4-((1R,3R,4R,5S)-3-amino-4-hydroxy-5-methylcyclohexyl)pyridin-3-yl)-2-(2,6-difluorophenyl)thiazole-4-carboxamide (and enantiomer) | 445.1 | 0.52 |
| 42 | 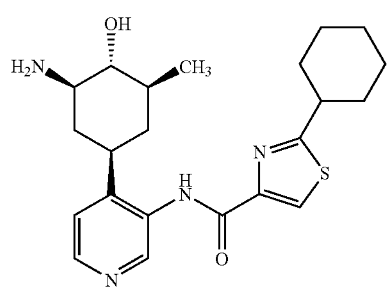 | N-(4-((1R,3R,4R,5S)-3-amino-4-hydroxy-5-methylcyclohexyl)pyridin-3-yl)-2-cyclohexylthiazole-4-carboxamide | 415.1 | 0.60 |
| 43 | 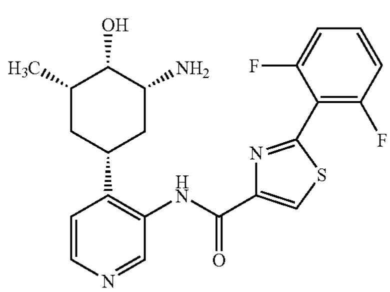 | N-(4-((1R,3R,4S,5S)-3-amino-4-hydroxy-5-methylcyclohexyl)pyridin-3-yl)-2-(2,6-difluorophenyl)thiazole-4-carboxamide (and enantiomer) | 445.2 | 0.54 |

-continued

| Ex. No. | Structure | Compound Name | LC/MS (M + H on UPCL) | LC/MS (Rf min on UPLC) |
|---|---|---|---|---|
| 44 | Chiral | N-(4-((1S,3R,5R)-3-amino-5-methylcyclohexyl)pyridin-3-yl)-2-(2,6-difluorophenyl)thiazole-4-carboxamide | 429.2 | 0.68 |
| 45 | Chiral | N-(4-((1R,3S,5S)-3-amino-5-methylcyclohexyl)pyridin-3-yl)-2-(2,6-difluorophenyl)thiazole-4-carboxamide | 429.2 | 0.68 |
| 46 | Chiral | N-(4-((1R,5R)-5-amino-3,3-dimethylcyclohexyl)pyridin-3-yl)-2-(2,6-difluorophenyl)thiazole-4-carboxamide | 443.2 | 0.60 |
| 47 | Chiral | N-(4-((1R,5R)-5-amino-3,3-dimethylcyclohexyl)pyridin-3-yl)-2-(2,6-difluorophenyl)thiazole-4-carboxamide | 443.2 | 0.60 |

Synthesis of (S)-tert-butyl 1-(3-(2-bromothiazole-4-carboxamido)pyridin-4-yl)piperidin-3-ylcarbamate

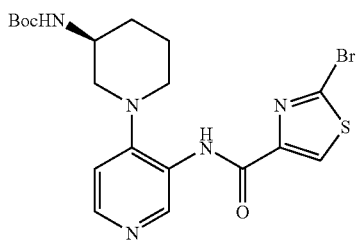

A solution containing 1 eq each of (S)-tert-butyl 1-(3-aminopyridin-4-yl)piperidin-3-ylcarbamate, 2-bromothiazole-4-carboxylic acid, HOAT and EDC in DMF, at a concentration of 0.5 M, was stirred for 60 hours. The solution was diluted with EtOAc and was washed with $H_2O$ (4×), NaCl $_{(sat.)}$, was dried over $MgSO_4$, was filtered and the volatiles were removed in vacuo yielding (S)-tert-butyl 1-(3-(2-bromothiazole-4-carboxamido)pyridin-4-yl)piperidin-3-ylcarbamate, LCMS (m/z): 416.1 (MH$^+$); LC $R_t$=1.95 min.

METHOD 7

Synthesis of (S)—N-(4-(3-aminopiperidin-1-yl)pyridin-3-yl)-2-(2-fluorophenyl)thiazole-4-carboxamide

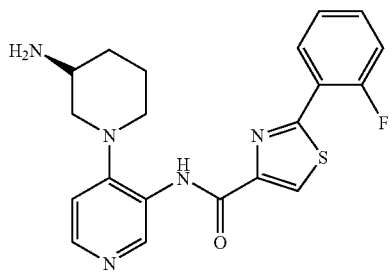

A solution of (S)-tert-butyl 1-(3-(2-bromothiazole-4-carboxamido)pyridin-4-yl)piperidin-3-ylcarbamate (1.0 eq), 2-fluorophenyl boronic acid (3.0 eq.), Pd(dppf)Cl$_2$—CH$_2$Cl$_2$ (0.15 eq.) in 3:1 DME/2M Na$_2$CO$_3$ (concentration=0.1 M) was heated at 120° C. with microwave irradiation for 1200 seconds. Upon cooling the organic layer was separated, concentrated and the N-Boc Suzuki product was directly purified by reverse phase HPLC. The product fraction was lyophilized and the resulting solid was treated with 25% TFA/DCM (at a resulting concentration of 0.05 M). After sitting for 2 hours, the volatiles were removed in vacuo and the residue was purified by reverse phase HPLC. After lyophilization, (S)—N-(4-(3-aminopiperidin-1-yl)pyridin-3-yl)-2-(2-fluorophenyl)thiazole-4-carboxamide was obtained (35%) as the TFA salt. LCMS (m/z): 398.1 (MH$^+$); LC Rt=2.06 min.

The following compounds were prepared using Method 7:

| Ex. No. | Structure | Compound Name | LC/MS (M + H on UPCL) | LC/MS (Rf min on UPLC) |
|---|---|---|---|---|
| 48 | Chiral | (S)-N-(4-(3-aminopiperidin-1-yl)pyridin-3-yl)-2-phenylthiazole-4-carboxamide | 380.1 | 1.94 |
| 49 | Chiral | (S)-N-(4-(3-aminopiperidin-1-yl)pyridin-3-yl)-2-(2-fluorophenyl)thiazole-4-carboxamide | 398.1 | 2.06 |

| Ex. No. | Structure | Compound Name | LC/MS (M + H on UPCL) | LC/MS (Rf min on UPLC) |
|---|---|---|---|---|
| 50 | 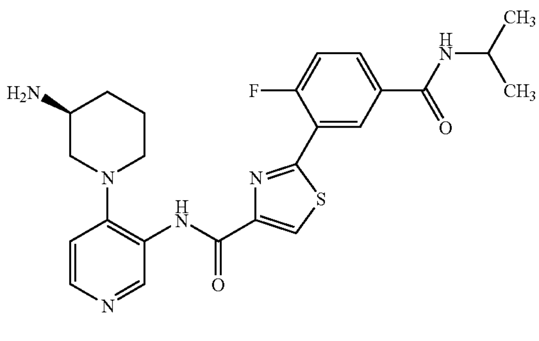 | (S)-N-(4-(3-aminopiperidin-1-yl)pyridin-3-yl)-2-(2-fluoro-5-(isopropylcarbamoyl)phenyl)thiazole-4-carboxamide | 483.2 | 2.04 |
| 51 | 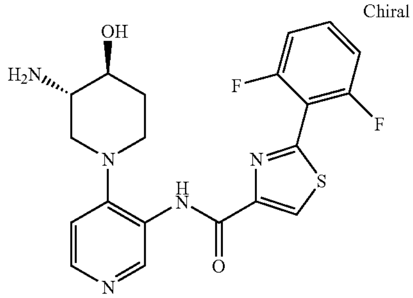 | N-(4-((3S,4S)-3-amino-4-hydroxy-piperidin-1-yl)pyridin-3-yl)-2-(2,6-difluorophenyl)thiazole-4-carboxamide | 432.1 | 1.85 |

Synthesis of tert-butyl(3R,4R)-1-(3-(2-bromothiaz-ole-4-carboxamido)pyridin-4-yl)-4-(tert-butyldimethylsilyloxy)piperidin-3-ylcarbamate A solution containing 1 eq each of tert-butyl(3R,4R)-1-(3-aminopyridin-4-yl)-4-(tert-butyldimethylsilyloxy)piperidin-3-ylcarbamate, 2-bromothiazole-4-carboxylic acid, HOAT and EDC in DMF, at a concentration of 0.5 M, was stirred for 60 hours. The solution was diluted with EtOAc and was washed with H₂O (4×), NaCl$_{(sat.)}$, was dried over MgSO₄, was filtered and the volatiles were removed in vacuo yielding tert-butyl(3R,4R)-1-(3-(2-bromothiazole-4-carboxamido)pyridin-4-yl)-4-(tert-butyldimethylsilyloxy)piperidin-3-ylcarbamate, LCMS (m/z): 612.2/614.2 (MH⁺); LC R$_f$=4.26 min.

Synthesis of tert-butyl(1S,3R,5S)-3-(3-(2-bromothiazole-4-carboxamido)pyridin-4-yl)-5-methylcyclohexylcarbamate

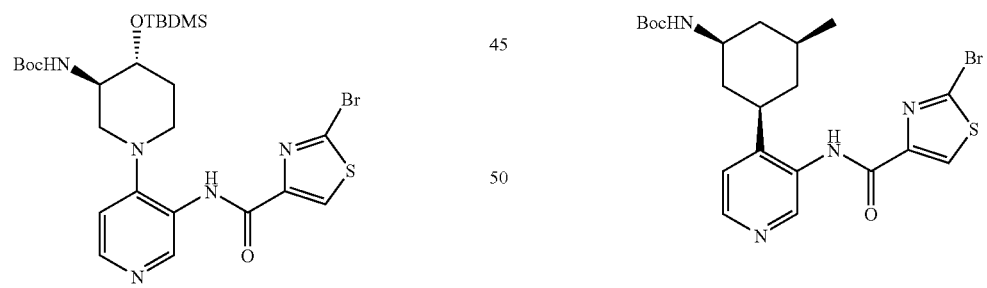

A solution containing 1 eq each of tert-butyl(1S,3R,5S)-3-(3-aminopyridin-4-yl)-5-methylcyclohexylcarbamate, 2-bromothiazole-4-carboxylic acid, HOAT and EDC in DMF, at a concentration of 0.3 M, was stirred for 17 hours. The solution was diluted with EtOAc and was washed with H₂O (4×), NaCl$_{(sat.)}$, was dried over MgSO₄, was filtered and the volatiles were removed in vacuo yielding tert-butyl (1S,3R,5S)-3-(3-(2-bromothiazole-4-carboxamido)pyridin-4-yl)-5-methylcyclohexylcarbamate, LCMS (m/z): 495.1/497.1 (MH⁺); LC R$_f$=3.17 min.

METHOD 8

Synthesis of N-(4-((1R,3S,5S)-3-amino-5-methylcyclohexyl)pyridin-3-yl)-2-(2,6-difluoro-3-methoxyphenyl)thiazole-4-carboxamide

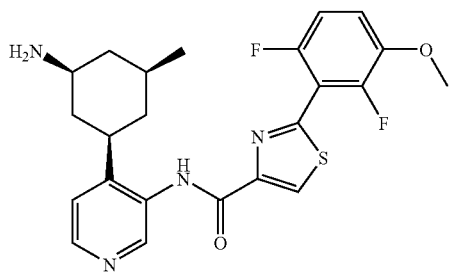

A solution of tert-butyl(1S,3R,5S)-3-(3-(2-bromothiazole-4-carboxamido)pyridin-4-yl)-5-methylcyclohexylcarbamate (1.0 equiv.), 2,6-difluoro-3-methoxyphenylboronic acid (4.0 equiv.), DIEA (4.0 equiv.) and Pd(PPh$_3$)$_4$ (0.2 equiv) in 1:1 toluene/ethanol at a concentration of 0.03 M was heated in a microwave at 120° C. for 20 minutes. The solution was resubmitted to heating in the microwave at 130° C. for 2×30 min. The solvents were removed in vacuo and the residue was purified by HPLC. The product fractions were lyophilized directly to yield the protected amide product as the TFA salt. The Boc group was deprotected by treating with 25% TFA/CH$_2$Cl$_2$ for two hours. Upon removal of volatiles in vacuo, the product was purified by HPLC to yield N-(4-((1R,3S,5S)-3-amino-5-methylcyclohexyl)pyridin-3-yl)-2-(2,6-difluoro-3-methoxyphenyl)thiazole4-carboxamide. LCMS (m/z): 459.2 (MH$^+$); LC R$_f$=2.32 min.

When applying the above method for Suzuki it is at times necessary to resubmit to heating in the microwave and additionally add more of the boronic acid (4.0 equiv.), DIEA (4.0 equiv.) and Pd(PPh$_3$)$_4$ (0.2 equiv) with each resubmission.

Alternatively, Suzuki reactions with 2,6 difluorosubstituted boronic acids and 2-bromo-4-carboxamido thiazoles can be carried out by heating the bromide (1.0 equiv), boronic acid (5 equiv.), KF (5.5 equiv.), tri-tert-butylphosphine (0.4 equiv) and Pd$_2$(dba)$_3$ (0.2 equiv.) in 10:1 THF/H$_2$O at a concentration of 0.03 M in the microwave at 100° C. for 30 minutes. With this method, is at times necessary to resubmit to heating in the microwave at 100° C. and additionally add more of the boronic acid (5.0 equiv.), KF (5.5 equiv.), tri-tert-butylphosphine (0.4 equiv) and Pd$_2$(dba)$_3$ (0.2 equiv.) with each resubmission.

The following compounds were prepared using Method 8:

| Ex. No. | Structure | Compound Name | LC/MS (M + H on UPCL) | LC/MS (Rf min on UPLC) |
| --- | --- | --- | --- | --- |
| 52 | Chiral | 2-(2,6-Difluoro-3-methoxy-phenyl)-thiazole-4-carboxylic acid [4-(3-amino-5-methyl-cyclohexyl)-pyridin-3-yl]-amide | 459.2 | 0.58 |
| 53 | Chiral | 2-[2-Fluoro-1-(1-fluoro-vinyl)-3-isopropoxy-propenyl]-thiazole-4-carboxy acid [4-(3-amino-5-methyl-cyclohexyl)-pyridin-3-yl]-amide | 487.3 | 0.67 |

-continued

| Ex. No. | Structure | Compound Name | LC/MS (M + H on UPCL) | LC/MS (Rf min on UPLC) |
|---|---|---|---|---|
| 54 | Chiral | 2-(3-Ethoxy-2,6-difluoro-phenyl)-thiazole-4-carboxylic acid [4-(3-amino-5-methyl-cyclohexyl)-pyridin-3-yl]-amide | 473.3 | 0.63 |
| 55 | Chiral | 2-(2,3,6-Trifluoro-phenyl)-thiazole-4-carboxylic acid [4-(3-amino-5-methyl-cyclohexyl)-pyridin-3-yl]-amide | 447.2 | 0.59 |
| 56 | Chiral | 2-(3-Chloro-2,6-difluoro-phenyl)-thiazole-4-carboxylic acid [4-(3-amino-5-methyl-cyclohexyl)-pyridin-3-yl]-amide | 463.1 | 0.62 |
| 57 | Chiral | 2-(2,6-Difluoro-4-hydroxy-phenyl)-thiazole-4-carboxylic acid [4-(3-amino-5-methyl-cyclohexyl)-pyridin-3-yl]-amide | 445.2 | 0.54 |

Example 58

Synthesis of N-(4-((+/−)-3-amino-4-fluoro-5-methyl-cyclohexyl)pyridin-3-yl)-2-(2,6-difluorophenyl)thiazole-4-carboxamide

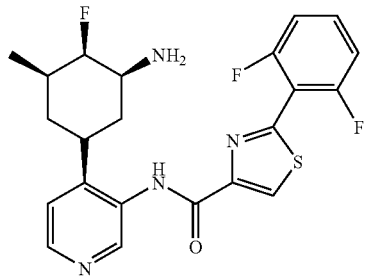

To a solution of (+/−)-2-(tert-butoxycarbonylamino)-4-(3-(2-(2,6-difluorophenyl)thiazole-4-carboxamido)pyridin-4-yl)-6-methylcyclohexyl acetate in MeOH (0.03 M) was added potassium carbonate (3.0 equiv.) and the reaction was stirred at room temperature for 3 h. Upon completion, the reaction was partitioned between water and ethyl acetate. The aqueous phase was further extracted 3 more times with ethyl acetate. The organics were combined, dried with brine and sodium sulfate, filtered, and concentrated. Isolated tert-butyl (+/−)-5-(3-(2-(2,6-difluorophenyl)thiazole-4-carboxamido)pyridin-4-yl)-2-hydroxy-3-methylcyclohexylcarbamate was obtained as an off-white solid in 87% yield. LC/MS=545.2 (M+H), Rt=0.75 min. To a solution of tert-butyl(+/−)-5-(3-(2-(2,6-difluorophenyl)thiazole-4-carboxamido)pyridin-4-yl)-2-hydroxy-3-methylcyclohexylcarbamate (1.0 equiv.) in DCM (0.07M) at 0° C. was added DAST (1.0 equiv.) under a nitrogen atmosphere. The reaction was stirred for 1 h, upon which time, 2 more equivalents of DAST were added. After 30 min, the consumption of the starting material was complete. The reaction was quenched by the addition of water, the organic phase was dried with sodium sulfate, and concentrated. The crude material was purified via silica gel column chromatography eluting with ethyl acetate and hexanes (1:1) to afford tert-butyl(+/−)-5-(3-(2-(2,6-difluorophenyl)thiazole-4-carboxamido)pyridin-4-yl)-2-fluoro-3-methylcyclohexylcarbamate as a clear oil in 60% yield. LC/MS=547.3 (M+H), Rt=0.92 min. The Boc group was removed by treating with 25% TFA in dichloromethane for 2 hours. Upon concentration under vacuo, the crude was purified via semi-prep HPLC. The pure fractions were lyophilized to yield N-(4-((+/−)-3-amino-4-fluoro-5-methylcyclohexyl)pyridin-3-yl)-2-(2,6-difluorophenyl)thiazole-4-carboxamide as the desired product as the TFA salt in 74% yield. LC/MS=447.0 (M+H), Rt=0.56 min.

The following compounds are prepared using the techniques and procedures described herein.

| Example | Structure | | Name |
|---|---|---|---|
| 59 | 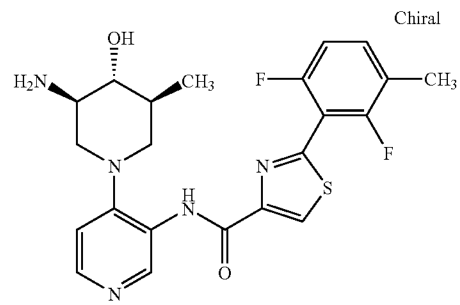 | Chiral | 2-(2,6-Difluoro-3-methyl-phenyl)-thiazole-4-carboxylic acid (3-amino-4-hydroxy-5-methyl-3,4,5,6-tetrahydro-2H-[1,4']bipyridinyl-3'-yl)-amide |
| 60 | 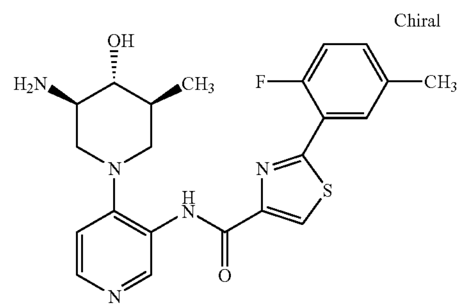 | Chiral | 2-(2-Fluoro-5-methyl-phenyl)-thiazole-4-carboxylic acid (3-amino-4-hydroxy-5-methyl-3,4,5,6-tetrahydro-2H-[1,4']bipyridinyl-3'-yl)-amide |
| 61 | 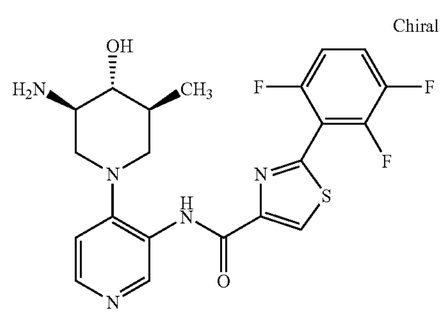 | Chiral | 2-(2,3,6-Trifluoro-phenyl)-thiazole-4-carboxylic acid (3-amino-4-hydroxy-5-methyl-3,4,5,6-tetrahydro-2H-[1,4']bipyridinyl-3'-yl)-amide |

| Example | Structure | Name |
|---|---|---|
| 62 | Chiral | 2-(2-Fluoro-phenyl)-thiazole-4-carboxylic acid (3-amino-4-hydroxy-5-methyl-3,4,5,6-tetrahydro-2H-[1,4']bipyridinyl-3'-yl)-amide |
| 63 | Chiral | 2-(2-Chloro-6-fluoro-phenyl)-thiazole-4-carboxylic acid (3-amino-4-hydroxy-5-methyl-3,4,5,6-tetrahydro-2H-[1,4']bipyridinyl-3'-yl)-amide |
| 64 | Chiral | 2-(2,6-Difluoro-3-methoxy-phenyl)-thiazole-4-carboxylic acid (3-amino-4-hydroxy-5-methyl-3,4,5,6-tetrahydro-2H-[1,4']bipyridinyl-3'-yl)-amide |
| 65 | Chiral | 2-Phenyl-thiazole-4-carboxylic acid (3-amino-4-hydroxy-5-methyl-3,4,5,6-tetrahydro-2H-[1,4]bipyridinyl-3'-yl)-amide |
| 66 | Chiral | 2-(2-Chloro-phenyl)-thiazole-4-carboxylic acid (3-amino-4-hydroxy-5-methyl-3,4,5,6-tetrahydro-2H-[1,4']bipyridinyl-3'-yl)-amide |

| Example | Structure | Name |
| --- | --- | --- |
| 67 | Chiral | 2-(2,6-Difluoro-3-hydroxy-phenyl)-thiazole-4-carboxylic acid [4-(3-amino-5-methyl-cyclohexyl)-pyridin-3-yl]-amide |
| 68 | Chiral | 2-(2-Fluoro-5-hydroxy-phenyl)-thiazole-4-carboxylic acid [4-(3-amino-5-methyl-cyclohexyl)-pyridin-3-yl]-amide |
| 69 | Chiral | 2-(2-Fluoro-4-hydroxy-phenyl)-thiazole-4-carboxylic acid [4-(3-amino-5-methyl-cyclohexyl)-pyridin-3-yl]-amide |
| 70 | Chiral | 2-(2,6-Difluoro-4-hydroxy-phenyl)-thiazole-4-carboxylic acid [4-(5-amino-3,3-dimethyl-cyclohexyl)-pyridin-3-yl]-amide |

-continued

| Example | Structure | Name |
|---|---|---|
| 71 | Chiral | 2-(2,6-Difluoro-3-hydroxy-phenyl)-thiazole-4-carboxylic acid [4-(5-amino-3,3-dimethyl-cyclohexyl)-pyridin-3-yl]-amide |
| 72 | Chiral | 2-(2-Fluoro-5-hydroxy-phenyl)-thiazole-4-carboxylic acid [4-(5-amino-3,3-dimethyl-cyclohexyl)-pyridin-3-yl]-amide |
| 73 | Chiral | 2-(2-Fluoro-4-hydroxy-phenyl)-thiazole-4-carboxylic acid [4-(5-amino-3,3-dimethyl-cyclohexyl)-pyridin-3-yl]-amide |
| 74 | Chiral | 2-(3-Chloro-2,6-difluoro-phenyl)-thiazole-4-carboxylic acid [4-(5-amino-3,3-dimethyl-cyclohexyl)-pyridin-3-yl]-amide |

-continued

| Example | Structure | Name |
| --- | --- | --- |
| 75 | Chiral | 2-(5-Chloro-2-fluoro-phenyl)-thiazole-4-carboxylic acid [4-(5-amino-3,3-dimethyl-cyclohexyl)-pyridin-3-yl]-amide |
| 76 | Chiral | 2-(2-Fluoro-5-methyl-phenyl)-thiazole-4-carboxylic acid [4-(5-amino-3,3-dimethyl-cyclohexyl)-pyridin-3-yl]-amide |
| 77 | Chiral | 2-(2,6-Difluoro-3-methyl-phenyl)-thiazole-4-carboxylic acid [4-(5-amino-3,3-dimethyl-cyclohexyl)-pyridin-3-yl]-amide |
| 78 | Chiral | 2-(2-Fluoro-5-methyl-phenyl)-thiazole-4-carboxylic acid [4-(3-amino-3,3-dimethyl-cyclohexyl)-pyridin-3-yl]-amide |

| Example | Structure | Name |
|---|---|---|
| 79 | Chiral | 2-(2,6-Difluoro-3-methyl-phenyl)-thiazole-4-carboxylic acid [4-(3-amino-5-methyl-cyclohexyl)-pyridin-3-yl]-amide |
| 80 | Chiral | 2-(2,6-Difluoro-4-hydroxy-phenyl)-thiazole-4-carboxylic acid (5-amino-3-methyl-3,4,5,6-tetrahydro-2H-[1,4']bipyridinyl-3'-yl)-amide |
| 81 | Chiral | 2-(2,6-Difluoro-3-hydroxy-phenyl)-thiazole-4-carboxylic acid (5-amino-3-methyl-3,4,5,6-tetrahydro-2H-[1,4']bipyridinyl-3'-yl)-amide |
| 82 | Chiral | 2-(2-Fluoro-5-hydroxy-phenyl)-thiazole-4-carboxylic acid (5-amino-3-methyl-3,4,5,6-tetrahydro-2H-[1,4']bipyridinyl-3'-yl)-amide |

-continued

| Example | Structure | Name |
|---|---|---|
| 83 | Chiral | 2-(2-Fluoro-4-hydroxy-phenyl)-thiazole-4-carboxylic acid (5-amino-3-methyl-3,4,5,6-tetrahydro-2H-[1,4']bipyridinyl-3'-yl)-amide |
| 84 | Chiral | 2-(2,6-Difluoro-4-hydroxy-phenyl)-thiazole-4-carboxylic acid (5-amino-3-ethyl-3,4,5,6-tetrahydro-2H-[1,4']bipyridinyl-3'-yl)-amide |
| 85 | Chiral | 2-(2,6-Difluoro-3-hydroxy-phenyl)-thiazole-4-carboxylic acid (5-amino-3-ethyl-3,4,5,6-tetrahydro-2H-[1,4']bipyridinyl-3'-yl)-amide |
| 86 | Chiral | 2-(2-Fluoro-5-hydroxy-phenyl)-thiazole-4-carboxylic acid (5-amino-3-ethyl-3,4,5,6-tetrahydro-2H-[1,4']bipyridinyl-3'-yl)-amide |

| Example | Structure | Name |
|---|---|---|
| 87 | Chiral | 2-(2-Fluoro-4-hydroxy-phenyl)-thiazole-4-carboxylic acid (5-amino-3-ethyl-3,4,5,6-tetrahydro-2H-[1,4']bipyridinyl-3'-yl)-amide |
| 88 | Chiral | 2-(2,6-Difluoro-4-hydroxy-phenyl)-thiazole-4-carboxylic acid (5-amino-3-trifluoromethyl-3,4,5,6-tetrahydro-2H-[1,4']bipyridinyl-3'-yl)-amide |
| 89 | Chiral | 2-(2,6-Difluoro-3-hydroxy-phenyl)-thiazole-4-carboxylic acid (5-amino-3-trifluoromethyl-3,4,5,6-tetrahydro-2H-[1,4']bipyridinyl-3'-yl)-amide |
| 90 | Chiral | 2-(2-Fluoro-5-hydroxy-phenyl)-thiazole-4-carboxylic acid (5-amino-3-trifluoromethyl-3,4,5,6-tetrahydro-2H-[1,4']bipyridinyl-3'-yl)-amide |

| Example | Structure | Name |
|---|---|---|
| 91 | Chiral | 2-(2-Fluoro-4-hydroxy-phenyl)-thiazole-4-carboxylic acid (5-amino-3-trifluoromethyl-3,4,5,6-tetrahydro-2H-[1,4']bipyridinyl-3'-yl)-amide |
| 92 | Chiral | 2-(2,6-Difluoro-4-hydroxy-phenyl)-thiazole-4-carboxylic acid [4-(3-amino-cyclohexyl)-pyridin-3-yl]-amide |
| 93 | Chiral | 2-(2,6-Difluoro-3-hydroxy-phenyl)-thiazole-4-carboxylic acid [4-(3-amino-cyclohexyl)-pyridin-3-yl]-amide |
| 94 | Chiral | 2-(2-Fluoro-5-hydroxy-phenyl)-thiazole-4-carboxylic acid [4-(3-amino-cyclohexyl)-pyridin-3-yl]-amide |

-continued

| Example | Structure | Name |
|---|---|---|
| 95 | 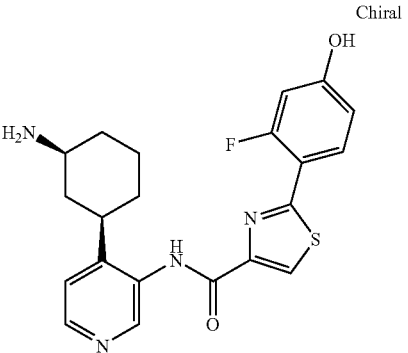 Chiral | 2-(2-Fluoro-4-hydroxy-phenyl)-thiazole-4-carboxylic acid [4-(3-amino-cyclohexyl)-pyridin-3-yl]-amide |
| 96 | 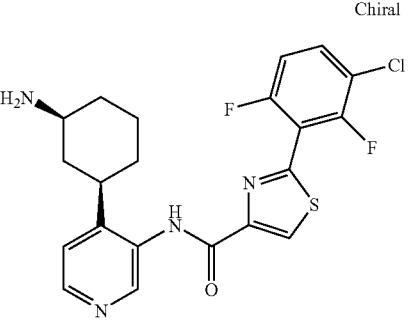 Chiral | 2-(3-Chloro-2,6-difluoro-phenyl)-thiazole-4-carboxylic acid [4-(3-amino-cyclohexyl)-pyridin-3-yl]-amide |
| 97 | 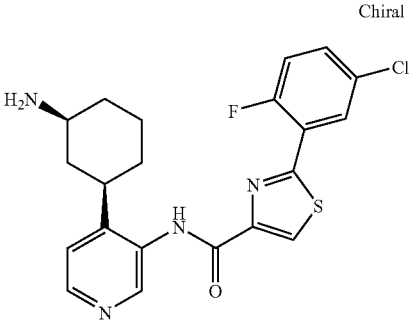 Chiral | 2-(5-Chloro-2-fluoro-phenyl)-thiazole-4-carboxylic acid [4-(3-amino-cyclohexyl)-pyridin-3-yl]-amide |
| 98 | 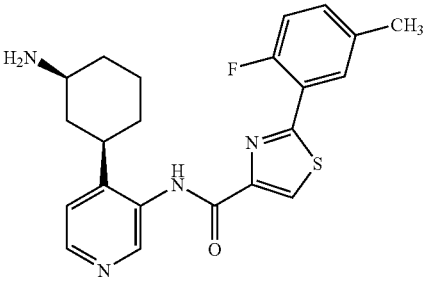 Chiral | 2-(2-Fluoro-5-methyl-phenyl)-thiazole-4-carboxylic acid [4-(3-amino-cyclohexyl)-pyridin-3-yl]-amide |

| Example | Structure | Name |
|---|---|---|
| 99 | 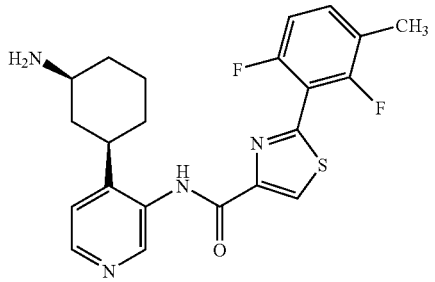 Chiral | 2-(2,6-Difluoro-3-methyl-phenyl)-thiazole-4-carboxylic acid [4-(3-amino-cyclohexyl)-pyridin-3-yl]-amide |

Pim1 ATP Depletion Assay

The activity of PIM1 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 5 nM Pim1 kinase and 80 µM BAD peptide (RSRHSSYPAGT-OH) in assay buffer (50 mM HEPES pH 7.5, 5 mM $MgCl_2$, and 1 mM DTT, 0.05% BSA) is added into each well. After 15 minutes, 10 µl of 40 µM ATP in assay buffer is added. Final assay concentrations are 2.5 nM PIM1, 20 µM ATP, 40 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim1 ATP depletion assay and found to exhibit an $IC_{50}$ values as shown in the table below. $IC_{50}$, the half maximal inhibitory concentration, represents the concentration of a test compound that is required for 50% inhibition of its target in vitro.

Pim2 ATP Depletion Assay

The activity of PIM2 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 10 nM Pim2 kinase and 20 µM BAD peptide (RSRHSSYPAGT-OH) in assay buffer (50 mM HEPES pH 7.5, 5 mM $MgCl_2$, and 1 mM DTT, 0.05% BSA) is added into each well. After 15 minutes, 10 µl of 8 µM ATP in assay buffer is added. Final assay concentrations are 5 nM PIM2, 4 µM ATP, 10 µM BAD peptide and 2.5% DMSO. The reaction is performed until approximately 50% of the ATP is depleted, then stopped with the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim2 ATP depletion assay and found to exhibit an $IC_{50}$ values as shown in the table below.

Pim3 ATP Depletion Assay

The activity of PIM3 is measured using a luciferase-luciferin based ATP detection reagent to quantify ATP depletion resulting from kinase-catalyzed phosphoryl transfer to a peptide substrate. Compounds to be tested are dissolved in 100% DMSO and directly distributed into white 384-well plates at 0.5 µl per well. To start the reaction, 10 µl of 10 nM Pim3 kinase and 200 µM BAD peptide (RSRHSSYPAGT-OH) in assay buffer (50 mM HEPES pH 7.5, 5 mM $MgCl_2$, and 1 mM DTT, 0.05% BSA) is added into each well. After 15 minutes, 10 µl of 80 µM ATP in assay buffer is added. Final assay concentrations are 5 nM PIM1, 40 µM ATP, 100 µM BAD peptide and 2.5% DMSO. The reaction is performed until approximately 50% of the ATP is depleted, then stopped by the addition of 20 µl KinaseGlo Plus (Promega Corporation) solution. The stopped reaction is incubated for 10 minutes and the remaining ATP detected via luminescence on the Victor2 (Perkin Elmer). Compounds of the foregoing examples were tested by the Pim3 ATP depletion assay and found to exhibit an $IC_{50}$ values as shown in the table below.

Cell Proliferation Assay

KMS11 (human myeloma cell line), were cultured in IMDM supplemented with 10% FBS, sodium pyruvate and antibiotics. Cells were plated in the same medium at a density of 2000 cells per well into 96 well tissue culture plates, with outside wells vacant, on the day of assay. MM1.s (human myeloma cell line), were cultured in RPMI1640 supplemented with 10% FBS, sodium pyruvate and antibiotics. Cells were plated in the same medium at a density of 5000 cells per well into 96 well tissue culture plates, with outside wells vacant, on the day of assay.

Test compounds supplied in DMSO were diluted into DMSO at 500 times the desired final concentrations before dilution into culture media to 2 times final concentrations. Equal volumes of 2x compounds were added to the cells in 96 well plates and incubated at 37° C. for 3 days.

After 3 days plates were equilibrated to room temperature and equal volume of Cell Titer-Glow Reagent (Promega) was added to the culture wells. The plates were agitated briefly and luminescent signal was measured with luminometer. The percent inhibition of the signal seen in cells treated with DMSO alone vs. cells treated with control compound was calculated and used to determine $EC_{50}$ values (i.e., the concentration of a test compound that is required to obtain 50% of the maximum effect in the cells) for tested compounds, as shown in Table 6 below.

IC50 and EC50 Activity of Compounds of the Invention

Using the procedures for Pim1 ATP depletion assay (PIM-1), Pim2 ATP depletion assay (PIM-2), and Pim3 ATP depletion assay (PIM-3), described above, the $IC_{50}$ concentration of compounds of the previous examples were determined as shown in the following table.

| Ex. No. | Structure | | Pim1 IC$_{50}$ (μM) | Pim2 IC$_{50}$ (μM) | Pim3 IC$_{50}$ (μM) |
|---|---|---|---|---|---|
| 1 | *(structure: (3R)-3-aminopiperidinyl linked to pyridine-NH-C(O)-thiazole-2,6-difluorophenyl)* | Chiral | 0.001 | 0.008 | 0.002 |
| 2 | *(structure: 3-amino-4-hydroxypiperidinyl linked to pyridine-NH-C(O)-thiazole-2,6-difluorophenyl)* | Chiral | 0.002 | 0.011 | 0.004 |
| 3 | *(structure: 3-amino-4-fluoropiperidinyl linked to pyridine-NH-C(O)-thiazole-2,6-difluorophenyl)* | Chiral | 0.002 | 0.023 | 0.005 |
| 5 | *(structure: 3-amino-5-hydroxypiperidinyl linked to pyridine-NH-C(O)-thiazole-2,6-difluorophenyl)* | | 0.015 | 0.077 | 0.013 |

-continued
| Ex. No. | Structure | Pim1 IC$_{50}$ (μM) | Pim2 IC$_{50}$ (μM) | Pim3 IC$_{50}$ (μM) |
|---|---|---|---|---|
| 6 | Chiral 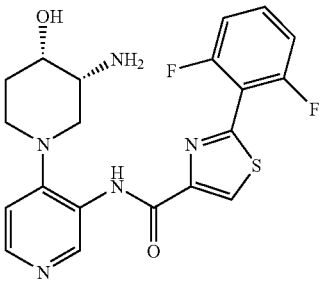 | 0.001 | 0.003 | 0.001 |
| 7 | 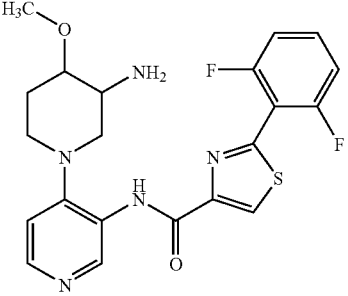 | 0.005 | 0.243 | 0.018 |
| 8 | Chiral 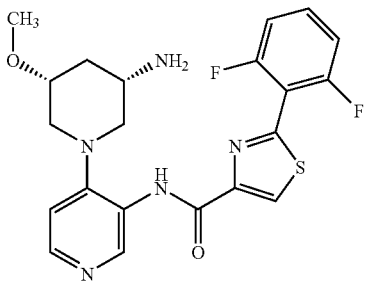 | 0.021 | 0.046 | 0.035 |
| 9 | Chiral 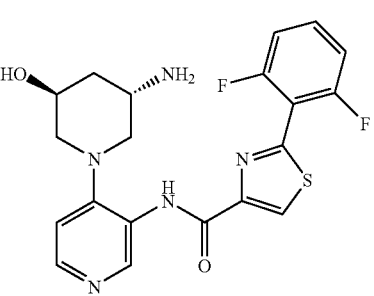 | 0.069 | 1.502 | 0.091 |

-continued

| Ex. No. | Structure | Pim1 IC$_{50}$ (μM) | Pim2 IC$_{50}$ (μM) | Pim3 IC$_{50}$ (μM) |
|---|---|---|---|---|
| 10 | Chiral | 2.220 | 0.479 | 0.322 |
| 11 | Chiral | 0.004 | 0.055 | 0.008 |
| 12 | Chiral | 0.057 | 0.208 | 0.045 |
| 13 | 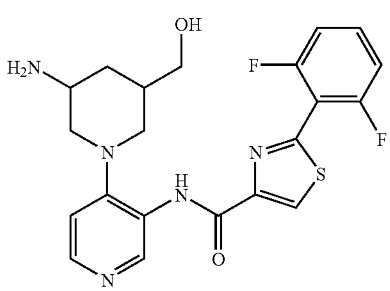 | 0.014 | 0.058 | 0.024 |
| 14 | 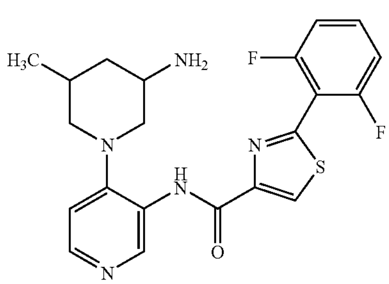 | 0.002 | 0.004 | 0.005 |

-continued
| Ex. No. | Structure | Pim1 IC$_{50}$ (μM) | Pim2 IC$_{50}$ (μM) | Pim3 IC$_{50}$ (μM) |
|---|---|---|---|---|
| 15 | 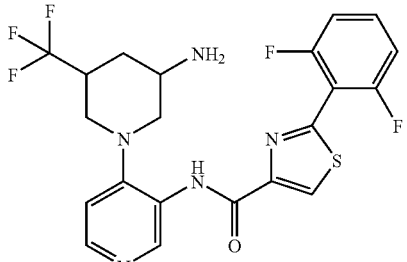 | 0.001 | 0.003 | 0.004 |
| 16 | 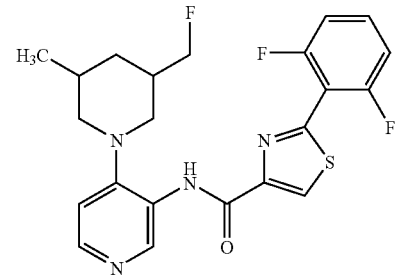 | 0.001 | 0.003 | 0.004 |
| 17 | Chiral 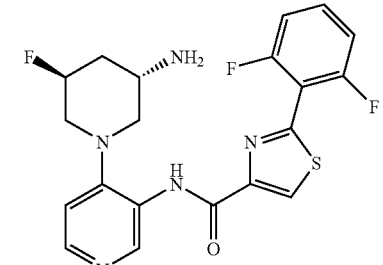 | 0.004 | 0.070 | 0.008 |
| 18 | 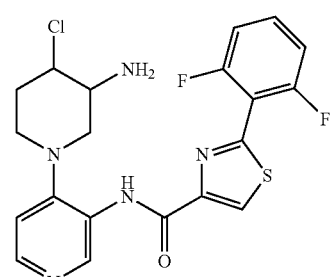 | 0.005 | 0.054 | 0.012 |
| 19 | 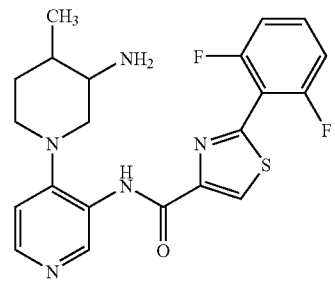 | 0.001 | 0.008 | 0.005 |

-continued
| Ex. No. | Structure | Pim1 IC$_{50}$ (μM) | Pim2 IC$_{50}$ (μM) | Pim3 IC$_{50}$ (μM) |
|---|---|---|---|---|
| 20 | 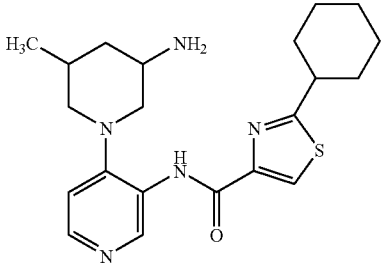 | 0.012 | 0.018 | 0.016 |
| 21 | 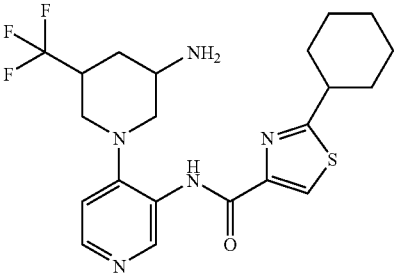 | 0.011 | 0.021 | 0.020 |
| 22 | Chiral 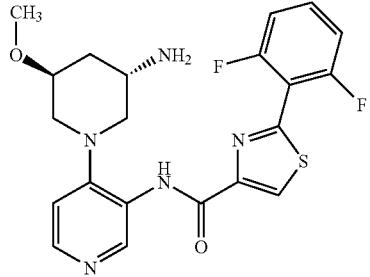 | 0.129 | 0.378 | 0.060 |
| 23 | Chiral 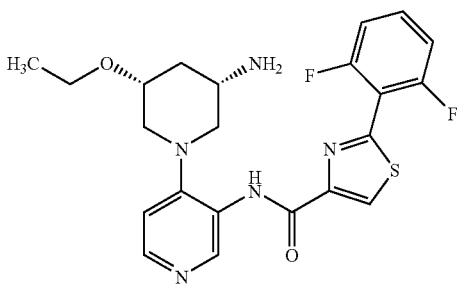 | 0.056 | 0.085 | 0.086 |

-continued

| Ex. No. | Structure | Pim1 IC$_{50}$ (μM) | Pim2 IC$_{50}$ (μM) | Pim3 IC$_{50}$ (μM) |
|---|---|---|---|---|
| 24 | Chiral | 0.002 | 0.038 | 0.004 |
| 25 | Chiral | 0.001 | 0.003 | 0.003 |
| 26 | 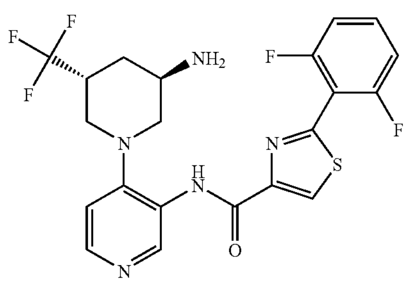 | 0.006 | 0.072 | 0.024 |
| 27 | Chiral | 0.001 | 0.003 | 0.003 |

-continued
| Ex. No. | Structure | Pim1 IC$_{50}$ (μM) | Pim2 IC$_{50}$ (μM) | Pim3 IC$_{50}$ (μM) |
|---|---|---|---|---|
| 28 | Chiral 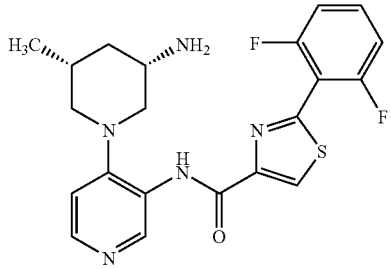 | 0.001 | 0.002 | 0.002 |
| 29 | Chiral 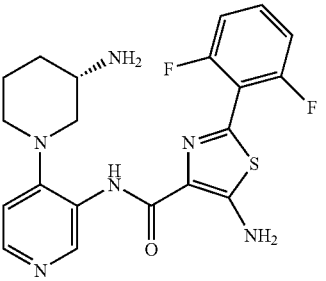 | 0.001 | 0.002 | 0.002 |
| 30 | 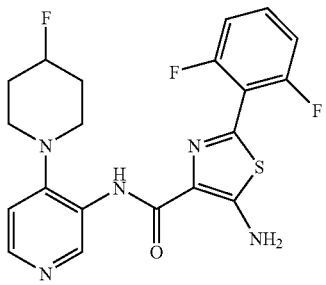 | 0.001 | 0.055 | 0.003 |
| 31 | 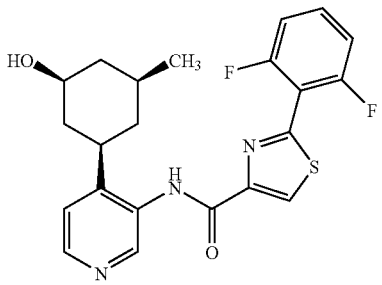 | 0.002 | 0.090 | 0.008 |
| 32 | 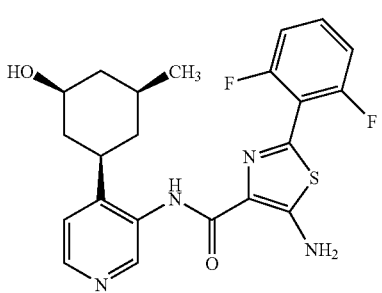 | 0.001 | 0.005 | 0.004 |

-continued

| Ex. No. | Structure | Pim1 IC$_{50}$ (μM) | Pim2 IC$_{50}$ (μM) | Pim3 IC$_{50}$ (μM) |
|---|---|---|---|---|
| 33 | Chiral | 0.001 | 0.003 | 0.003 |
| 34 | Chiral | 0.002 | 0.029 | 0.004 |
| 35 | Chiral | 0.009 | 0.125 | 0.009 |
| 36 | Chiral | 0.001 | 0.003 | 0.003 |

| Ex. No. | Structure | Pim1 IC$_{50}$ (μM) | Pim2 IC$_{50}$ (μM) | Pim3 IC$_{50}$ (μM) |
|---|---|---|---|---|
| 37 | 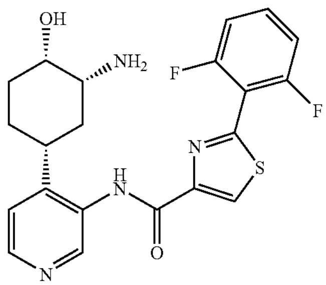 | 0.006 | 0.098 | 0.011 |
| 38 | 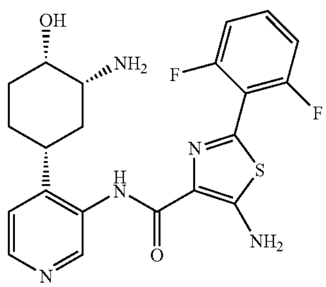 | 0.001 | 0.004 | 0.003 |
| 39 | 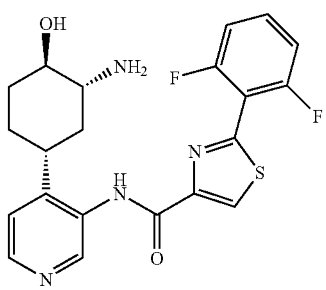 | 0.011 | 0.095 | 0.012 |
| 40 | 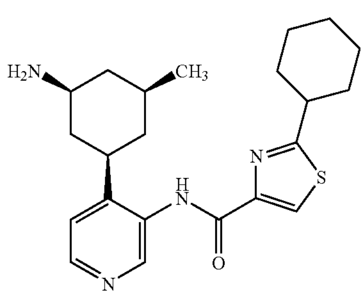 | 0.041 | 0.097 | 0.109 |
| 41 | 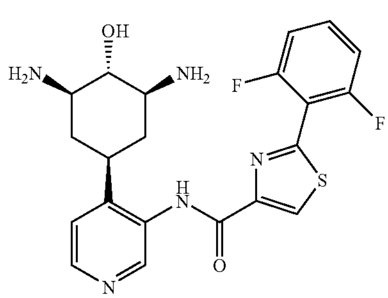 | 0.004 | 0.027 | 0.008 |

-continued

| Ex. No. | Structure | Pim1 IC$_{50}$ (μM) | Pim2 IC$_{50}$ (μM) | Pim3 IC$_{50}$ (μM) |
|---|---|---|---|---|
| 42 | 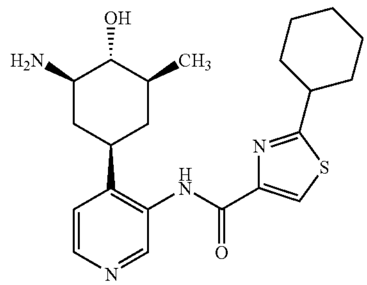 | 0.146 | 0.250 | 0.215 |
| 43 | 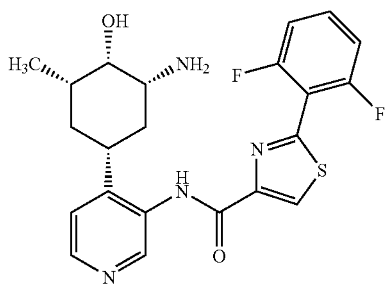 | 0.005 | 0.046 | 0.015 |
| 45 | Chiral | 0.001 | 0.007 | 0.003 |
| 46 | Chiral | 0.001 | 0.016 | 0.003 |

-continued

| Ex. No. | Structure | Pim1 IC$_{50}$ (μM) | Pim2 IC$_{50}$ (μM) | Pim3 IC$_{50}$ (μM) |
|---|---|---|---|---|
| 48 | Chiral | 0.0020 | 0.0177 | 0.0023 |
| 49 | Chiral | 0.0019 | 0.0099 | 0.0042 |
| 50 | Chiral | 0.0032 | 0.0838 | 0.0083 |
| 52 | Chiral | 0.001 | 0.004 | 0.002 |

-continued

| Ex. No. | Structure | Pim1 IC$_{50}$ (μM) | Pim2 IC$_{50}$ (μM) | Pim3 IC$_{50}$ (μM) |
|---|---|---|---|---|
| 53 | Chiral | 0.001 | 0.020 | 0.003 |
| 54 | Chiral | 0.001 | 0.009 | 0.003 |
| 55 | Chiral | 0.003 | 0.015 | 0.005 |
| 56 | Chiral | 0.001 | 0.012 | 0.003 |

| Ex. No. | Structure | Pim1 IC$_{50}$ (µM) | Pim2 IC$_{50}$ (µM) | Pim3 IC$_{50}$ (µM) |
|---|---|---|---|---|
| 57 | Chiral | 0.001 | 0.004 | 0.002 |
| 58 | 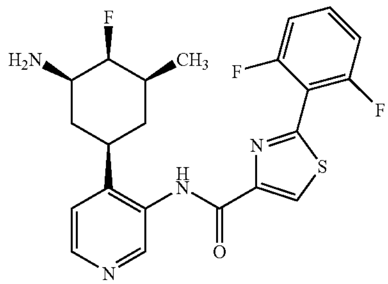 | 0.004 | 0.047 | 0.018 |

Using the procedures for Cell Proliferation Assay described above, the EC$_{50}$ concentration of compounds of the previous examples were determined in KMS11 cells as shown in the following table.

| Ex. No. | Structure | KMS11 EC$_{50}$ (µM) |
|---|---|---|
| 1 | Chiral | 1.17 |
| 2 | Chiral | 1.57 |
| 6 | Chiral | 0.41 |
| 8 | Chiral | 4.70 |

| Ex. No. | Structure | KMS11 EC$_{50}$ (μM) |
|---|---|---|
| 11 | Chiral 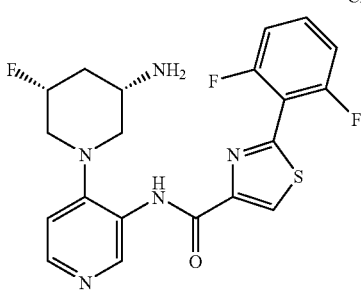 | 6.10 |
| 14 | 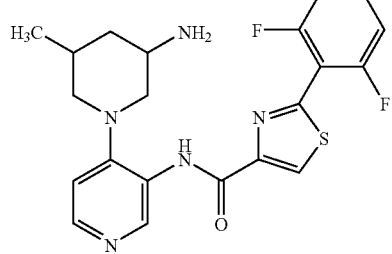 | 0.83 |
| 15 | 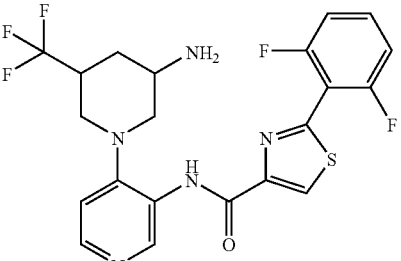 | 0.31 |
| 16 | 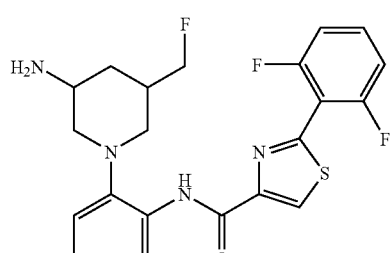 | 2.38 |
| 19 | 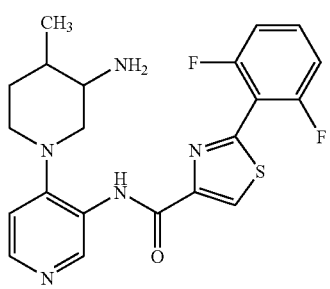 | 0.93 |
| 23 | Chiral 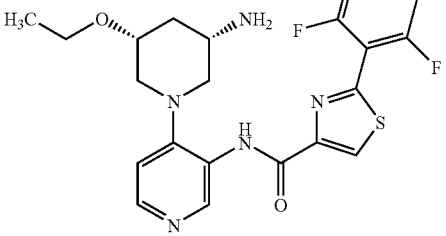 | 6.54 |
| 27 | Chiral 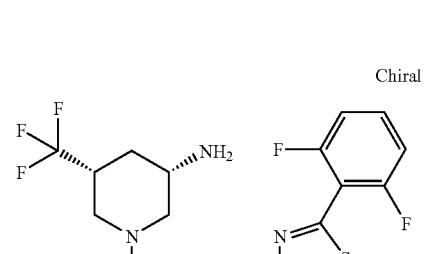 | 0.46 |
| 28 | Chiral 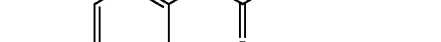 | 0.40 |
| 29 | Chiral  | 0.04 |

| Ex. No. | Structure | KMS11 EC$_{50}$ (μM) |
|---|---|---|
| 33 | Chiral | 0.43 |
| 34 | Chiral | 5.02 |
| 36 | Chiral | 0.56 |
| 38 | 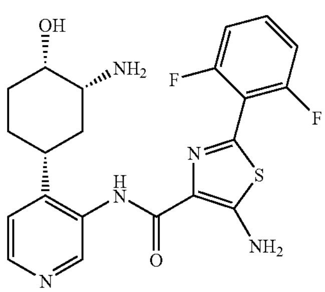 | 1.89 |
| 41 | 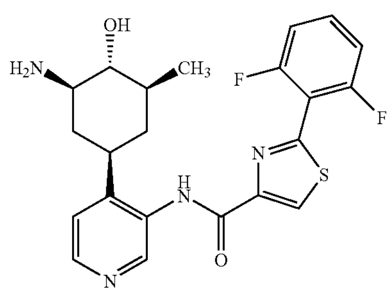 | >10 |
| 42 | | |
| 43 | | |
| 45 | Chiral | 0.92 |

The invention claimed is:

1. A compound of Formula II, or a stereoisomer, tautomer, or pharmaceutically acceptable salt thereof,

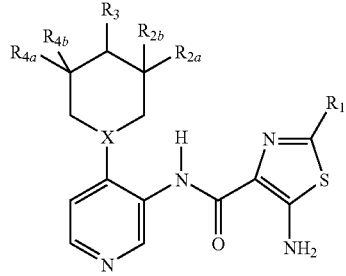

II wherein:
R$_1$ is selected from —NH—CO-alkyl, substituted or unsubstituted cycloalkyl, substituted or unsubstituted heterocycloalkyl, substituted or unsubstituted aryl, and substituted or unsubstituted heteroaryl;
X represents CH or N;
R$_{2a}$ is selected from —H, —OH, alkyl, alkoxy, haloalkyl, aminoalkyl, hydroxyalkyl, halo, amino and bezoate;

$R_{2b}$ is selected from —H and alkyl;
$R_3$ is selected from H, OH, alkyl, alkoxy and halo;
$R_{4a}$ is selected from —OH, alkyl, alkoxy, haloalkyl, aminoalkyl, hydroxyalkyl, halo and amino; and
$R_{4b}$ is selected from H, alkyl and halo.

2. A compound of claim 1 wherein $R_1$ is selected from substituted or unsubstituted phenyl, substituted or unsubstituted cyclohexyl, and substituted or unsubstituted piperidinyl.

3. A compound of claim 2 wherein $R_1$ is selected from

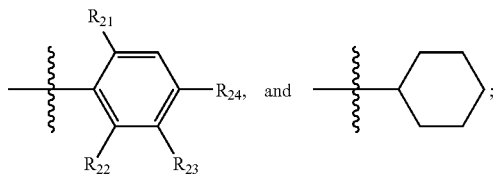

wherein:
$R_{21}$ is H or halo;
$R_{22}$ is H or halo;
$R_{23}$ is selected from H, halo, alkyl and alkoxy; and
$R_{24}$ is H or OH.

4. A compound of claim 3 wherein $R_{21}$ and $R_{22}$ are independently selected from H and F.

5. A compound of claim 3 wherein $R_{23}$ is selected from H, Cl, F, —OC$_2$H$_5$, —OCH$_3$, and —OCH(CH$_3$)$_2$.

6. A compound of claim 1 wherein $R_{2a}$ is selected from H, methyl, ethyl, methoxy, ethoxy, fluoromethyl, trifluoromethyl, aminomethyl and hydroxymethyl.

7. A compound of claim 1 wherein $R_3$ is selected from H, —OH, methyl, methoxy, F and Cl.

8. A compound of claim 1 wherein $R_{4a}$ is selected from —OH, methyl, ethyl, trifluoromethyl, methoxy, ethoxy, amino, F and Cl.

9. A compound of claim 1 wherein $R_{4b}$ is selected from methyl and F.

10. A compound of claim 1 selected from the group consisting of (S)-5-amino-N-(4-(3-aminopiperidin-1-yl)pyridin-3-yl)-2-(2,6-difluorophenyl)-thiazole-4-carboxamide, or a stereoisomer, tautomer, or pharmaceutically acceptable salt thereof.

11. A compound of claim 1, selected from the group consisting of 5-amino-N-(4-((1R,3S)-3-aminocyclohexyl)pyridin-3-yl)-2-(2,6-difluorophenyl)thiazole-4-carboxamide, 5-amino-N-(4-(3-amino-4-hydroxycyclohexyl)pyridin-3-yl)-2-(2,6-difluorophenyl)thiazole-4-carboxamide, and 5-amino-2-(2,6-difluorophenyl)-N-(4-((1R,3S,5S)-3-hydroxy-5-methylcyclohexyl)pyridin-3-yl)thiazole-4-carboxamide, or a stereoisomer, tautomer, or pharmaceutically acceptable salt thereof.

12. A composition comprising a therapeutically effective amount of compound of claim 1, or a stereoisomer, tautomer, or pharmaceutically acceptable salt thereof, together with a pharmaceutically acceptable carrier.

13. The composition of claim 12, wherein the compound is (S)-5-amino-N-(4-(3-aminopiperidin-1-yl)pyridin-3-yl)-2-(2,6-difluorophenyl)thiazole-4-carboxamide, or a stereoisomer, tautomer, or pharmaceutically acceptable salt thereof.

14. The composition of claim 12, wherein the compound is selected from 5-amino-N-(4-((1R,3S)-3-aminocyclohexyl)pyridin-3-yl)-2-(2,6-difluorophenyl)thiazole-4-carboxamide, 5-amino-N-(4-(3-amino-4-hydroxycyclohexyl)pyridin-3-yl)-2-(2,6-difluorophenyl)thiazole-4-carboxamide, and 5-amino-2-(2,6-difluorophenyl)-N-(4-((1R,3S,5S)-3-hydroxy-5-methylcyclohexyl)pyridin-3-yl)thiazole-4-carboxamide, or a stereoisomer, tautomer, or pharmaceutically acceptable salt thereof.

* * * * *